(12) United States Patent
Macri et al.

(10) Patent No.: US 11,904,101 B2
(45) Date of Patent: *Feb. 20, 2024

(54) DIGITAL VIRTUAL LIMB AND BODY INTERACTION

(71) Applicants: Vincent John Macri, Tallahassee, FL (US); Vincent James Macri, New York, NY (US); Paul Zilber, Plainview, NY (US)

(72) Inventors: Vincent John Macri, Tallahassee, FL (US); Vincent James Macri, New York, NY (US); Paul Zilber, Plainview, NY (US)

( * ) Notice: Subject to any disclaimer, the term of this patent is extended or adjusted under 35 U.S.C. 154(b) by 618 days.

This patent is subject to a terminal disclaimer.

(21) Appl. No.: 16/582,404

(22) Filed: Sep. 25, 2019

(65) Prior Publication Data

US 2020/0016363 A1 Jan. 16, 2020

Related U.S. Application Data

(63) Continuation-in-part of application No. 15/880,271, filed on Jan. 25, 2018, now Pat. No. 10,632,366.
(Continued)

(51) Int. Cl.
*A61M 21/00* (2006.01)
*G09B 19/00* (2006.01)
*G06F 3/01* (2006.01)

(52) U.S. Cl.
CPC ............ *A61M 21/00* (2013.01); *G06F 3/016* (2013.01); *G09B 19/003* (2013.01);
(Continued)

(58) Field of Classification Search
CPC ............ A61M 21/00; A61M 2021/005; A61M 2205/056; A61M 2205/583; G09B 19/003; G06F 3/016; G06F 3/014
(Continued)

(56) References Cited

U.S. PATENT DOCUMENTS 5,078,152 A 1/1992 Bond et al.
5,429,140 A 7/1995 Burdea et al.
(Continued)

FOREIGN PATENT DOCUMENTS

JP 2002306632 A 10/2002
KR 20120137327 A 12/2012
(Continued)

OTHER PUBLICATIONS

Ultraleap, "Leap Motion Developer", Retrieved from the Internet on Aug. 5, 2020: https://developer.leapmotion.com/documentation, pp. 1-14.
(Continued)

*Primary Examiner* — Malina D. Blaise
(74) *Attorney, Agent, or Firm* — Resolute Legal PLLC

(57) ABSTRACT

Methods and systems for pre-action training are described. In an aspect, a method is presented for constructing a user-controllable image comprising obtain anatomical and physiological data associated with a body, storing the anatomical and physiological data in a database; and creating the user-controllable image based on the stored anatomical and physiological data. At least a moveable portion of the user-controllable image may be constructed to move based on input from a user. Victims of stroke, TBI, or other neurological setbacks may pre-train their nervous system for use of one or more injured body parts. The methods and systems described provide pre-action training control of non-virtual prostheses, exoskeleton body parts, powered orthotic devices, robots or other motile or audiovisual output devices used to improve therapy, rehabilitation, and in some circumstances to lessen or prevent blood clots. Therapy may be remotely delivered.

3 Claims, 29 Drawing Sheets

Related U.S. Application Data which is a continuation-in-part of application No. 14/891,789, filed as application No. PCT/US2014/038447 on May 16, 2014, now Pat. No. 10,603,545, said application No. 15/880,271 is a continuation-in-part of application No. 13/841,901, filed on Mar. 15, 2013, now Pat. No. 10,096,265.

(60) Provisional application No. 62/499,977, filed on Feb. 9, 2017, provisional application No. 62/499,453, filed on Jan. 25, 2017, provisional application No. 61/830,465, filed on Jun. 3, 2013, provisional application No. 61/824,892, filed on May 17, 2013, provisional application No. 61/665,221, filed on Jun. 27, 2012.

(52) U.S. Cl.
CPC . *A61M 2021/005* (2013.01); *A61M 2205/056* (2013.01); *A61M 2205/583* (2013.01); *G06F 3/014* (2013.01)

(58) Field of Classification Search
USPC .......................................................... 434/262
See application file for complete search history.

(56) References Cited

U.S. PATENT DOCUMENTS

| | | | |
|---|---|---|---|
| 5,554,033 A | 9/1996 | Bizzi et al. | |
| 5,846,086 A | 12/1998 | Bizzi et al. | |
| 5,984,880 A | 11/1999 | Lander et al. | |
| 6,057,846 A | 5/2000 | Sever, Jr. | |
| 6,098,458 A | 8/2000 | French et al. | |
| 6,162,189 A * | 12/2000 | Girone | A63B 23/08 |
| | | | 600/595 |
| 6,164,973 A | 12/2000 | Macri et al. | |
| 6,421,048 B1 | 7/2002 | Shih et al. | |
| 6,666,831 B1 | 12/2003 | Edgerton et al. | |
| 6,749,432 B2 | 6/2004 | French et al. | |
| 6,827,579 B2 | 12/2004 | Burdea et al. | |
| 7,179,234 B2 | 2/2007 | Nashner | |
| 7,252,644 B2 | 8/2007 | Dewald et al. | |
| 7,460,125 B2 | 12/2008 | Yang et al. | |
| 7,731,500 B2 | 6/2010 | Feygin et al. | |
| 7,993,291 B2 | 8/2011 | Karkanias et al. | |
| 8,214,029 B2 * | 7/2012 | Koeneman | A61H 1/02 |
| | | | 600/595 |
| 8,425,438 B2 * | 4/2013 | Fujimoto | G06F 3/014 |
| | | | 601/40 |
| 8,496,564 B2 | 7/2013 | Zlobinsky | |
| 8,834,169 B2 | 9/2014 | Reinkensmeyer et al. | |
| 9,271,660 B2 | 3/2016 | Luo et al. | |
| 9,326,909 B2 * | 5/2016 | Liu | A63B 22/00 |
| 9,403,056 B2 | 8/2016 | Weinberg et al. | |
| 9,483,622 B1 | 11/2016 | Snyder | |
| 10,380,910 B2 | 8/2019 | Wu et al. | |
| 2002/0120362 A1 | 8/2002 | Lathan et al. | |
| 2002/0146672 A1 * | 10/2002 | Burdea | A63B 23/16 |
| | | | 434/258 |
| 2004/0254771 A1 | 12/2004 | Riener et al. | |
| 2004/0267320 A1 | 12/2004 | Taylor et al. | |
| 2005/0250083 A1 | 11/2005 | Macri et al. | |
| 2006/0074822 A1 | 4/2006 | Eda et al. | |
| 2006/0084050 A1 | 4/2006 | Haluck | |
| 2006/0287617 A1 | 12/2006 | Taub et al. | |
| 2007/0016265 A1 | 1/2007 | Davoodi et al. | |
| 2007/0048702 A1 | 3/2007 | Jang et al. | |
| 2007/0066918 A1 * | 3/2007 | Dewald | A63B 21/00178 |
| | | | 482/901 |
| 2007/0126733 A1 | 6/2007 | Yang et al. | |
| 2008/0009771 A1 | 1/2008 | Perry et al. | |
| 2008/0132383 A1 | 6/2008 | Einav et al. | |
| 2009/0221928 A1 | 9/2009 | Einav et al. | |
| 2009/0259148 A1 | 10/2009 | Willmann et al. | |
| 2009/0326341 A1 | 12/2009 | Furlan | |
| 2011/0009241 A1 | 1/2011 | Lane et al. | |
| 2011/0054870 A1 | 3/2011 | Dariush et al. | |
| 2012/0004579 A1 | 1/2012 | Luo et al. | |
| 2012/0021394 A1 * | 1/2012 | deCharms | A61B 5/486 |
| | | | 434/262 |
| 2012/0077163 A1 | 3/2012 | Sucar Succar et al. | |
| 2012/0108909 A1 | 5/2012 | Slobounov et al. | |
| 2012/0142416 A1 * | 6/2012 | Joutras | G06F 3/014 |
| | | | 463/36 |
| 2012/0157263 A1 * | 6/2012 | Sivak | G16H 40/63 |
| | | | 482/4 |
| 2013/0035734 A1 | 2/2013 | Soler Fernandez et al. | |
| 2013/0046206 A1 | 2/2013 | Preminger | |
| 2013/0072353 A1 | 3/2013 | Alessandri et al. | |
| 2013/0096940 A1 | 4/2013 | Hayes | |
| 2013/0123667 A1 | 5/2013 | Komatireddy et al. | |
| 2013/0138011 A1 | 5/2013 | Ang et al. | |
| 2013/0171596 A1 | 7/2013 | French | |
| 2013/0252216 A1 | 9/2013 | Clavin et al. | |
| 2013/0316316 A1 | 11/2013 | Flavell et al. | |
| 2013/0342527 A1 | 12/2013 | Molyneaux et al. | |
| 2014/0004493 A1 | 1/2014 | Macri et al. | |
| 2014/0031098 A1 | 1/2014 | Tacconi | |
| 2014/0147820 A1 * | 5/2014 | Snow | G09B 19/0038 |
| | | | 434/247 |
| 2014/0287876 A1 | 9/2014 | Etter et al. | |
| 2014/0364230 A1 | 12/2014 | Borghese et al. | |
| 2014/0371633 A1 | 12/2014 | Evin et al. | |
| 2015/0196800 A1 | 7/2015 | Macri et al. | |
| 2015/0202492 A1 | 7/2015 | Domansky et al. | |
| 2016/0082319 A1 | 3/2016 | Macri et al. | |
| 2016/0086500 A1 | 3/2016 | Kaleal, III | |
| 2016/0129343 A1 * | 5/2016 | Domansky | A61B 5/486 |
| | | | 463/7 |
| 2016/0213978 A1 * | 7/2016 | Ban | G06F 3/014 |
| 2016/0235323 A1 | 8/2016 | Tadi et al. | |
| 2017/0209737 A1 | 7/2017 | Tadi et al. | |
| 2017/0325719 A1 | 11/2017 | Courtine et al. | |
| 2018/0184948 A1 | 7/2018 | Tadi et al. | |
| 2018/0214768 A1 * | 8/2018 | Macri | G09B 19/003 |
| 2018/0228430 A1 | 8/2018 | Perez Marcos et al. | |
| 2018/0229081 A1 | 8/2018 | Yi et al. | |
| 2018/0239430 A1 | 8/2018 | Tadi et al. | |
| 2018/0239956 A1 | 8/2018 | Tadi et al. | |
| 2018/0240261 A1 | 8/2018 | Tadi et al. | |
| 2018/0262744 A1 | 9/2018 | Tadi et al. | |
| 2018/0275760 A1 | 9/2018 | Nicolet et al. | |
| 2018/0275766 A1 | 9/2018 | Condolo | |
| 2018/0336973 A1 | 11/2018 | Tadi et al. | |
| 2019/0009133 A1 | 1/2019 | Mettler May | |
| 2019/0025919 A1 | 1/2019 | Tadi et al. | |
| 2019/0336381 A1 * | 11/2019 | Koltzi | A61H 1/0285 |
| 2022/0338761 A1 * | 10/2022 | Maddahi | A61B 5/486 |

FOREIGN PATENT DOCUMENTS

| | | |
|---|---|---|
| WO | 2011123059 A1 | 10/2011 |
| WO | 2012161657 A1 | 11/2012 |
| WO | 2013136287 A1 | 9/2013 |
| WO | 2014/154839 A1 | 10/2014 |
| WO | 2016/081830 A1 | 5/2016 |
| WO | 2018/134686 A3 | 7/2018 |
| WO | 2018/142228 A2 | 8/2018 |
| WO | 2018/146546 A1 | 8/2018 |
| WO | 2018/146558 A3 | 8/2018 |
| WO | 2019016811 A1 | 1/2019 |

OTHER PUBLICATIONS

Biospace, "Robotic Stroke Therapy Devices from Kinetic Muscles Inc. to be Marketed Internationally", Mar. 23, 2010, Retrieved from the Internet: https://www.biospace.com/article/releases/robotic-stroke-therapy-devices-from-b-kinetic-muscles-inc-b-to-be-marketed-internationally-/, pp. 1-3.

(56) References Cited

OTHER PUBLICATIONS

Jeffrey Rogers et al., "Elements virtual rehabilitation improves motor, cognitive, and functional outcomes in adult stroke: evidence from a randomized controlled pilot study" ,Journal of NeroEngineering and Rehabilitation, vol. 16, No. 56, 2019, pp. 1-13.
Neofect, Retrieved from the Internet Apr. 2020: https://www.neofect.com/en/product/stroke-therapy-hand/, pp. 1-9.
Ayca Utkan Karasu et al., "Effectiveness of Wii-based rehabilitation in stroke: A randomized controlled study", Journal of Rehabilitation Medicine, vol. 50, No. 5, May 2018, pp. 406-412.
Jintronix, Retrieved from the Internet Apr. 2020: http://www.jintronix.com/, pp. 1-18.
Virtualis, "Funcitional Rehabilitation", Retrieved from the Internet Apr. 2020: https://virtualisvr.com/en/functional-rehabilitation/, pp. 1-20.
Xrhealth, Retrieved from the Internet Apr. 2020: https://www.xr.health/, pp. 1-13.
Constant Therapy, Retrieved from the Internet Apr. 2020: https://thelearningcorp.com/constant-therapy/, pp. 1-7.
Bioness, Retrieved from the Internet Apr. 2020: https://www.bioness.com/BITS.php, pp. 1-3.
TRC, Retrieved from the Internet Apr. 2020: https://www.trcare.net/product, pp. 1-3.
Bertec, "Prime IVR", Retrieved from the Internet Apr. 2020: https://www.bertec.com/products/prime-ivr, pp. 1-9.
Rehab-Robotics, Retrieved from the Internet Apr. 2020: http://www.rehab-robotics.com.hk/hoh/index.html, p. 1.
Myomo, Retrieved from the Internet Apr. 2020: https://myomo.com/what-is-a-myopro-orthosis/, p. 1-6.
Kinetec, "Continuous Passive Motion", Retrieved from the Internet Apr. 2020: https://kinetecuk.com/categories/continuous-passive-motion, p. 1-4.
Chattanooga Rehab, Retrieved from the Internet Apr. 2020: https://www.chattanoogarehab.com/us/, pp. 1-9.
Daiya, "Power Assist Glove", Retrieved from the Internet Apr. 2020: https://www.daiyak.co.jp/en/product/detail/280?k=assist+glove&s=0, p. 1-6.
Neofect, "Neomano", Retrieved from the Internet Apr. 2020: https://www.neofect.com/us/neomano, pp. 1-13.
The Medcom Group, Ltd, "QAL Medical 6000X WaveFlex Hand CPM", Retrieved from the Internet Apr. 2020: https://www.medcomgroup.com/qal-medical-6000x-waveflex-hand-cpm/, pp. 1-7.
Extended European Search Report dated Jul. 9, 2020, European Patent Application No. 19207843.4, pp. 1-9.
Macri et al., "Repairing Brain-Motor Disability," International ABI Clinical Study Czech Republic Poster, (c)2015, 1 page.
International Search Report dated Oct. 14, 2014, International Application No. PCT/US2014/038447, pp. 1-4.
Lebedev M.A., et al., "Brain-Machine Interfaces: Past, Present and Future" Trends in Neurosciences vol. 29, No. 9, Sep. 2006, pp. 536-546.
Kynan Eng et al., "Interactive visuo-motor therapy system for stroke rehabilitation," Medical & biological engineering & computing, vol. 45, No. 9, 2007, pp. 901-907.
Pawel Pyk et al., "A Paediatric Interactive Therapy System for Arm and Hand Rehabilitation," In 2008 Virtual Rehabilitation, IEEE, pp. 127-132.
PCT International Search Report and Written Opinion dated Dec. 17, 2021, International Application No. PCT/US2021/48436, pp. 1-8.

\* cited by examiner

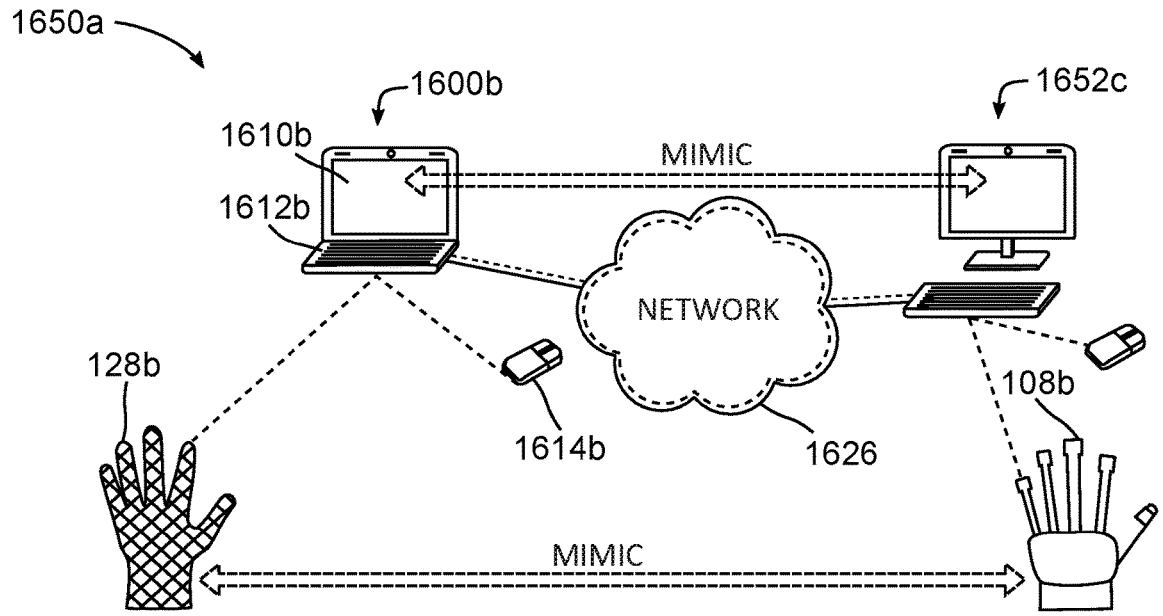
FIG. 23B
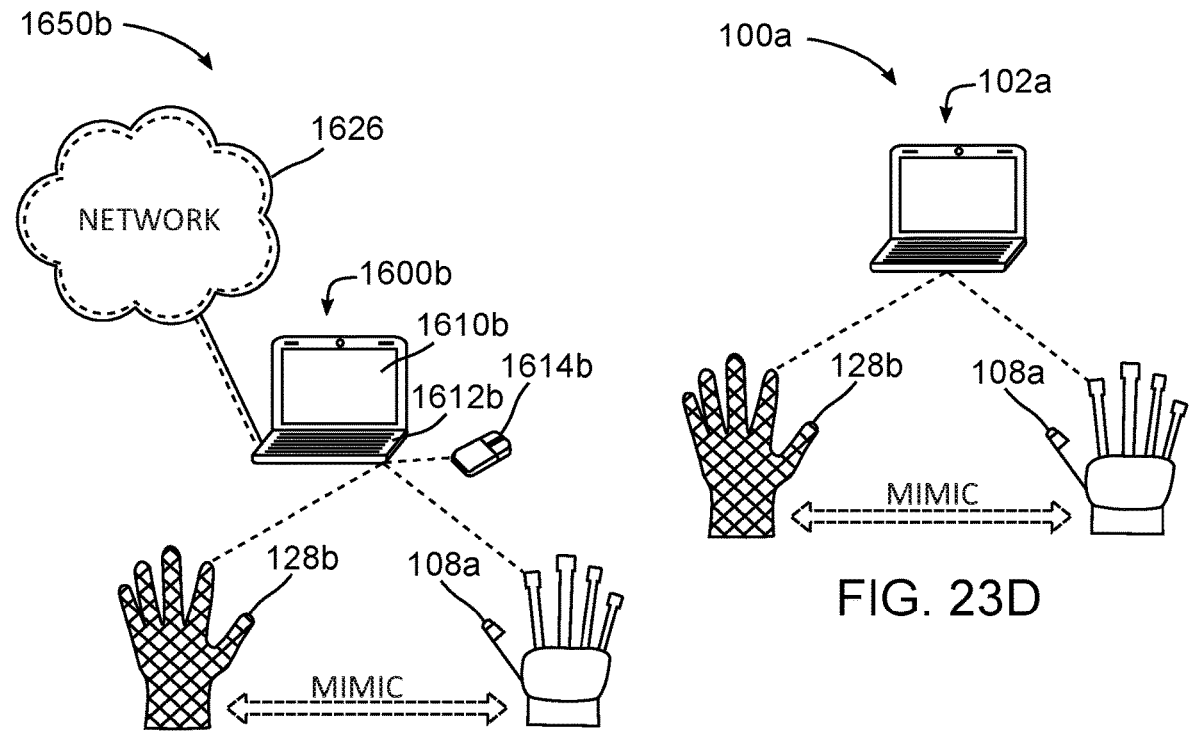
FIG. 23C
FIG. 23D

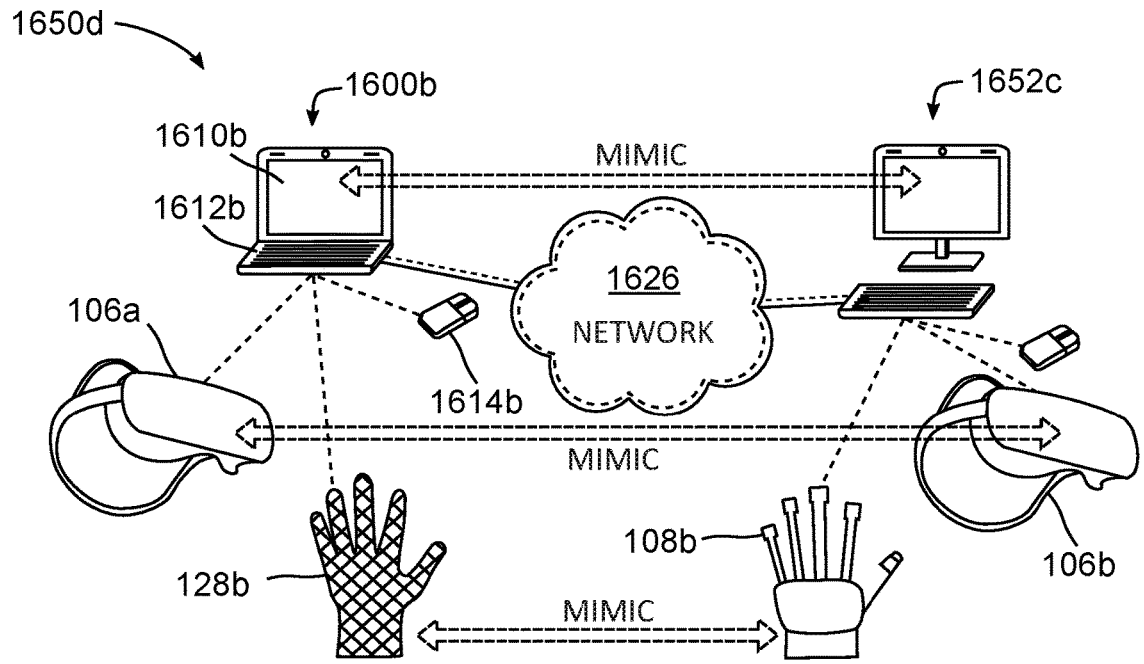
FIG. 23E
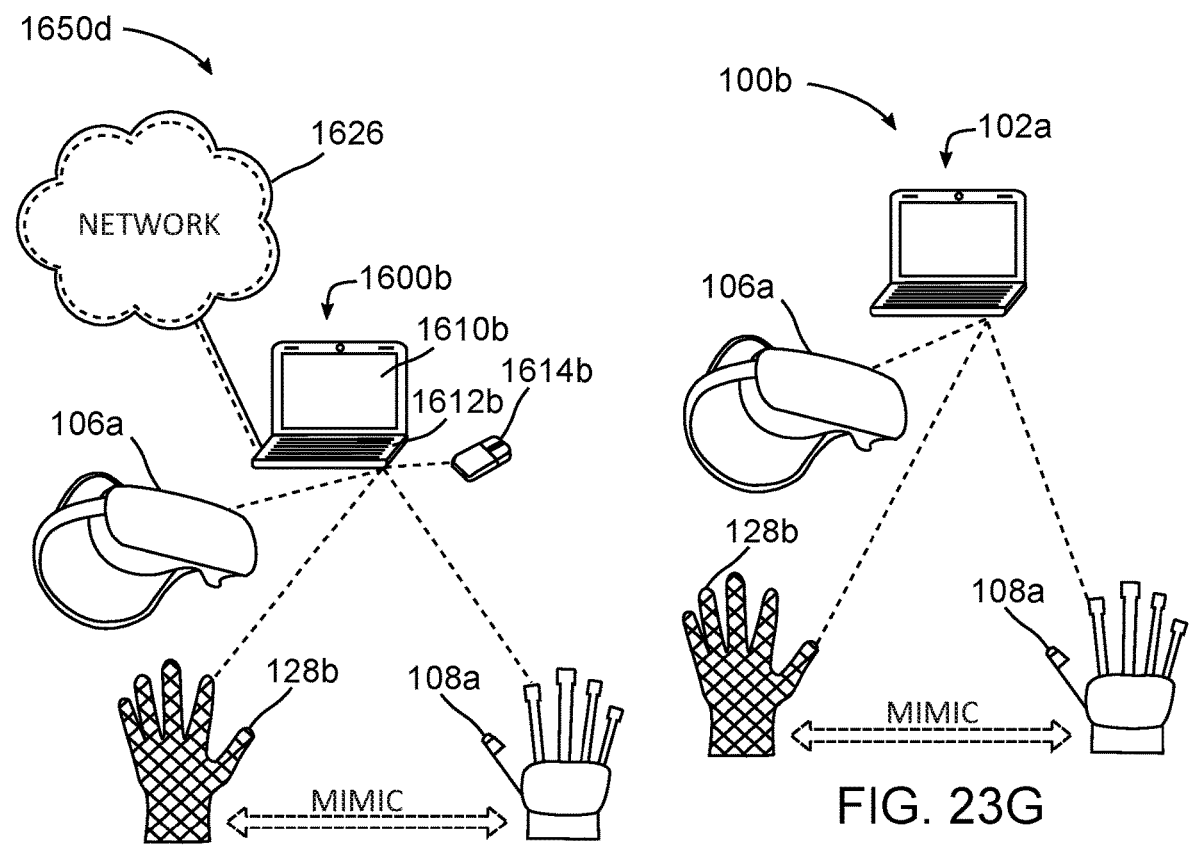
FIG. 23F
FIG. 23G

DIGITAL VIRTUAL LIMB AND BODY INTERACTION

CROSS REFERENCE TO RELATED APPLICATIONS

This application is a continuation-in-part of prior U.S. application Ser. No. 15/880,271, filed Jan. 25, 2018, which is a continuation-in-part of prior U.S. application Ser. No. 13/841,901, filed Mar. 15, 2013, which claims the benefit under 35 U.S.C. § 119(e) of U.S. Provisional Application No. 61/665,221, filed Jun. 27, 2012; and this application is a continuation-in-part of prior U.S. application Ser. No. 14/891,789, filed Nov. 17, 2015, which was a 371 National of International PCT/US2014/038447, filed May 16, 2014, and which claims the benefit under 35 U.S.C. § 119(e) of U.S. Provisional Application No. 61/824,892, filed on May 17, 2013, and also claims the benefit under 35 U.S.C. § 119(e) of U.S. Provisional Application No. 61/830,456, filed on Jun. 3, 2013; and this application claims the benefit under 35 U.S.C. § 119(e) of U.S. Provisional Application No. 62/499,453 filed Jan. 25, 2017, and this application claims the benefit under 35 U.S.C. § 119(e) of U.S. Provisional Application No. 62/499,977 filed Feb. 9, 2017; all of which are incorporated by reference herein.

FIELD OF THE DISCLOSURE

The present disclosure relates to movement therapy apparatus, system, and method.

SUMMARY OF THE DISCLOSURE

Embodiments described herein pertain to the field of user self-teaching pre-action gaming simulations, synonymously pre-action training, pre-action exercise, pre-action exercise games (PEGs), pre-action games and exercise (PAGEs), or instantiating kinetic imagery in virtual environments. The present disclosure further relates to constructing, configuring, or controlling user controllable images as used in pre-action training. The present disclosure further relates to methods and systems that provide for user pre-action training control of output devices such as non-virtual prostheses, powered orthotic devices, exoskeleton body parts, robots or other motile, motorized, or audiovisual output devices. The present disclosure further relates to tele-rehabilitation methods and systems that provide for rehabilitation services delivered at least in part using remote networked devices. The present disclosure further relates to tele-rehabilitation methods and systems comprising machine learning based modeling of rehabilitation treatment regimens having optimized predicted outcomes and a rehabilitation treatment recommender engine.

The broad medical problem is that the individuals most in need of care e.g., patients, survivors and other health-affected individuals (synonymously "users") have few, if any, simulations tailored to their needs and few in the field. The users' goals may include regaining or improving processes that enable performing activities of unaffected living after, without limitation: neurological injury or condition resulting from penetrating or non-penetrating insult injury or stress; or physical injury due to invasive or non-invasive causation; or experiencing psychological, neurological, or neurochemical disorder. The general economic problem is that the users undergo long-term and costly therapeutic and rehabilitative procedures therefore consuming significant healthcare services and costs without recourse to heuristic health improvement methods and systems. The access-to-care problem is that when affected by an injury, condition, or disorder, there are insufficient methods and systems to activate needed brain processes, or to stimulate, much less repeatedly stimulate, without limitation, neurons, neurological support cells, inter-neuron communications, gray and white matter cortical circuitry, other brain circuits or communications or tissues or proteins of the brain or central nervous system. The user's more particular medical, therapeutic, and rehabilitative care problems are to use the method and systems at least to improve the neurological, physical, or psychological conditions noted above.

Further, the broad medical problem is that while physical movement simulations are extensively in use, individuals most in need of care, specifically survivors and other health-affected individuals (synonymously "users") have few if any simulations and correlative physical device activations/actuations tailored to their needs and few in said field. Survivors' goals may include regaining or improving processes that enable performing activities of unaffected living after, without limitation: neurological injury, disorder or condition resulting from penetrating or non-penetrating insult injury or stress; or physical injury due to invasive or non-invasive causation; or experiencing psychological or neurochemical disorder.

Further, the user's medical therapeutic and rehabilitative care problems include access to diagnoses or measurements or biomarkers of brain processes or activations, or determinations of amounts or levels of biological substances, without limitation, tau proteins. One solution to the users' problems in preparing for real-world physical actions is to use methods and system described herein for pre-action control of user-controllable images that enable user pre-action training control of output devices such as non-virtual robotic, prosthetic, powered orthotic, exoskeleton objects, other motile, motorized, or audiovisual output devices.

Further, the broad medical problem encompasses physical access to rehabilitative therapies. Rehabilitative facilities may be distanced from the user thereby requiring great effort and expense which may strain a user's abilities or resources or preclude access.

Further, the broad medical problem encompasses economic access to rehabilitative therapies. For example, a user's insurance may not include rehabilitative therapies or the user's insurance benefits for rehabilitative therapies may be insufficient or pre-maturely expended resulting in sub-optimal recovery.

One objective is to provide methods and system for enabling the user to instantiate kinetic imagery using simulations i.e. to transition from personal mental images or visualizations of physical actions into instantiations of simulated physical actions, synonymously, "viewable embodiments of cortical simulations of physical actions." One technical problem therefore is to construct user controllable images that are anatomically realistic, have analogous true range of motion, are user controllable to simulate physical actions on any display screen and thereby to provide the user with stimulating virtual alternatives to actual physical action feedback.

A further access-to-care problem is that an affected individual has insufficient methods and systems available to activate needed brain and nervous system processes, or to stimulate, much less repeatedly stimulate, without limitation, neurological structures such as neurons, neurological support cells, inter-neuron communications, gray and white matter cortical circuitry, brain areas such as, without limitation the prefrontal cortex, pre-motor cortex, supplementary cortex and motor cortex, other brain circuits or communications or tissues or proteins of the brain or central nervous system and contemporaneously or simultaneously activate by wired or wirelessly means at least one device attached to at least one human body part in need of rehabilitation, therapy or functional correction. The user's more particular medical, therapeutic, and rehabilitative care problems are to use methods and system described herein to improve the detriments/deficits noted above by controlling a virtual image(s) to simulate physical movements and movement actions and to actuate an attached or unattached body part device such that the device activates and/or stimulates one or more body parts. Actuation can be accomplished, for example, by wired or wireless means.

Existing science holds that repeated stimulation of neurological receptors may form "cell assemblies" and that beneficial mathematical relationships exist between outcomes of repeated firing of interconnected neurological cells and learned behavior. Using the methods and system described herein at least includes and provides for repeated, self-induced neuronal stimulation and self-teaching, including interactive instantiation of kinetic imagery.

The methods and system described herein enable negatively health-affected individuals e.g., the users, synonymously, "plurality of users," to use self-controlled and/or directed pre-action training simulations to stimulate brain structures and processes. Operationally, the user controls virtual body parts that are anatomically realistic with analogous true range of motion to simulate, synonymously, to create a copy of, or otherwise mimic physical actions, thereby engaging in pre-action gaming simulations. The use of this disclosure enables the user to repeat brain stimulation at least through interactive instantiation of kinetic imagery, synonymously, "viewable embodiments of cortical simulations of physical actions." The disclosure is directed without limitation to individuals affected by stroke, traumatic brain injury, focal dystonias, chronic traumatic encephalopathy, amputees, joint replacement patients, or other conditions in need of physical, occupational or psychological rehabilitation/therapy, without limitation, brain tumors, cerebral palsy, Parkinson's disease, autism spectrum disorders, schizophrenia, phobias, other acquired brain injuries ("ABI"), or other medical deficits, impairments, disorders or diseases.

Further operationally, before or without being able to perform physical action(s), the user executes inputs (using any input device e.g., without limitation a computer mouse, touch-screen, head or eye actions or wireless signals using an unimpaired motion without having to physically perform the action) that control/direct simulated physical actions of on-screen images. The user's physical method of inputs is physically non-corresponding to displayed actions of on-screen images. The inputs control virtual body parts whether clothed, skin-covered, or exposed, displayed in any virtual environment. The user inputs may simultaneously or sequentially control single or multiple virtual body parts.

Physiologically, the user's challenge is to initiate or improve physical or related cognitive actions before or without being able to perform or practice the actions. Using the present methods and system described herein stimulates survivors' brain and nervous system processes to perform purposeful movements by survivor's instantiating visual images of their abstract thoughts regarding purposeful physical movements and movement and actions. They control realistic virtual extremities that have analogous true range of motion to simulate physical purposeful movements and movement and actions (an inside-out process) and by wired or wireless means actuate at least one attached or unattached physical body part device such that the actuated physical body part device activates and/or stimulates one or more physical body parts. The methods and system described herein be used for self-teaching, without limitation: a) brain processes to enable performing new actions or improving past actions e.g., to help stroke or traumatic brain injury or chronic traumatic encephalopathy patients; or b) potentiation of brain processes to replace or supplement damaged neural circuits e.g., help joint-replacement patients regain abilities; or c) de-activation of existing neuromuscular actions, e.g., to decrease or stop users' uncontrolled muscle contractions as in focal cervical dystonia; or d) de-sensitization of damaged neural circuits e.g., phantom limb or other painful body parts; or e) creation of brain processes to supplant dysfunctional/debilitating experiences e.g., suffering from phobias, schizophrenic hallucinations or autism spectrum sensory-action disorders.

For individuals with disabled or dysfunctional use of body parts or with psychological conditions impeding control of actions or related cognitive processes, imagined action alone results in imagined feedback. Visualization and imagery alone, e.g., without creating pre-action simulations, are only somewhat sufficient for rehabilitating action planning or execution or for restoration of unaffected physical actions or related cognitive processes. The methods and system described herein provide video game-like, opportunities so that the user is able to transition from mere visualization to external feedback generation, i.e. to instantiate abstract mental representations of physical actions into actual visual displays of simulated physical actions, synonymously, "viewable embodiments of cortical simulations of physical actions." Using mental imagery is a skill many users have not developed to their fullest potential, as many non-users have not. Instantiation of mental visualization via the systems described herein re-enforces user's mental process and leverages the user's experience with overt, real-life imagery, albeit on a display screen.

Using the present disclosure, the user may attempt to create simulated physical actions and may succeed in doing so. Consequently, the user's planning processes for anticipated and intended physical actions and related cognitive processes are activated. This activation may be followed by controlling and/or directing desired, purposeful, simulated actions. Basically, the user anticipates or intends to originate or otherwise cause simulated physical actions and knows the meaning of such actions. Using the methods and system described herein, which include utilizing or creating instantiated kinetic imagery feedback, may help to illustrate and reinforce what the user planned to do and actually did. Repetition makes it possible to do that better.

The following presents a simplified summary of one or more aspects of the present disclosure in order to provide a basic understanding of such aspects. This summary is not an extensive overview of all contemplated aspects, and is intended neither to identify key or critical elements of all aspects nor to delineate the scope of any or all aspects. Its sole purpose is to present some concepts of one or more aspects in a simplified form as a prelude to the more detailed description that is presented later.

The one or more users of the present methods, systems, and devices described herein are able to transition from conscious imagery/visualization, in effect abstract mental processes, to real visuomotor feedback. Accordingly, for the affected conditions, injuries, disorders or experiences, or for any user who is challenged, the methods and system described herein enable instantiation of kinetic imagery, i.e.

"viewable embodiments of cortical simulations of physical actions" resulting in feedback that is next-best to actual physical action feedback for self-teaching, self-re-learning, self-re-exercising simulated physical actions or skills or related cognitive processes or self-administered-therapy-rehabilitation.

Aspects of the present disclosure relate to methods and systems for instantiating kinetic imagery. More particularly, the methods and system described herein includes instantiating kinetic imagery by a user controlling virtual body parts alone or in conjunction with virtual objects. In an aspect, a user may engage in one or more self-teaching virtual training games, i.e. Pre-action Exercise Games ("PEGs"), synonymously Pre-Action Games and Exercises (PAGEs). PEGs provide users with stimulating substitutes for actual physical action feedback. The feedback fosters stimulation aspects of any user's brain previously compromised due to any of the conditions or disorders listed in this disclosure or other conditions that may be within the scope of this disclosure. PEGs provide simulated physical action feedback from user controlled/directed virtual body parts corresponding or non-corresponding to the user's body part(s) that may have suffered reduced or lost functionality. The user, controlling virtual world actions, is engaged in virtual training for real-world actions. In an additional aspect, PEGs provide a user with a neuronal workout that stimulates without limitation neuronal recruitment, synaptogenesis and brain plasticity, functions or processes.

PEGs provide a link between kinetic visualization/imagery and user originated-controlled/directed simulated movements and physical actions. Visualization and imagery of physical action is an integral step in motor planning, physical performance or re-acquisition of purposeful physical actions that have been compromised. The methods and systems described herein implement kinetic imagery by providing each user with means to 'act out' or otherwise control virtual body parts so that the simulated actions of body parts represent instantiated, real visual displays of a user's abstract processes of visualization/imagery.

The present disclosure further relates to constructing, configuring, and/or controlling user controllable images, such as those used in pre-action training. According to aspects of the present disclosure, presented is a method of constructing a user-controllable image, which includes obtaining anatomical and physiological data associated with a model of the body, storing the data in a database, and creating the user-controllable image based on the body model data, wherein the user-controllable image may be configurable to a user, wherein at least a moveable portion of the user-controllable image is constructed to move based on input controls from a user, and wherein the user-controllable image is constructed so as to enable pre-action self-training by a user. In an additional aspect, demonstrative actions of the user-controllable image or any image(s) can be generated by using motion capture or other technologies. In an additional aspect, motion capture or other technologies can likewise be used to construct and/or configure a user controllable image.

In an additional aspect, presented herein is a method of configuring a user-controllable image to a user, which includes obtaining at least one default parameter associated with the user-controllable image, obtaining at least one user parameter associated with a user body, comparing the at least one default parameter and the at least one user parameter, constructing a user-configured, user-controllable image by adjusting one or more of the at least one default parameter where the at least one user parameter differs from the at least one default parameter, wherein the user-configured, user-controllable image is configured so as to enable pre-action self-training by a user, and providing the user-configured, user-controllable image to the user for pre-action training. In an additional aspect, motion capture or other technologies can likewise be used to construct and/or configure a user-controllable image ("UCI").

The present disclosure further provides an example method of controlling a user-controllable image, which includes providing a virtual body part to a user, wherein the user-controllable image comprises the virtual body part, receiving a selection input or multiple selection inputs from the user, wherein the selection input(s) is associated with at least a portion of one or more virtual body parts, receiving an action input from the user, and displaying an action of the at least a portion of the virtual body part based on the action input, wherein the displayed action is physically non-corresponding to the action input and wherein the selection input(s) and action input(s) are at least a part of pre-action self-training by a user. In addition, the methods and system described herein contemplate use of, without limitation, apparatuses, computers, computer readable media, handheld devices, computer program products, internet accessibility, multi-user use and means for performing these example methods.

The present disclosure further relates to methods and systems that provide for user pre-action training control of output devices such as non-virtual prostheses, exoskeleton body parts, powered orthotic devices, robots, or other motile or audiovisual output devices, synonymously, "at least one non-virtual object." This disclosure provides an example method for controlling a UCI representing the at least one non-virtual object. It includes providing a virtual representation of a non-virtual object to a user, wherein the representation of a non-virtual object receives a selection input(s) from the user, wherein the selection input is associated with at least a portion of the non-virtual object, wherein receiving an action(s) input from the user, and displaying, approximately simultaneously, the virtual action and a physical action of the at least a portion of the non-virtual object and based on the action input, wherein the virtual and physical actions are physically non-corresponding to the action input and wherein the selection input and action input are at least a part of pre-action training a user to use a non-virtual object.

Further aspects of the methods and system described herein relate to using pre-movement and action exercise games, or PEGs, for medical diagnostic purposes or measuring brain processes and biological substances, or biomarkers, to improve PEGs. In such further aspects a health-affected user, using PEGs, simultaneously has brain processes and biological substances assessed or measured, then compared to a baseline of control non-health-affected users who have used or are using PEGs.

Further aspects of the methods and system described herein relate to healthcare or research professionals learning or researching "what-ifs" relating to any of the conditions to which this disclosure is applicable.

The methods and system described herein may be non-invasive, solo video game-like, heuristic, economical and useable on any computer or other digital device, practically anywhere and at any time: essentially on user demand. The methods and system described herein have the potential to leverage users' rehabilitation or therapists' productivity to high levels. The methods and system described herein are well-suited to hands-on or telemedicine healthcare services.

In one embodiment of the present invention, a system for improvement of physical motor control of affected human extremities and related cognitive and nervous system processes includes a computer device having an input device and a display device each disposed in communication with the computer device. The computer device is configured to display to a user a virtual body part that represents a corresponding body part of the user requiring improvement. The virtual body part(s) optionally includes one or more selectable body part portions. The virtual body part or the selectable body part portion(s) is (are) shown in a first position or configuration on the display device. The computer device receives one or more user inputs that cause the virtual body part to move in a user-directed motion or a predefined motion. The computer device displays the predefined or user-directed motion of the virtual body part (and/or of the selectable body part portion) to a second position or configuration based on the user input. The user repeats the user input as necessary to cause improvement of physical motor control of the corresponding body part of the user and related cognitive and nervous system processes improvement.

In another embodiment of the system, the user input includes one or both of a selection input associated with the selectable body part and a movement and action input indicating the virtual movement in virtual 3D space of the body part.

In another embodiment of the system, the computer device is further configured to provide to the user an instruction to perform a task selected of moving the virtual body part in virtual 3D space, changing the position of the at least one selectable body part to a second position in virtual 3D space, interacting or moving an object in virtual 3D space, grasping a virtual object, touching a virtual object, aligning the virtual body part with a virtual object, positioning the virtual body part relative to a virtual reference point, using the virtual body part to select a virtual object, releasing an object, or rotating the virtual body part in virtual 3D space.

In another embodiment of the system, the computer device is further configured to provide to the user an instruction to perform a task of aligning the virtual body part with a displayed reference point, selecting one object among a plurality of displayed objects, or moving the at least one selectable body part to a displayed target.

In another embodiment of the system, the input device is configured to detect a biomarker or neurological signal of the user, correlate the biomarker or neurological signal to a movement and action associated with the virtual body part, and display to the user a virtual manifestation of the movement and action based on the biomarker or neurological signal.

In another embodiment of the system, the input device includes a user movement and action recognizing component configured to recognize a movement and action of the user.

In another embodiment of the system, the computer device is configured to display an indicia on the virtual body part or a portion thereof in response to the user input.

In another embodiment, the system includes a tangible body part device disposed in communication with the computer device, where the computer device is configured to output a control or actuation signal(s) to the tangible body part device based on user input. In one embodiment, the feedback device may be a tangible body part device disposed in communication with the computer device, where the tangible body part device may be actuated by a sound signal from the computer device.

In another embodiment, the system includes a feedback device disposed in communication with the computer device, wherein the feedback device provides feedback to the user based on the user input, where the feedback to the user is without limitation a sound or electrical signal coupled to or communicating with a muscle or nerve of the user, tactile feedback, visual feedback, audio feedback (including instruction, music, sound effects or other reward or encouragement), or an electrical or sound signal configured to control a tangible body part device disposed in communication with the computer device.

In an embodiment where the feedback is an electrical or sound signal configured to control a body part device, the tangible body part device is connected to the user. For example, the tangible body part device is operationally connected to the user. In another embodiment, the tangible body part device is not connected to the user. In another embodiment, the electrical or sound signal contemporaneously causes the body part device to substantially perform the movement of the virtual body part based on the user input.

In another embodiment of the system, the input device is configured to obtain a user measurement and compare the user measurement to a control value, where the user measurement is a neurological signal, a biological substance measurement, and/or a biomarker measurement.

In another embodiment of the system, the computer device is further configured to display to the user a demonstrative movement and action of the virtual body part, indicate to the user at least one virtual body part used to perform the demonstrative movement and action, instruct the user to mimic the demonstrative movement and action by entering at least one user selection, and receive the one user selection where the user selection(s) is (are) associated with the virtual body part used to perform the demonstrative movement and action.

In one embodiment, the viewable embodiments of cortical simulations of physical actions may be constructed as specialized computer digital multimedia packages capable of receiving and processing digital inputs and generating visual and/or audio outputs for display and/or presentation to a user via a digital device. In one aspect, the digital multimedia packages may be digital anatomical virtual extremities.

In one embodiment, methods and system described herein may include an external mechanical device configured to receive one or more control signals from computer device corresponding to the virtual movement of the digital multimedia packages being manipulated by the user. The external mechanical device may be attached to the user and may process the control signals to prompt movement of one or more body parts, which may include the user's affected body part.

Insert summary of new embodiments (after claims are drafted) and encompassing tele rehab embodiments.

To the accomplishment of the foregoing and related ends, the one or more aspects comprise the features hereinafter fully described and particularly pointed out in the claims. The detailed description of the methods and system described herein and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

FIGS. 23B-23C illustrate two views of portions of the tele-rehabilitation system of FIG. 16B.

FIG. 23D illustrates a standalone implementation of a system comprising a computer device configured with a left-hand glove body part device and a right-hand measurement glove device.

FIGS. 23E-23F illustrate additional views of portions of the tele-rehabilitation system of FIG. 16B.

FIG. 23G illustrates a standalone embodiment of a system comprising a computer device configured with a left-hand glove body part device, a right-hand measurement glove device and a virtual reality (VR) display headset device.

DETAILED DESCRIPTION OF THE INVENTION

Figure 1:
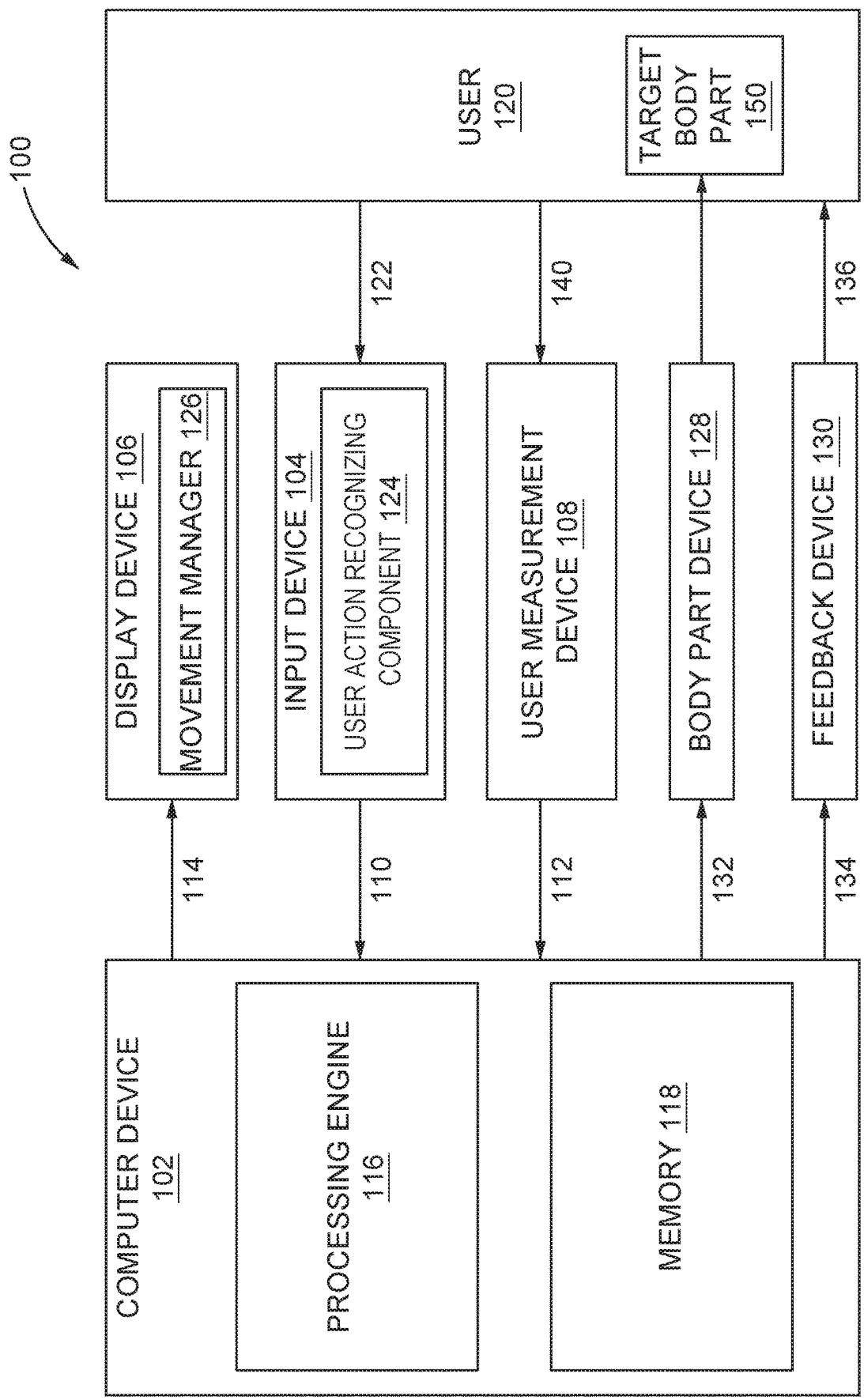
FIG. 1 is a system-level component diagram illustrating a system for pre-action training according to aspects of the present disclosure.

Purposeful and reflexive physical actions of body parts are proximally derived from neuronal signaling (spinal cord outputs) to muscles. However, pre-action planning for purposeful actions is derived from neuronal signaling (e.g., brain outputs) of structures or processes initiating the neural signaling of the spinal cord. Brain communications are essential to initiating purposeful new physical actions or to regaining ability to perform the physical actions or related cognitive processes or to correct physical, neurological or psychological actions associated with disorders or conditions.

The damaged brain, no less than other damaged body parts, requires therapy or rehabilitation. No known technologies, other than those described in this disclosure, are directed to pre-action planning, training, or exercises in virtual environments. None are known to enable users to instantiate kinetic images of physical actions in any virtual environment, i.e. to originate or create viewable embodiments of cortical simulations of physical actions.

Acquired brain injury ("ABI"), including stroke, chronic traumatic encephalopathy, and traumatic brain injury ("TBI") survivors, or without limitation, individuals affected by any condition, disorder, or experience noted in this disclosure, may sustain impaired or eradicated use of one or more body parts. The result is formation of mild to severe barriers to physically controlling one's actions. The barriers exist despite, in many instances, body parts being totally or somewhat uninjured. For ABI survivors it is fair to say that except for the brain injury (and consequential atrophy) chronic physical action deficits would not require rehabilitation. To address the deficits ABI survivors undergo long-term and costly therapeutic and rehabilitative procedures. These are major healthcare services or cost problems. Epidemiologically, and by way of example, the combined, annual incidence of ABI, stroke and traumatic brain injury ("TBI") alone, in the United States leaves 2.5 million survivors annually. A broader category, neurotrauma (penetrating and non-penetrating), including primary brain tumor, focal dystonias, limb apraxia/ataxia, cerebral palsy and amputations, affects more than 12 million U.S. civilians and approximately 200,000-400,000 combat veterans. Assuming that the incidence of ABI/TBI alone is generally uniform worldwide, by extrapolation the total number of ABI/TBI survivors worldwide would exceed 50 million individuals. The total number of neurotrauma survivors worldwide would therefore exceed 275 million individuals, which represents a number approximating the entire U.S. population.

Conventional rehabilitation/therapy for treating ABIs is primarily physical in nature involving assisted and independent efforts to restore survivors to being able to make unaffected physical actions. Physical and occupational therapy actions are characterized in that the movements of survivors' body parts correspond to intended unaffected movements. That recovery process is predominantly outside-in, i.e. body-to-brain. That is, the affected survivors' body part (e.g., an impaired extremity, synonymously impaired limb, impaired body part(s), impaired full body) may be externally physically manipulated with the intention (hope) of improving or restoring survivors' pre-injury unaffected movement. In contrast, the processes described herein are inside-out, i.e. brain-to-body. Methods and systems for pre-action training target brain structures or processes, i.e. a principal pathological site (synonymously lesion) for ABI/TBI survivors or other affected individuals. That is, the methods and systems described herein for pre-action training provide therapy targeted to the damaged brain with the intention of improving or restoring survivors' brain function and therefore improving or restoring survivor's pre-injury unaffected movement.

Making corresponding physical training movements are variably effective, but difficult or impossible for those recovering from ABI/TBI or other conditions or disorders noted above. From the survivors' perspective, the challenge and question are how to practice physical actions or train to move without being able to move. ABI/TBI survivors are left with disconnections between, on one hand, intact, and in many cases, initially uninjured body parts and on the other hand, dysfunctional brain processes required for planning the movements of such body parts. In some cases, patients' and survivors' difficulties are magnified due to the individual's non-awareness of the existence of an unusable body part. One challenge for ABI/TBI survivors is to regain the use of body parts. That challenge is addressed by using the methods and system herein to control virtual body parts so as to make simulated actions before, during, after or adjunctive to utilizing physical or assistive rehabilitation or therapeutic methods that use corresponding physical actions by such body parts. Thus to regain full and expeditious control of using ABI/TBI-affected body parts, the present methods and systems described herein may be utilized for providing pre-action training.

Conventionally for ABI, at least one of three therapies is used. They are, motor imagery; mirror therapy; and action-observation therapy. Motor imagery involves imagining motor controls and attempting to physically exercise the resulting imagery. Mirror therapy has been used for amputees experiencing phantom limb pain. It involves using an intact body part to make physical actions reflected in a physical mirror. The mirrored actions appear to be made by the contralateral (amputated) body part. The patient's observation of the actions has been shown to decrease or terminate phantom limb pain. Action-observation therapy is theoretically mirror neuron based and involves viewing physical actions followed by the patient's efforts to match, i.e. imitate the observed actions. None of the foregoing therapies are video game-like in terms of interactivity, immersion, scope, versatility, heuristic teaching methodology, economy, or entertainment. None enable patients to instantiate kinetic imagery. Unlike current therapies or rehabilitation, the disclosed techniques enable individuals, in a video game-like virtual environment, to independently make inputs that interactively control virtual body parts. By personally causing simulated physical actions to be displayed, the individuals produce real visuomotor (visuoaction) feedback from the simulated actions and induce new or augmented brain processes.

Humans excel at creating mental imagery. Imagery and simulation occur while conscious or during dreams. Conscious, imagined actions (e.g., pre-movement neuronal activity, pre-action neuronal activity, or pre-action planning) precede and are fundamental to making purposeful physical actions. Making repeated physical actions, accompanied by feedback acquired from such actions, results in improved action skills. For unaffected individuals, the process of creating productive feedback evolves from mental abstractions to making actual physical actions in the real world and receiving feedback via sensory-action return signals. That process is variably unavailable or impossible for many individuals affected by the aforementioned conditions. However, for the affected individuals the disclosed methods and system may be used to create productive action feedback directed to improving action planning and/or regaining physical actions for daily living.

Various aspects described herein relate to methods and systems for pre-action training (e.g., therapy or training directed to pre-action, synonymously planning, neuronal activity), also disclosed as pre-action training for ABI/TBI survivors. The term ABI/TBI survivors as used in this disclosure includes without limitation other conditions and disorders described in this disclosure and others to which pre-action training may be useful. More particularly, the methods and system herein are for pre-action training, synonymously planning, by ABI/TBI survivors using virtual body parts. In an aspect, a user, who may be an ABI/TBI survivor, may engage in one or more Pre-Action Exercise Games ("PEGs"). PEGs provide ABI/TBI survivors with brain stimulating substitutes for actual physical-action feedback. The PEG feedback fosters the user's restoration of pre-action brain processing, such as those parts of the brain previously compromised due to the ABI/TBI lesions. PEGs provide simulated physical-action feedback from user-originated physical simulations via controlled/directed, virtual body parts corresponding to at least the user's body parts that suffered reduced or lost functionality as the result of ABI or TBI. Such survivor controlled/directed, virtual body parts are caused by the user to simulate physical actions thereby executing virtual-world actions as pre-action training for real world actions. In an additional aspect, PEGs provide the ABI/TBI survivor with a pre-action training workout that stimulates, without limitation, neuronal recruitment, inter-neuron communication, neurogenesu(is), synaptogenesis, and brain plasticity.

PEGs provide a link between kinetic imagery/visualization and user-originated simulated physical actions. Imagery/visualization of physical actions is integral to action planning, physical performance, and reacquisition of physical actions or skills. The methods and systems described herein support kinetic visualization and imagery by providing each user with means to 'act out' or otherwise control virtual body parts so that the body parts represent real visual instantiations of a user's abstract processes of imagery/visualization.

PEGs are without limitation exercises used in pre-action control/direction of virtual body parts to simulate physical action intentions and at least to receive feedback for neuro-rehabilitation of action-planning processes.

According to aspects of the present disclosure, inter-movement and action with virtual body parts, links any user's cognition, visualization, or imagery to virtual action feedback. Furthermore, the methods and systems described herein can engage ABI/TBI survivors to self-teach action planning for purposeful physical actions.

According to aspects of the present disclosure, an ABI/TBI survivor may target and help overcome her/his action deficits by making inputs to a system that displays a user-controllable virtual body part, thereby directing and causing simulated actions of a moveable region of the virtual body part based on the inputs, viewing feedback from such simulated actions and building new and/or re-building impaired neurological or brain processes.

According to the present disclosure, any user may control and direct virtual body part(s) to display simulated, human physical actions with a virtual full range of motion. The user may control a virtual body part to speed up, slow down, stop or make any combination of the actions or gradations of same. System displays of virtual body part movements and actions may be idiosyncratic representations of each survivor's input controls and direction. In effect, the user's virtual body part control process stimulates cognitive processes and pre-movement and pre-action training for real action processes.

In an aspect, a computer device may control and display virtual movement of the virtual body part and may transmit one or more signals to a (tangible) body part device, which may stimulate one or more body parts of the user to move, for example, in a way that may correspond to the movement of the virtual body part. In some examples, the body part device may initiate body part movement by stimulating one or more receptors or triggers of the user's neurological system, which may in turn cause movement of the muscles, tendons, tissue, or any other part of the user's body.

Moreover, in an aspect, movement of impaired body parts may contribute to lessening blood clots due to deep vein thrombosis which can develop in certain medical conditions affecting how the blood clots. Blood clots may lead to further ischemic attacks (synonymously, strokes). Deep vein thrombosis can also develop when movement is unusually suspended such as after surgery or ABI or accident resulting in confinement to bed. Present modalities for prevention of blood clot development involve the prescribing of blood-thinning medications, which, intern, increase the risk of excessive bleeding upon unrelated bruising or injury. The present invention can be used to contribute to lessening or preventing the formation of blood clots, therefore lessening or preventing ischemic strokes by physical movement of the muscles, tendons, tissue, or any other part(s) of the user's body which is not capable of user-independent movement and a reduction in the use or blood thinning medications.

Furthermore, the methods and systems described herein differ from modern gaming systems like Wii™ and Kinect™ that are being used for physical and occupational rehabilitation. The systems require their users to make actual physical actions that are then displayed in virtual environments. Therefore, by design, Wii™ and Kinect™ users make actual physical actions that correspond to displayed actions. This does not preclude those gaming systems from being adopted and adapted for use according to the methods and systems herein. Conversely, the methods and systems described herein eliminate the requirement of user performance of corresponding physical actions to what are then displayed as simulated physical actions. For example, a user of the methods and system herein can make small or limited non-corresponding eye and/or head gestures carried by webcam signals, and wirelessly transmit brain signals, to control the simulated actions of virtual body parts. In but one example, any user's input signals by eye controls (alone) can direct a virtual shoulder to move an arm 90 degrees away from the virtual body. Accordingly, a user's input signaling processes associated with the methods and system herein are non-corresponding to the simulated movement and actions of the virtual body part. That is to say a user's physical method of input, e.g., movement of a wired or wireless mouse, or eye or head movements or transmission of a wired or wireless brain signal from the user, does not correspond to the simulated actions of the virtual body parts of the present disclosure.

The inputs (controls and directions) described herein are dissociated from displayed virtual-image actions and allow ABI/TBI survivors to cause simulated physical actions (action processes) before and without performing real physical training action processes. Each user's inputs according to the present disclosure are not physical-training action movements of the desired drill or skill. Rather, the present methods and systems target without limitation neuronal systems, brain structures, gray and white matter circuitry, neurogenesis, synaptogenesis, myelination, brain plasticity, and cognitive processes, not any particular physical-action inputs or outputs.

Physical training participation, due to its repetitive aspects, can be tedious and hindered by boredom. Participation in physical training is also fraught with new injury or aggravating old injury. PEGs provide entertaining, rewarding, and immersive features, including game sequence actions that result from a user's successful control, direction, and manipulation of virtual body parts and objects that also direct output devices such as non-virtual robots, powered orthotic device, prostheses or exoskeleton body parts.

For example, in terms of non-limiting and non-exclusive variations of research and investigation, as well as practical application, monitoring brain activity can enhance PEGs' pre-action training value. ABI/TBI survivors' brain activities or processes can be measured through any brain imaging technology or by analyzing blood and/or other body fluids, or biomarkers, or other substances for particular bio-chemicals, markers, and/or compounds related to without limitation overall brain cortical, or cognitive activity. Biomarkers include but are not limited to pulse rate, blood pressure, respiration rate, perspiration, body temperature, and eye dilation. Typically, biochemical levels and neurological signals may be measured or monitored to detect a spike or change in the level in response to an event or stress.

ABI/TBI survivors' baseline brain activities or processes could be determined before, during, and after PEGs training to measure changes accompanying PEGs training. For example, a signal peak, amplitude value, numerical value, concentration, timing of a signal, length of a signal, and other signal characteristics can be observed and compared with baseline values, threshold values, or ratios. Based on these observations, one may draw conclusions regarding the progress of the individual in restoring or improving a deficit or diagnose conditions, such as TBI, in a subject. Additionally, ABI/TBI survivors' brain activities or processes can be compared to non-ABI/TBI affected individuals undergoing or who underwent PEGs training activities to determine whether PEGs training is stimulating the same or similar affected parts of the ABI/TBI survivors' brains as are stimulated in the non-ABI/TBI affected individuals' brains. PEGs can be adjusted accordingly to enhance the brain activity or processes in the identified brain structures, processes or circuitry of the ABI/TBI survivors to match brain activities (including substance quantities, levels, and the like) of non-affected individuals' brain structures, processes or circuitry accompanying PEGs training. Other non-limiting and non-exclusive variations on the process are discussed below.

Data collection of user data measured at least in part in conjunction with PEGs training may be used with a machine learning based modeling engine to determine effective predictive relationships between user data, user therapeutic treatments and user treatment outcomes and thereby establish and maintain treatment protocols which model the relationship between inputs of user related data and therapeutic treatments and outputs of outcomes. Using treatment models, a treatment recommender engine may evaluate outcome predictions for a user and the user's associated user data over a various number of potential treatment regimens represented by treatment models and select and/or recommend optimal treatment strategies based at least in part on predicted outcomes. Additionally, such measured data can feedback to PEGs to adjust or attune to a user's current condition. Selections and/or recommendations may also be made based at least in part on cost and other constraints, such as a user's available time for treatment and access to treatment equipment.

PEGs can also be used as a non-invasive diagnostic tool. Some ABI/TBI survivors suffer mild brain injury, however current diagnostics are limited, comprising mostly subjective tests and some technical means. Additionally, while moderate to severe ABI/TBI is detectable through changes in brain morphology by CT-scans, MRI or other imaging technologies, mild ABI/TBI is difficult to detect or diagnose. Any survivor, who does not show severe or moderate TBI, could also be introduced to playing PEGs to monitor for mild ABI/TBI. Potentially mildly affected patients would play PEGs, and her/his brain activities would be compared to unaffected individuals' baseline brain activities to determine the comparative state or extent of mild injury or the possibility of unlikely or no detectable injury. PEGs may be used for assessing other levels of ABI/TBI, either solo or in conjunction with other methods or devices.

Various aspects are now described with reference to the drawings. In the following description, for purposes of explanation, numerous specific details are set forth in order to provide a thorough understanding of one or more aspects. It may be evident however, that such aspect(s) may be practiced without these specific details.

Turning to FIG. 1, a system 100 is presented for presentation and manipulation of a virtual body part as means for pre-action (synonymously pre-movement) training a user. In an aspect, system 100 may include a computer device 102, an input device 104, a display device 106, and a user measurement device 108. Additionally, system 100 may optionally include a body part device 128 and/or a feedback device 130. According to an aspect, computer device 102 may be configured to receive and process one or more user inputs 110 from input device 104, one or more user characteristics 112 from user measurement device 108, and may also be configured to generate and transmit one or more display control messages 114 to display device 106. In addition, computer device 102 may be configured to execute manipulation of a displayed virtual body part based on at least the inputs 104 of user 120. It should be appreciated that, in some implementations, computer device 102 of system 100 may support a plurality of users 120.

Furthermore, computer device 102 may include a processing engine 116, which may be configured to receive, process, and transmit signals associated with display, control, and/or behavior of a virtual body part. Additionally, computer device 102 may include a memory 118, which may be configured to store user characteristics (such as neurological or chemical characteristic values observed and/or measured from a user 120) and/or instructions for executing one or more PEGs.

In an aspect, input device 104 may be configured to receive one or more physical or non-physical inputs 122 from a user 120 and process and forward the processed physical inputs to computer device 102 as inputs 110. In an aspect, input device 104 may be any means of receiving direct physical input from a user 120, such as, but not limited to a keyboard, mouse, touch pad, touch screen, smart phone, laptop, computer or generic computing device, a microphone, an input device that senses input without intervention of the user, etc. In one example, input device 104 detects commands spoken by user 120. Alternatively, or additionally, input device 104 may be a device configured to generate input 110 by recognizing and processing one or more user actions at user action recognizing component 124, such as a movement detector, eyewear (e.g., Google glass), or headgear. For example, in an aspect, user action recognizing component 124 may be configured to recognize user inputs via, by non-limiting example, eye action, nominal physical action of hands or other body parts, blinking, nodding, and/or by detecting and monitoring neurological signals generated by the user's body. For example, user action recognizing component 124 may include a component capable of reading instructions signaled in the brain, spinal cord, or any other neurological circuit or tissue of the user 120.

Furthermore, display device 106 may be configured to display a virtual body part and actions of the virtual body part. In an aspect, display device 106 may display the virtual body part visually on a screen or display, such as, but not limited to, a computer monitor, projector, television, or the like). Alternatively, or additionally, external body part device 128 may receive one or more external body part control signals 132, which may cause the external body part device 128 to move, for example, by mechanical means. In an aspect, external body part device 128 may be, but is not limited to being, output devices such as a robotic arm, shoulder, prosthetic limb, a powered orthotic device, glove, sleeve, or sock, or the like. In some examples, the external body part device 128 may stand alone and be placed in a location viewable by the user 120. Additionally, the external body part device may be attached to the user 120, which may allow the user to witness more "true to life" actions associated with his or her physical inputs 122.

In an additional or alternative aspect, body part device 128 may be configured to receive one or more control signals from computer device 102 corresponding to the virtual movement of the virtual body part being manipulated by user 120. Based on the one or more control signals, the body part device 128 may process the control signals and stimulate one or more target body parts 150 of the user 120 (or of a non-user (not shown)) to prompt movement of one or more body parts, which may include target body part 150.

In yet another aspect, system 100 may include a feedback device 130 configured to provide feedback 136 to the user 120. In an aspect, feedback device 130 may receive one or more feedback control messages 134 related to the feedback device from computer device 102, which may govern the movement and action and behavior of the feedback device 130. In an aspect, feedback 136 may include, but is not limited to, force feedback, pneumatic feedback, auditory or visual feedback, non-force feedback, or any other form of feedback that may indicate an output of computer device 102 related to pre-action training. For non-limiting example, feedback device 130 may be a mechanical device that a user may attach to his or her hand or arm that may provide force feedback to the user's hand or arm in order to bend the user's wrist. In such an example, this bending may occur where the user selects a virtual wrist on display device 106 and moves the virtual wrist up and down (or in any direction) by moving input device 104. Based on this input, processing engine 116 may generate and transmit a feedback control message 136 to the feedback device 130 (here, the mechanical device) which may provide a force to the user's wrist to move it substantially in unison with the action of the virtual image, which may be displayed on display device 106 concurrently.

As another non-limiting example, feedback device 130 can be a haptic device (e.g., a haptic mouse, belt, vibration alert, electroactive polymer, piezoelectric wave actuator, electrostatic or subsonic audio wave actuation, or electrovibration) or an electrical feedback device in contact with the user (e.g., an electrode, conductive mat, conductive garment, etc.).

In an additional aspect, system 100 may include a user measurement device 108, which may be configured to measure one or more user characteristic values before, during, and/or after engaging in pre-action training activities. In some examples, user characteristic values may include without limitation neurological or chemical data, pulse, blood pressure, body temperature, pupillary dilation, perspiration, respiration rate, or any other measurable characteristic or physical parameter of an animal, which may include a human being. In an aspect, user measurement device may utilize imaging technology to measure these user characteristics, and such imaging technologies may include, without limitation, Magnetic Resonance Imaging (MRI), Functional Magnetic Resonance Imaging (fMRI), Computed Tomography (CT), Positron Emission Tomography (PET), Electroencephalography (EEG), Magnetoencephalography (MEG), Near-infrared spectroscopy (NIRS), and High Density Fiber Tracking (HDFT).

In a further aspect, user measurement device 108 may send the measured user characteristic data 112 to computer device 102 upon measurement. There, the user characteristic data may be (a) stored in memory 118 for later use or (b) fed to processing engine 116 as feedback data that processing engine 116 may utilize to alter an ongoing pre-action training activity, such as an ongoing PEG, or may be used to diagnose a medical condition. Alternatively, where the user characteristic data is stored in memory, such data may be used to tailor future pre-action training activities to the user's individual characteristics or current skill level or to track the progress of a user over time, or to improve PEGs.

Figure 2:
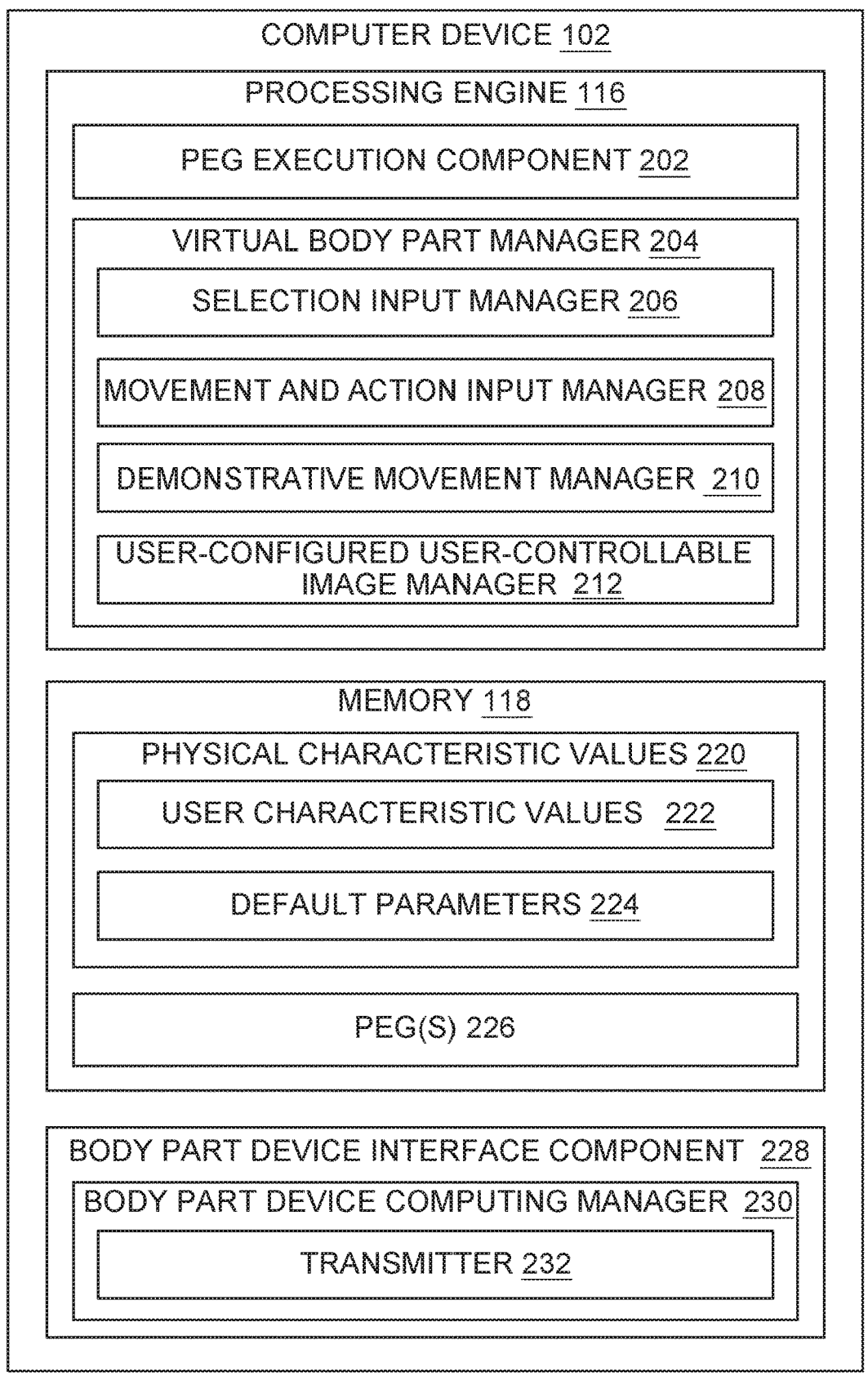
FIG. 2 is a component block diagram of aspects of a computer device for pre-action training according to aspects of the present disclosure.

Turning to FIG. 2, an illustration of components comprising computer device 102 (FIG. 1) is shown. In operation, computer device 102 may present an initial or default virtual body part to a user, for example, when the user, trainer, coach, therapist, or any other type of user initially boots up computer device 102, selects a PEG 226 for pre-action training activities, or the like. To display this default virtual body part, virtual body part manager 204 may query memory 118 for default parameters 224 of a set of physical characteristic values 220 stored thereon and may process and display the default virtual body part by sending, for example, one or more display control signals to a display. In addition, once the user begins a pre-action training session, computer device 102 may receive inputs from the user, such as, but not limited to, selection inputs and action inputs. Based on these one or more inputs and pre-stored and executable PEGs 226 located in memory 118, the computer device may present a selectable, movable, and otherwise interactive virtual body part with which a user may engage to partake in pre-action training activities.

As previously outlined, computer device 102 may include processing engine 116 and memory 118 (the operation and composition of which will be explained in reference to FIG. 2). First, processing engine 116 may be configured to process one or more input signals and transmit the processed signals to a display device for presentation of a user-controllable image, such as a virtual body part, to a user. For purposes of the present description, a user-controllable image (UCI) may be all or part of a virtual body part or object controllable by user input to simulate physical actions, wherein these physical actions are non-corresponding to the user's physical movements and actions in generating the user input. Examples of UCIs described herein may comprise a virtual body part(s), but the scope of such examples should not be limited thereto.

In an aspect, processing engine 116 may include a PEG execution component 202, which may process user inputs to generate display control messages according to instructions related to one or more PEGs. In a non-limiting example, a user may select a particular PEG to play and as a result, PEG execution component 202 may load the PEG instructions from PEGs 226 stored in memory 118. After loading the PEG, the PEG execution component 202 may generate one or more display control messages for transmission to a display device based on the PEG and any input messages received from an input device. Furthermore, in an aspect, PEG execution component 202 may be configured to alter one or more PEGs based on feedback from a user measurement device. In a non-limiting example, PEG execution component 202 may receive an indication that a user's neurological system is stronger than in the past and may make playing a particular PEG more difficult to maximize further neurological improvement.

In an additional aspect, processing engine 116 may include a virtual body part manager 204, which may be configured to virtually construct and manage action of a virtual body part that computer device 102 may generate for display on a display device. Furthermore, for purposes of the present description, the term "display device" may correspond to any output device, e.g., display device 106, body part device 128, feedback device 130, or any other device or means capable of producing output corresponding to an action, and/or status of a virtual body part, including output resulting from user input during pre-action training activities.

In an aspect, virtual body part manager 204 may include a selection input managing component 206, which may be configured to receive one or more selection inputs from a user or an input device manipulated by a user, wherein the selection inputs may correspond to a user selecting a virtual body part or a portion thereof. Furthermore, based on a selection input, selection input manager 206 may map a select location associated with a selection input to a virtual body part or a portion thereof, which may correspond to a virtual body part selected for subsequent or concurrent action by the user.

Furthermore, virtual body part manager 204 may include a movement and action input manager 208, which may be configured to receive one or more movement and action inputs from a user and generate one or more display control signals that cause displayed movement and action of the virtual body part. In an aspect, this displayed action may correspond to the virtual body part or portion thereof selected by the user and mapped by selection input manager 106. Additionally, movement and action input component 208 may generate and display the displayed action based on the user "dragging" "pointing" "tapping" "touching" or otherwise correctly manipulating at least a portion of the virtual body part that is movable in virtual 3D space.

Furthermore, action input component 208 may base its virtual body part movement and action generation and/or other processing actions on a particular PEG, which may have been pre-selected by a user and loaded for execution by processing engine 116. In an aspect, a movement and action input may be input by a user and received by computer device 102 as a result of the user partaking in such a PEG, other pre-action training activity, or any other pre-action training activity.

Additionally, in an aspect of the present disclosure, a user input movement and action may be physically non-corresponding to the desired or eventual action of the displayed virtual body part with which the user is interacting. For purposes of the present disclosure, a non-corresponding movement and action may be a user action that differs relatively significantly from a displayed movement and action by the virtual body part.

For non-limiting example, suppose a user engaged in a pre-action training activity wishes to move a virtual forearm directly upward using a mouse as an input device. To do so, according to aspects of the disclosure, the user may first navigate a cursor and click a mouse button to select the virtual forearm on a display device, thereby inputting a selection input. Next, the user may keep the cursor on the virtual forearm and may hold the mouse button down to signal a beginning of an action input. Thereafter, the user may drag the mouse two inches along a mouse pad, with the mouse button held down, and may observe the virtual forearm rise upward, for example, from a virtual hip area to a virtual head area. To carry out this action, the user's physical forearm may have moved approximately two inches in a direction parallel (e.g., horizontally) to the mouse pad, but resulted in a virtual action of the virtual forearm that was upward in direction and appeared greater than two inches in magnitude. Therefore, this example user input action is non-corresponding to the action of the virtual body part.

Additionally, virtual body part manager 204 may include a demonstrative action manager 210, which may be configured to provide display control messages to a display device to effectuate a demonstrative action of the virtual body part. For example, demonstrative action manager 210 may store and/or execute a retrieved demonstrative action to be displayed to the user as a "ghost" action. In an aspect, the user may view the demonstrative action and may then attempt to manipulate the virtual body part to mimic the action of the demonstrative action or ghost action.

Furthermore, virtual body part manager 204 may include a user-configured UCI manager 212, which may tailor or otherwise configure a displayed virtual body part to a user's body and/or alter the behavior of the displayed virtual body part based on one or more user characteristic values 222. In an aspect, such characteristics may include anatomical and physiological data characteristic values associated with the user, such as without limitation height, weight, arm length, muscle mass, TBI-affected body parts, handedness, age, gender, eye/hair/skin color, and the like. In additional or alternative aspects, the user characteristics may include historical PEG performance data associated with the user, current neurological or chemical measurement characteristics or parameter values, or the like.

In an aspect, user-configured UCI manager 212 may obtain these user characteristic values 222 from memory 118. Alternatively, user-configured UCI manager 212 may obtain these user characteristic values from a source external to memory 118, such as, but not limited to, a user measurement device configured to measure neurological and/or chemical characteristics of the user during pre-action training activities, by querying a user or the user's trainer, doctor, coach, therapist or rehabilitation specialist for such characteristic values and receiving a characteristic value input in response, or otherwise receiving user-specific performance, anatomical, physiological, or other characteristic values. In another aspect, UCI manager 212 obtains user characteristic values 222 by using anatomy recognition software known in the art, such as WII™ or Kinect™, capable of detecting and identifying body parts and characteristics of human anatomical features.

In addition, user-configured UCI manager 212 may be configured to compare the user characteristic values, or user parameters, to one or more default parameters 224 stored in memory 118. In an aspect, default parameters 224 may comprise the parameters of a default virtual body part of the present disclosure and may include without limitation anatomical and physiological data (e.g., handedness, strength, bone length, limitations on range of motion, skin characteristics, and the like). Such characteristics may conform the behavior and attributes of the default virtual body part displayed to a user before tailoring, configuring, or otherwise customizing the virtual body part to the user. In order to perform such customization, the user-configured UCI manager 212 may compare the obtained user characteristic values (e.g., user characteristic values 222) to default parameters 224. In an aspect, where the comparing determines that a user characteristic value differs from the default parameter value for a characteristic, the user-configured UCI manager may set the compared parameter of the virtual body part to be displayed to the user's characteristic value. Alternatively, where an obtained user characteristic value does not differ from the default parameter, user-configured UCI manager 212 may leave the compared parameter unchanged.

In an additional aspect, processing engine 116 may be configured to generate and/or transmit one or more display control signals to the display device to effectuate action of the virtual body part. Furthermore, processing engine 116 may be additionally configured to calculate and/or report an action degree or action magnitude associated with an action of the virtual body part. In an aspect, processing engine 116 may display the calculated action degree or action magnitude by generating one or more display control messages, which may be generated and transmitted in substantially real time, for transmission to a display device for visual indication of the action degree to the user.

Furthermore, computer device 102 may include a memory 118, which may be configured to store information for utilization by other components in a system, such as, but not limited to, processing engine 116. Such information may include physical characteristic values 220, which may include user characteristic values 222 associated with one or more users and/or default parameters 224 associated with a baseline or default UCI, such as a virtual body part. Furthermore, memory 118 may store neurological, chemical, or any other data related to a user's body (e.g., without limitation neurological signaling data or maps, neuron activity data, etc.) generated and/or observed by a user measurement device before, during, and/or after a user engaging in pre-action training. Such data may also be fed back to processing engine 116, which may alter a current or future PEG or pre-action training activity based on the feedback.

In an additional aspect, such user data may be used to diagnose one or more medical conditions. For example, computer device may output the user data to a physician or other professional, who may analyze the data and diagnose the medical condition. In an alternative or additional and non-limiting example, computer device 102 may contain instructions executable by processing engine 116 to automatically diagnose a medical condition based on the user data stored on memory 118 and may output the diagnosis to a physician or other professional.

In addition, memory 118 may include executable instructions (e.g., executed by processing engine 116), that when performed, allow the user to engage in one or more pre-action training activities. As used herein, pre-action training activities may include interactive electronic games or activities, such as, but not limited to, Pre-Action Exercise Games (PEGs) 226. The PEGs 226 may govern the behavior of a virtual body part in response to one or more inputs by a user during pre-action training activities.

Additionally, cognitive and nervous system functions are involved in all PEGs. According to some example PEGs, virtual upper body parts are presented to a user to control in order to simulate purposeful physical movements and actions such as, for example, opening and closing a virtual hand. Some PEGs may be virtual task games, which may couple player control of virtual body parts and objects to accomplish tasks and/or solve problems such as, for example, dropping a spoon into a cup.

Furthermore, in an aspect, PEGs may include player control of any part or all of an affected hand, lower or upper arm (right or left), executing flexion/extension, supination/pronation, abduction/adduction, or any other extremity or body part action in any direction. According to the PEGs contemplated herein, users can manage displays of some of, the majority of, or all of a virtual upper extremity from substantially any angle. Additionally, the virtual body part may comprise fingers, which may be manipulated individually or in combination. The virtual body part may comprise a wrist, which may be flexed/extended, abducted/adducted, or supinated/pronated. Furthermore, according to some non-limiting example PEGs, the virtual body part may comprise an arm, wherein the lower and upper arm may be manipulated independently or in combined action of any and all joints of the arm, wrist and hand. It should be appreciated that other non-limiting aspects of PEGS may target non-upper extremities.

In some non-limiting example PEGs, where the virtual body part is a virtual hand, example games for pre-action training may include:

pincer action to grasp a key;

two finger actions to grasp a ball and drop it into a cup;

multi-finger action to pick up a spoon and drop it into a cup;

full hand grasp around a mug handle;

tapping actions by index and middle fingers on a remote controller;

hand grasps of objects shaped as stars, circles or squares, then placement in similarly shaped slots.

Regarding virtual body parts in some non-limiting example PEGs where the virtual body part includes a virtual arm and/or a virtual hand, example games for pre-action training may include:

opening a correct box, i.e. selecting and opening the correct numbered and colored box (e.g., purple 24) in a circle of nine boxes, after observations and computations as elementary as choosing the (single) "lowest purple box bearing an even number" (purple 24 is correct) to computations based on several numbered boxes, e.g., "choose the highest blue even numbered box, subtract the second of its numbers from the first, square it and find the green box with that result" (if 92 blue is selected the subtraction yields number 7, which when squared is 49, so green box 49 is correct);

same as above, nine box game with voice instructions to the player;

similar open the box game in a more elementary vertical presentation of five boxes;

light bulb game requiring the player to unscrew a light bulb, choose the correct lettered socket and screw the bulb into the correct socket;

playing card games, for example in a simple game the virtual arm and hand are controlled to select a pair of twos, place that pair, right side up on a surface, then the player must choose the lowest numbered pair that wins over a pair of twos, alternately the highest numbered pair that wins over twos, then the lowest (or highest) pair of picture cards that wins over twos and so forth, to more complex combinations of playing cards/hands;

puzzle games in which the cursor may be used to move 6, 9 or 16 puzzle pieces to assemble a complete representation of any display noted above. For example, a hand image, in any orientation, position and configuration may be disassembled by the puzzle game into 6, 9 or 16 puzzle pieces to be reassembled by the player, or a more complex disassembly of the nine box arm game may be "puzzled";

simple number game displaying 0-9 and processes (add, subtract, multiply, divide and equals sign) and calling for the PEGs player to use a virtual arm and hand to select numbers and processes and to make any number of computations by arraying the numbers and processes accurately;

simple letter game displaying all letters of the alphabet and calling for the PEGs player to use a virtual arm and hand to select letters to make any number of words by arraying the letters accurately.

It should be appreciated that system 100 may utilize and display any suitable pre-action exercise game the above example games are merely exemplary and not limiting. Where the virtual body part is at least one virtual muscle, games for pre-movement and action training may include selection of the at least one virtual muscle to cause it to contract or relax at any rate of speed or to stop, for non-limiting example to end cramping or focal cervical dystonia or to regain movement impeded by hand dystonia. Therefore by loading and/or executing the one or more stored PEGs 226 of memory 118, computer device 102 may present a user with a UCI, such as a virtual body part, with which the user may interact to participate in pre-action training activities.

In a further aspect, computer device 102 may include a body part device interface component 228, which may be configured to interface with an external (or integrated) body part device 128, generate one or more control signals based on the user control of the virtual body part, or UCI, and transmit the one or more control signals to the body part device 128 of FIG. 1 for eventual stimulation of a target body part 150. In some examples, body part device interface component 228 may include a body part device computing manager 230 which may generate the one or more control signals based on the user control of the virtual body part. In a further aspect, the body part device computing manager 230 may include a transmitter 232, which may be communicatively coupled to the body part device 128 via a communicative connection and may be configured to transmit the one or more control signals to the body part device 128. In some examples, the transmitter 232 may transmit the signals wirelessly or via a transmission line, depending on whether the computer device 102 is tethered to the body part device 128 via a transmission line, such as a bus or other wire. For example, where the computer device 102 is connected to the body part device 128, the transmitter may be configured to transmit the control signals over the transmission line (though it may also transmit the control signals wirelessly as well). Alternatively, where the computer device 102 is not tethered to the body part device, the transmitter 232 may transmit the one or more control signals wirelessly. As such, transmitter 232 may comprise one or more antennas or transceivers.

Figure 3:
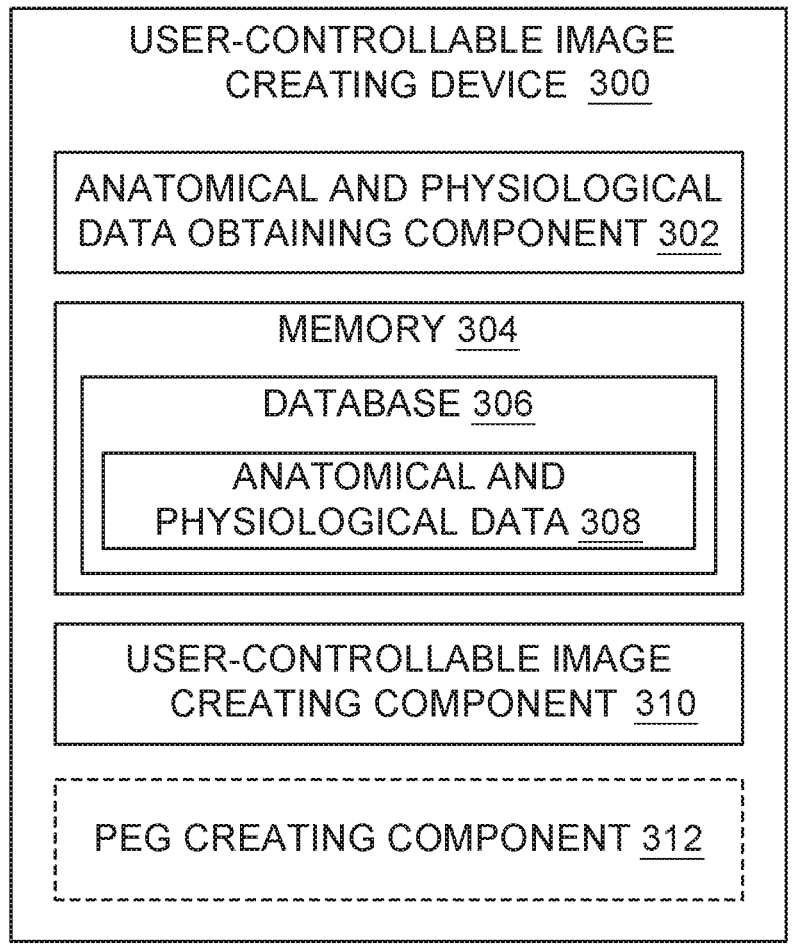
FIG. 3 is a component block diagram of aspects of a UCI constructing device according to aspects of the present disclosure.

Turning to FIG. 3, the figure illustrates an example UCI creating device 300 that facilitates creation of UCIs, including one or more virtual body parts. In an aspect, UCI creating device 300 may include an anatomical and physiological data obtaining component 302, which may be configured to obtain anatomical and physiological data associated with one or more animal species, including, but not limited to, human beings. Such anatomical and physiological data may be accurate or relatively accurate anatomical and physiological data to ensure that a relatively life-like UCI may be created therefrom. In a non-limiting example, anatomical and physiological data obtaining component 302 may be configured to interface, communicate with, read, extract data from, or obtain data from an external device or component that contains such anatomical and physiological data, such as, but not limited to a server, a device connected to a network (e.g the Internet), a wireless device, or a device connected to UCI creating device by hard wire communication line. In an additional aspect, anatomical and physiological data obtaining component 302 may be configured to prompt a user to manually input anatomical and physiological data and receive such data from a user via an input device such as, but not limited to, a keyboard.

Additionally, UCI creating device 300 may include a memory 304, which may include one or more databases 306 for storing and organizing data. In an aspect, database 306 may store anatomical and physiological data 308, which may have been obtained via anatomical and physiological data obtaining component 302.

Furthermore, UCI creating device 300 may include a UCI creating component 310, which may be configured to receive one or more inputs, such as, but not limited to program instructions, from a user (e.g., UCI architect, programmer, graphic designer), wherein the inputs, when executed, construct a UCI. In an aspect, the received inputs may construct the UCI based on the stored anatomical and physiological data 308. Furthermore, UCI creating component may include an executable program, such as an image design program, graphics creation suite, programming/compiling engine, or rendering suite, which UCI creating component 310 may execute to receive the one or more inputs from the user. These one or more inputs may define the physical parameters of the UCI, such as, but not limited to the bone length, bone interaction and position, tendon length and position, skin tone, and the like. Furthermore, the inputs may form computer-executable instructions that define and/or otherwise control the behavior of the UCI or portions of the UCI when executed, displayed, and interacted with by a user, for example, during pre-action training such as when playing a PEG. In addition, inputs may define the behavior of virtual body parts adjacent to the selected or moved body parts such that action of one virtual body part or portion thereof causes related action of the adjacent virtual body part or a portion thereof.

Moreover, UCI creating device 300 may include a PEG creating component 312, which may be configured to create one or more PEGs by receiving one or more inputs, such as, but not limited to program instructions, from a user (e.g., PEG architect, programmer), wherein the inputs, when executed, construct a PEG. The created PEG may be created for purposes of pre-action training and may be programmed to alter the behavior of a UCI, such as a virtual body part, based upon user inputs. Furthermore, the PEG may be programmed to customize or tailor a PEG based on unique characteristic data associated with the user, such as, but not limited to, height, weight, historical PEG performance, handedness, extremity length, and the like.

Figure 4:
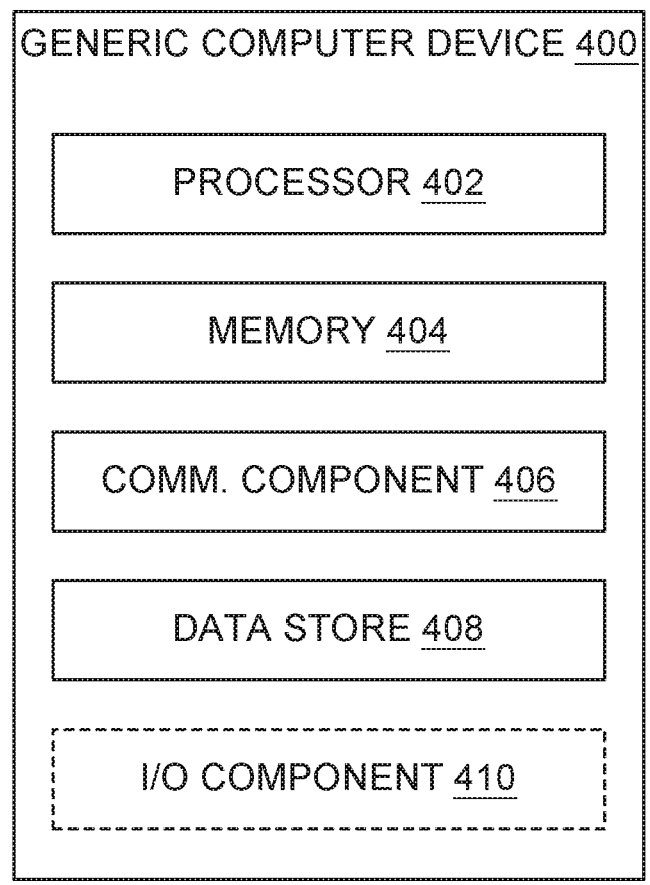
FIG. 4 is a component block diagram of aspects of a computer device according to aspects of the present disclosure.

Referring to FIG. 4, in one aspect, generic computer device 400 may include a specially programmed or configured computer device, and may represent or contain components that may be included in computer device 102 FIGS. 1 and 2) or UCI creating device 300 (FIG. 3) or body part device 128. Generic computer device 400 includes a processor 402 for carrying out processing processes associated with one or more of components and processes described herein. Processor 402 can include a single or multiple set of processors or multi-core processors. Moreover, processor 402 can be implemented as an integrated processing system and/or a distributed processing system. Additionally, processor 402 may be configured to perform the processes described herein related to UCI behavior and/or pre-action training on the generic computer device 400.

Generic computer device 400 further includes a memory 404, such as for storing data used herein and/or local versions of applications being executed by processor 402. Memory 404 can include any type of internal or external memory usable by a computer, such as random access memory (RAM), read only memory (ROM), tapes, magnetic discs, optical discs, volatile memory, non-volatile memory, and any combination thereof. Additionally, memory 404 may be configured to store data and/or code or computer-readable instructions for performing the processes described herein related to creating, controlling, manipulating, and/or instantiating a UCI.

Further, generic computer device 400 includes a communications component 406 that provides for establishing and maintaining communications with one or more entities utilizing one or more of hardware, software, and services as described herein. Communications component 406 may carry communication signals between components on generic computer device 400, as well as exchanging communication signals between generic computer device 400 and external devices, such as devices located across a wired or wireless communications network and/or devices serially or locally connected to generic computer device 400. For example, communications component 406 may include one or more buses, and may further include transmit chain components and receive chain components associated with a transmitter and receiver, respectively, or a transceiver, operable for interfacing with external devices.

Additionally, generic computer device 400 may further include a data store 408, which can be any suitable combination of hardware and/or software, that provides for mass storage of information, databases, and programs employed in connection with aspects described herein. For example, data store 408 may be a data repository for applications and data not currently being executed by processor 402, such as those related to the aspect described herein. In addition, generic computer device 400 may contain an input/output component 410, which may be configured to interface with one or more external devices, such as an input device (e.g., input device, user measurement device (FIG. 1)) and/or an output device (e.g., a display, feedback device, or external body part device (FIG. 1)). Specifically, input/output component 410 may contain circuitry and/or instructions that allow generic computer device 400 to connect to and/or communicate with these external devices.

Figure 5:
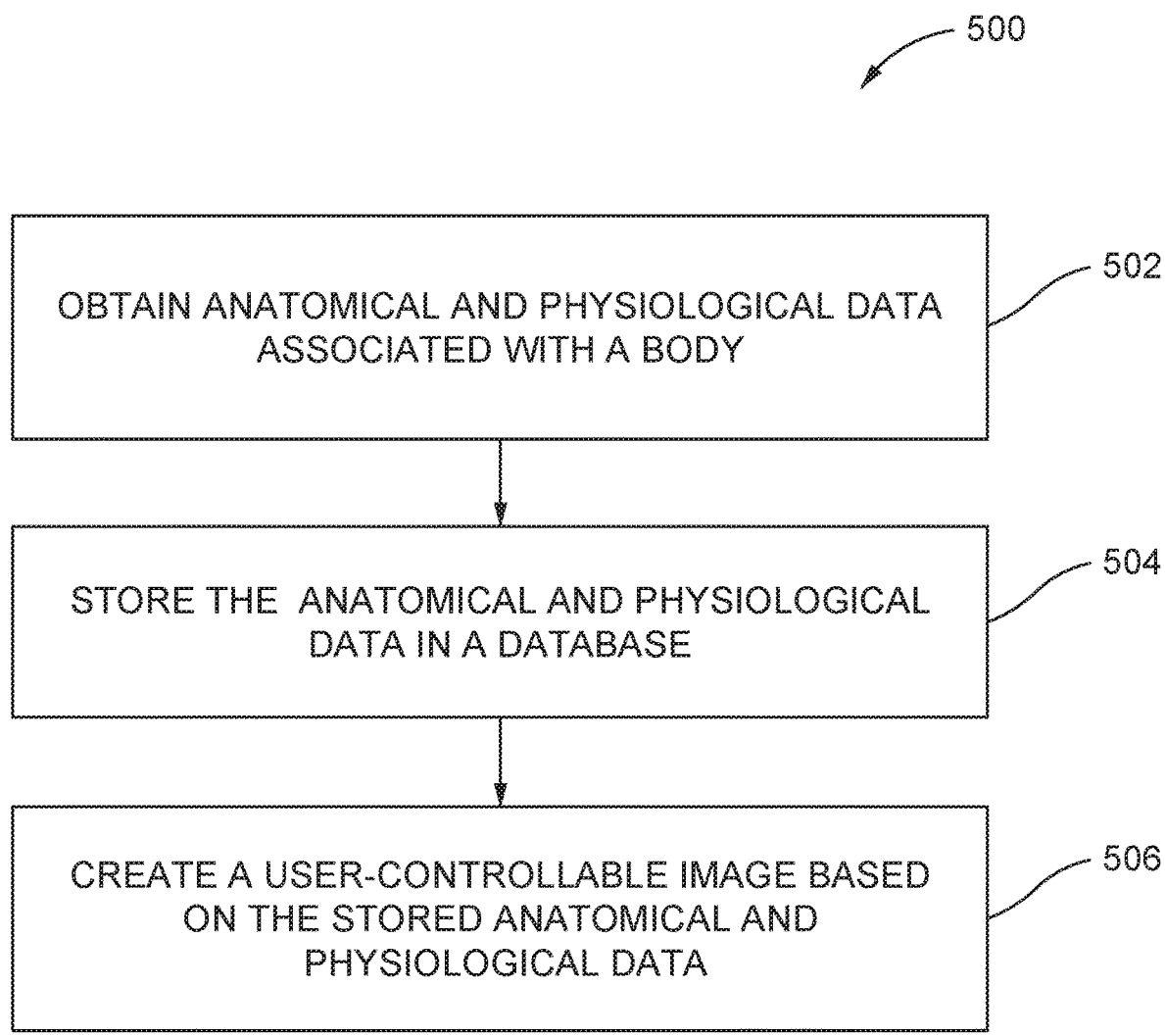
FIG. 5 is a flow diagram illustrating aspects of an example method of constructing a UCI according to the present disclosure.

In reference to FIG. 5, illustrated is an example methodology 500 for creating or otherwise constructing a user-controllable image, such as a virtual body part. In an aspect, at block 502, a user (e.g., a program engineer, user, or graphics engineer) or computer device may obtain anatomical and physiological data associated with a body. Once obtained, at block 504, the user or computer device may store the anatomical and physiological data in a database. In addition, at block 506, the user or computer device may create the user-controllable image based on the stored anatomical and physiological data. Furthermore, the created user-controllable image may be configurable to a user. Additionally, according to some example methods, at least a moveable portion of the user-controllable image may be constructed to move based on input from a user, for example, so as to enable pre-action training the user.

Figure 6:
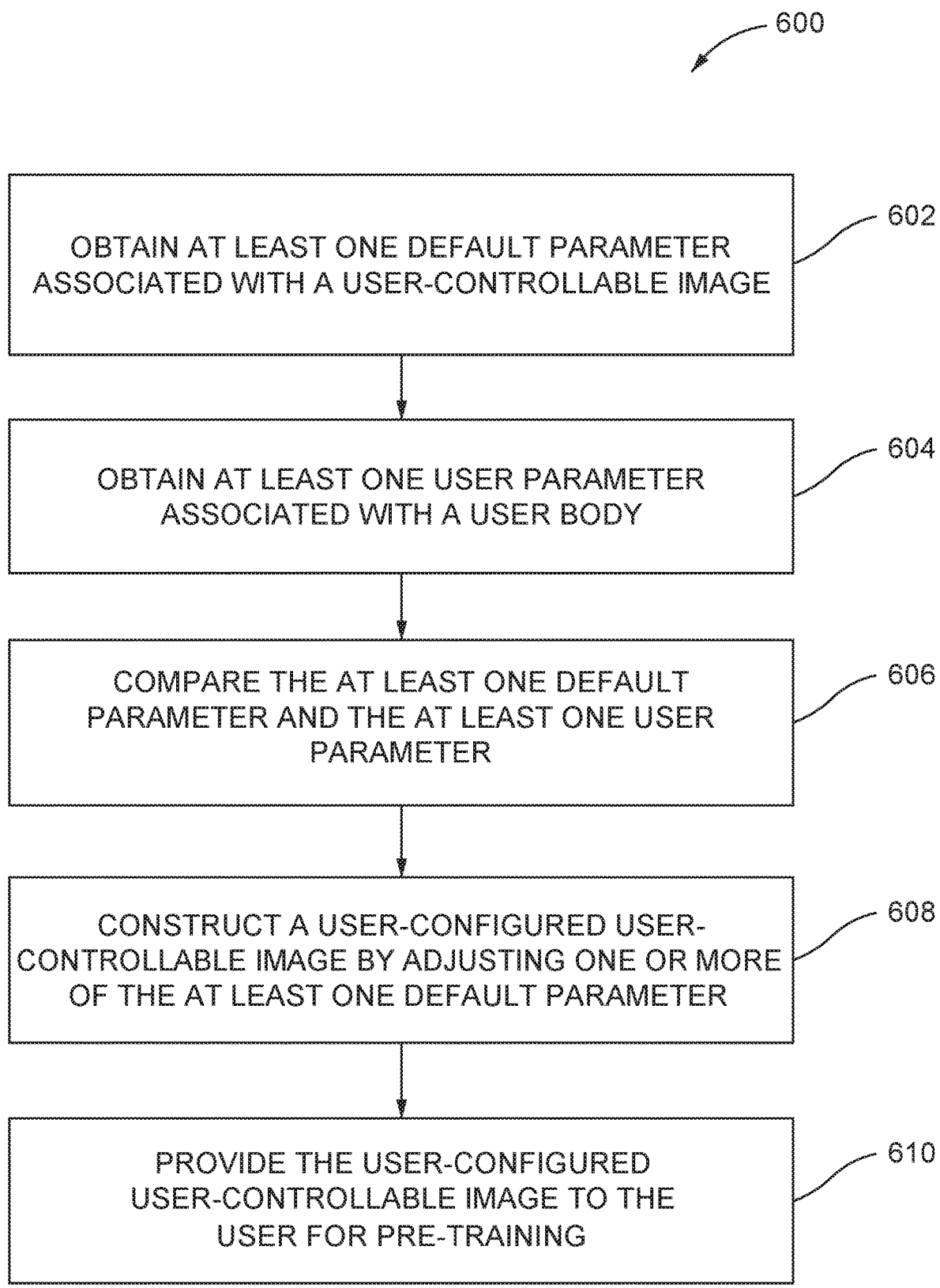
FIG. 6 is a flow diagram illustrating aspects of an example method of configuring a UCI to a user according to the present disclosure.

Furthermore, FIG. 6 presents an example methodology 600 for configuring, tailoring, or otherwise customizing a UCI or related PEG to a particular user. Such a method may be performed by a computer device, but may also be performed or controlled via a computer device by an individual, e.g., a pre-action training coach, therapist, or doctor, who may guide a user through a pre-action training regimen. In an aspect, at block 602, the individual or computer device may obtain at least one default parameter associated with the user-controllable image. In addition, at block 604, the individual or computer device may obtain at least one user parameter associated with a user body. Furthermore, at block 606, the individual or computer device may compare the at least one default parameter and the at least one user parameter. Moreover, the individual or computer device may construct a user-configured user-controllable image by adjusting one or more of the at least one default parameter. In an aspect, such an adjustment may be made where the at least one user parameter differs from the at least one default parameter. Additionally, the user-configured user-controllable image may be configured so as to enable pre-training a user, and as such, at block 610, the individual or computer device may provide the user-configured user-controllable image to the user for pre-action training.

Figure 7:
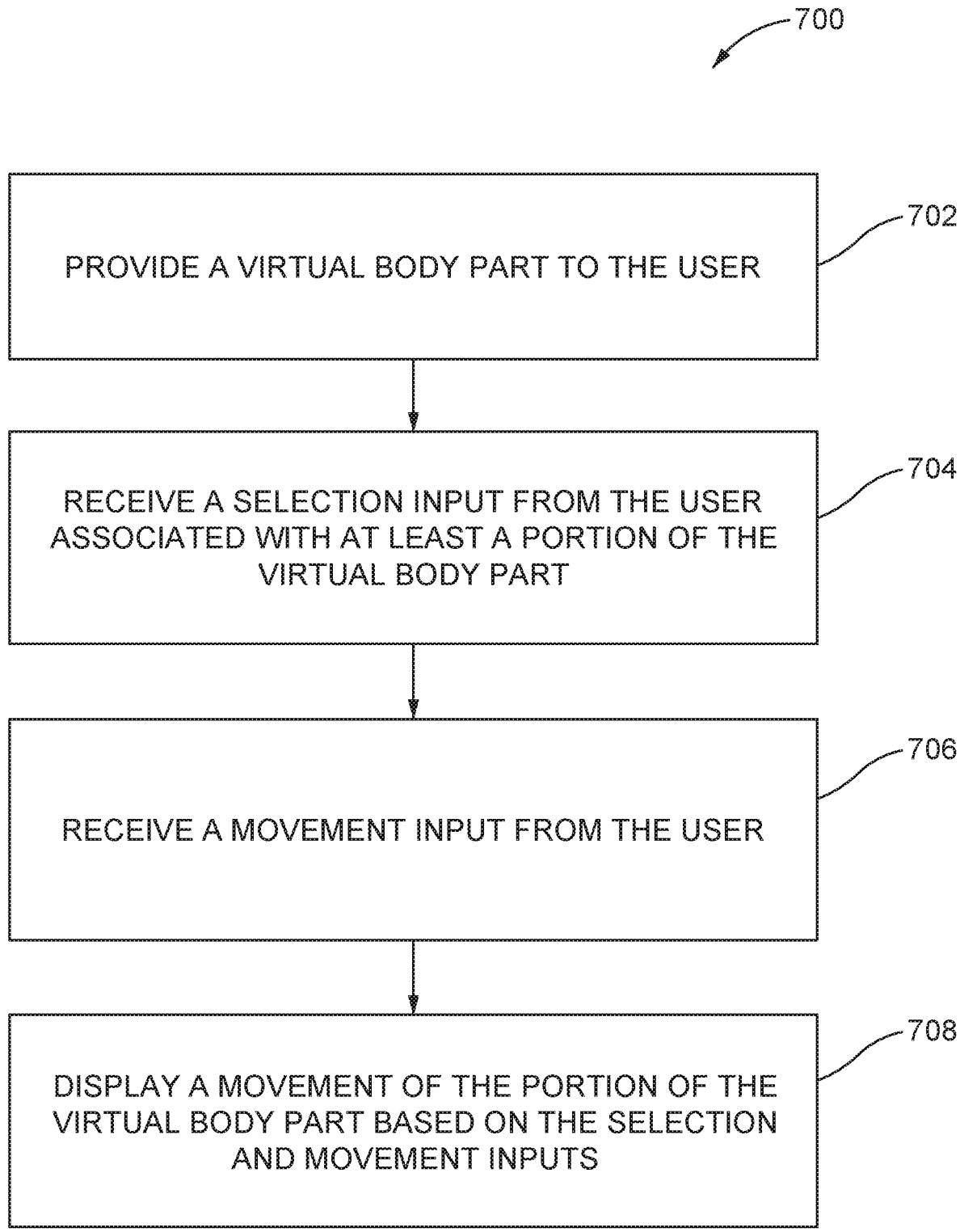
FIG. 7 is a flow diagram illustrating aspects of an example method of providing pre-action training activities to a user according to the present disclosure.

Turning to FIG. 7, an example methodology 700 is presented for presenting a controllable virtual body part to a user. In an aspect, at block 702, a computer device may provide a virtual body part to a user. Furthermore, at block 704, the computer device may receive a selection input from the user, wherein the selection input may be associated with at least a portion of the virtual body part. Additionally, at block 706, the computer device may receive an action input from the user. Furthermore, at block 708, the computer device may cause the display of an action of the at least a portion of the virtual body part based on the action input. In an additional aspect, the action may be physically non-corresponding to the action input. Furthermore, the selection input and action input may be at least a part of pre-training a user.

Figure 8:
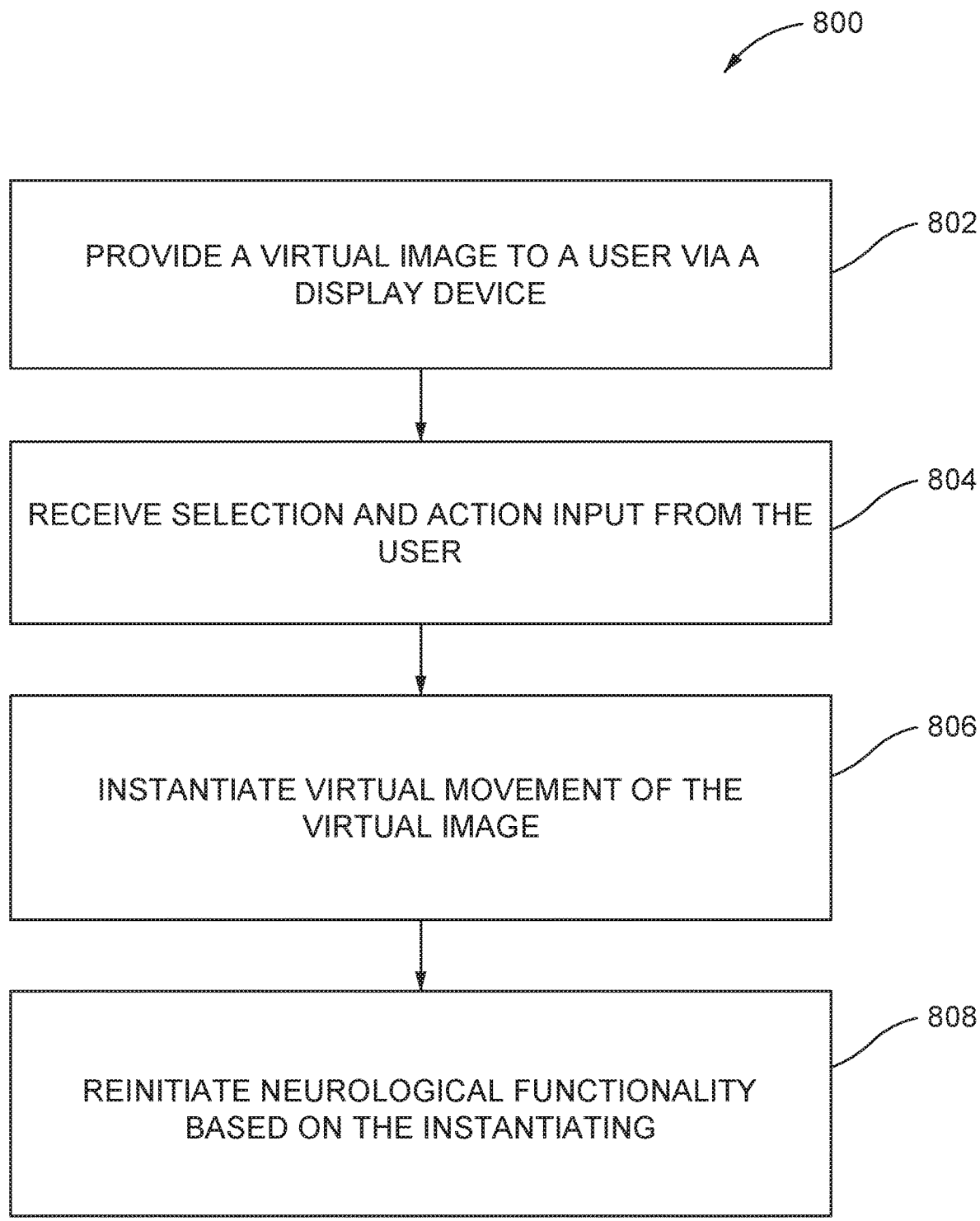
FIG. 8 is a flow diagram illustrating aspects of an example method of instantiating a virtual movement and reinitiating neurological functionality according to the present disclosure

Turning to FIG. 8, an example methodology 800 is presented for presenting a controllable virtual body part to a user. In an aspect, at block 802, a computer device may provide a virtual body part to a user via a display device. Furthermore, at block 804, the computer device may receive a selection input and an action input from the user. In some aspects, the selection input and the action input may be associated with at least a portion of the virtual image, which may include a virtual body part. Furthermore, the selection input and action input may be at least a part of pre-training a user. Additionally, at block 806, methodology 800 may include instantiating virtual movement of the virtual image. In an aspect, block 806 may be, in a non-limiting aspect, performed by a computer device or by the user. Furthermore, at block 808, the methodology 800 may include reinitiating neurological functionality based on the instantiating. In an aspect, block 808 may be, in a non-limiting aspect, performed by a computer device or by the user.

Figure 9:
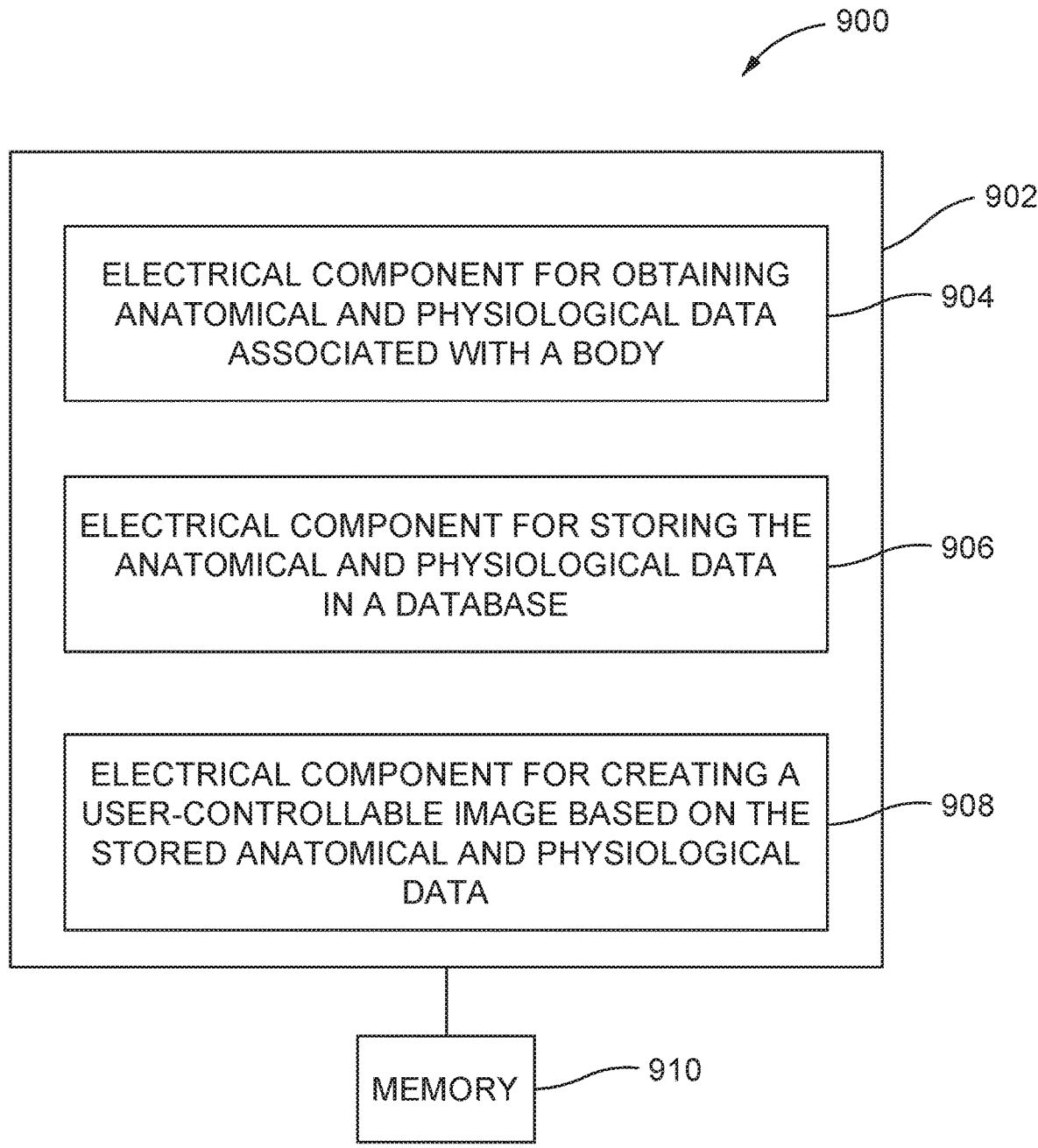
FIG. 9 is a component diagram illustrating an example grouping of electrical components for creating a UCI according to the present disclosure.

Referring to FIG. 9, an example system 900 is displayed for creating a UCI. For example, system 900 can reside at least partially within one or more computing or processing devices. It is to be appreciated that system 900 is represented as including functional blocks, which can be functional blocks that represent processes implemented by a processor, software, or combination thereof (e.g., firmware). System 900 includes a logical grouping 902 of electrical components that can act in conjunction. For instance, logical grouping 902 can include an electro-mechanical component 904 for obtaining anatomical and physiological data associated with a body. In an aspect, electrical component 904 may comprise anatomical and physiological data obtaining component 302 (FIG. 3). In addition, logical grouping 902 can include an electrical component 906 for storing the anatomical and physiological data in a database. In an aspect, electrical component 906 may comprise UCI creating device 300, memory 304 (FIG. 3), or processor 402 (FIG. 4). In addition, logical grouping 902 can include an electrical component 908 for creating a UCI based on the stored anatomical and physiological data. In an aspect, electrical component 908 may comprise UCI creating component 310 (FIG. 3).

Additionally, system 900 can include a memory 910 that retains instructions for executing processes associated with the electrical components 904, 906, and 908, stores data used or obtained by the electrical components 904, 906, and 908, etc. While shown as being external to memory 910, it is to be understood that one or more of the electrical components 904, 906, and 908 can exist within memory 910. In one example, electrical components 904, 906, and 908 can comprise at least one processor, or each electrical component 904, 906, and 908 can be a corresponding module of at least one processor. Moreover, in an additional or alternative example, electrical components 904, 906, and 908 can be a computer program product including a computer readable medium, where each electrical component 904, 906, and 908 can be corresponding code.

Figure 10:
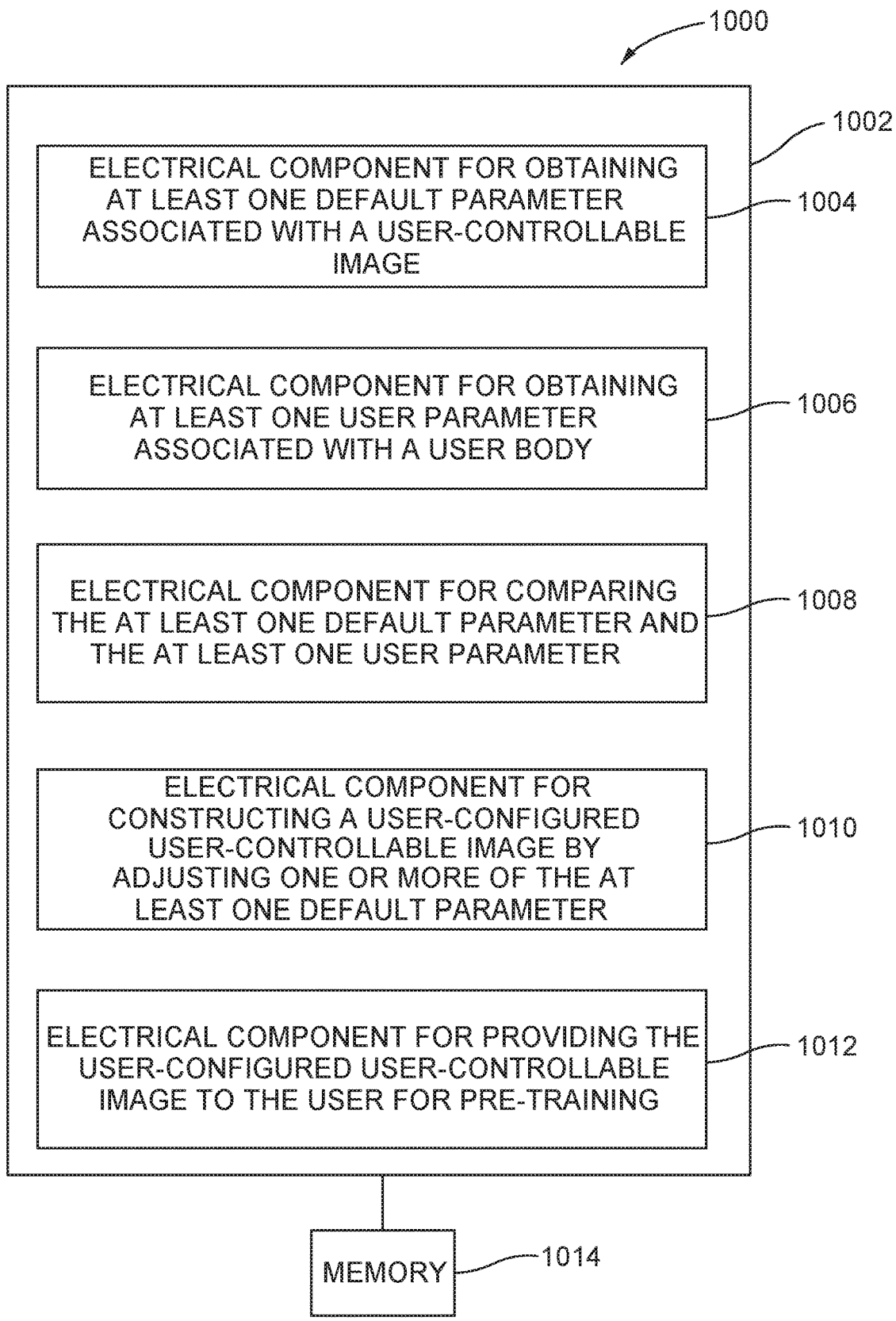
FIG. 10 is a component diagram illustrating an example grouping of electrical components for configuring a UCI to a user according to the present disclosure.

Referring to FIG. 10, an example system 1000 is displayed for creating a UCI. For example, system 1000 can reside at least partially within one or more computing or processing devices. It is to be appreciated that system 1000 is represented as including functional blocks, which can be functional blocks that represent processes implemented by a processor, software, or combination thereof (e.g., firmware). System 1000 includes a logical grouping 1002 of electrical components that can act in conjunction. For instance, logical grouping 1002 can include an electrical component 1004 for obtaining at least one default parameter associated with a UCI. In an aspect, electrical component 1004 may comprise computer device 102 (FIGS. 1 and 2). In addition, logical grouping 1002 can include an electrical component 1006 for obtaining at least one user parameter associated with a user body. In an aspect, electrical component 1006 may comprise computer device 102 (FIGS. 1 and 2). In addition, logical grouping 1002 can include electrical component 1008 for comparing the at least one default parameter and the at least one user parameter. In an aspect, electrical component 808 may comprise user-configured UCI manager 212 (FIG. 2). In addition, logical grouping 1002 can include an electrical component 1010 for constructing a user-configured UCI by adjusting one or more of the at least one default parameter. In an aspect, electrical component 1010 may comprise user-configured UCI manager 212 (FIG. 2). In addition, logical grouping 1002 can include an electrical component 1012 for providing the user-configured UCI to the user for pre-action training. In an aspect, electrical component 1012 may comprise computer device 102 (FIGS. 1 and 2).

Additionally, system 1000 can include a memory 1014 that retains instructions for executing processes associated with the electrical components 1004, 1006, 1008, 1010, and 1012, stores data used or obtained by the electrical components 1004, 1006, 1008, 1010, and 1012, etc. While shown as being external to memory 1014, it is to be understood that one or more of the electrical components 1004, 1006, 1008, 1010, and 1012 can exist within memory 1014. In one example, electrical components 1004, 1006, 1008, 1010, and 1012 can comprise at least one processor, or each electrical component 1004, 1006, 1008, 1010, and 1012 can be a corresponding module of at least one processor. Moreover, in an additional or alternative example, electrical components 1004, 1006, 1008, 1010, and 1012 can be a computer program product including a computer readable medium, where each electrical component 1004, 1006, 1008, 1010, and 1012 can be corresponding code.

Figure 11:
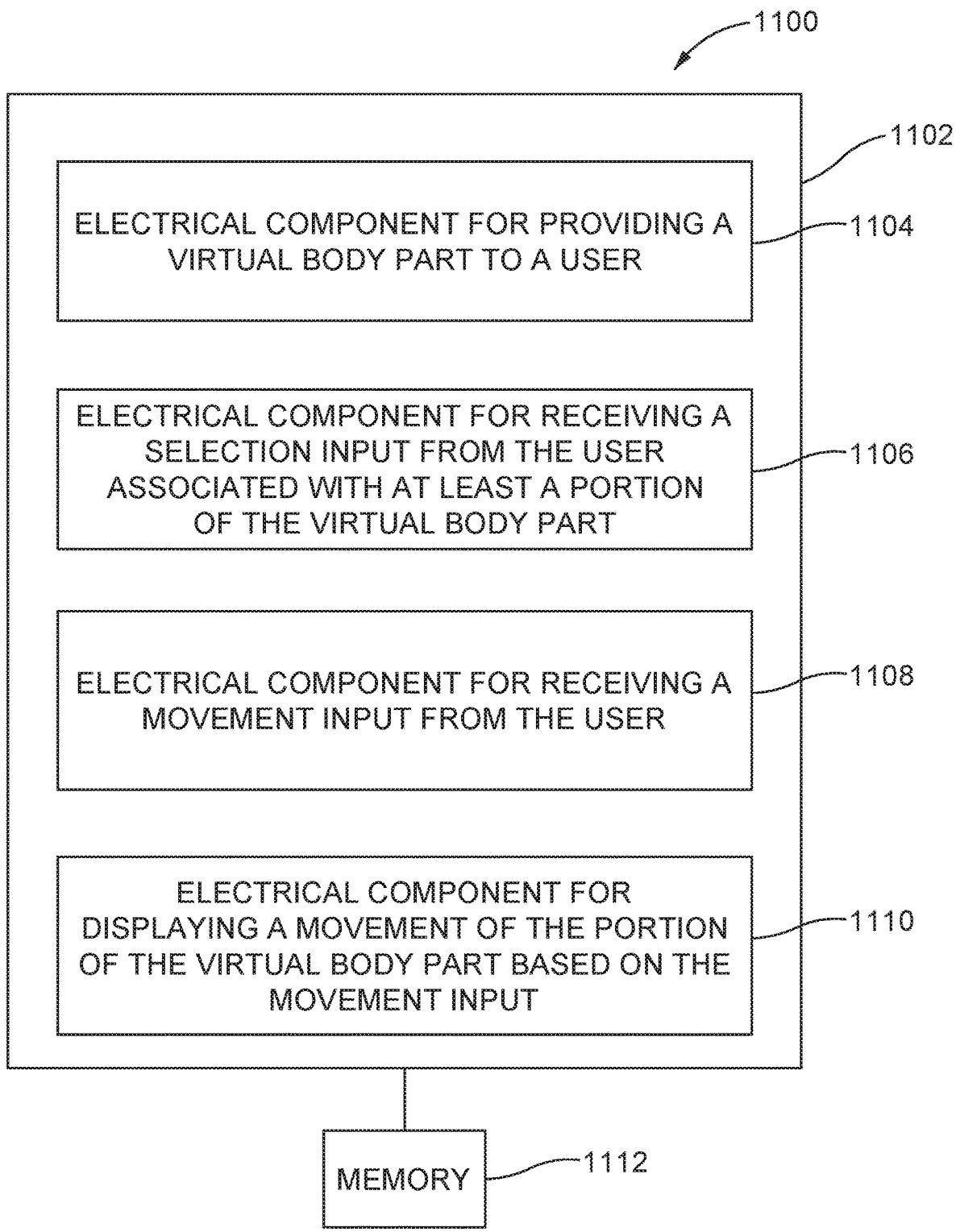
FIG. 11 is a component diagram illustrating an example grouping of electrical components for providing pre-action training activities to a user according to the present disclosure.

Referring to FIG. 11, an example system 1100 is displayed for creating and displaying a UCI. For example, system 1100 can reside at least partially within one or more computing or processing devices. It is to be appreciated that system 1100 is represented as including functional blocks, which can be functional blocks that represent processes implemented by a processor, software, or combination thereof (e.g., firmware). System 1100 includes a logical grouping 1102 of electrical components that can act in conjunction. For instance, logical grouping 1102 can include an electrical component 1104 for providing a virtual body part to a user. In an aspect, electrical component 1104 may comprise computer device 102 (FIGS. 1 and 2). In addition, logical grouping 1102 can include an electrical component 1106 for receiving a selection input from the user associated with at least a portion of the virtual body part. In an aspect, electrical component 1106 may selection input manager 206 (FIG. 2). In addition, logical grouping 1102 can include an electrical component 1108 for receiving an action input from the user. In an aspect, electrical component 1108 may comprise action input manager 208 (FIG. 2). In addition, logical grouping 1102 can include an electrical component 1110 for displaying an action of the portion of the virtual body part based on the action input. In an aspect, electrical component 1110 may comprise computer device 102 (FIGS. 1 and 2).

Additionally, system 1100 can include a memory 1112 that retains instructions for executing processes associated with the electrical components 1104, 1106, 1108, and 1110, stores data used or obtained by the electrical components 1104, 1106, 1108, and 1110, etc. While shown as being external to memory 1112, it is to be understood that one or more of the electrical components 1104, 1106, 1108, and 1110 can exist within memory 1112. In one example, electrical components 1104, 1106, 1108, and 1110 can comprise at least one processor, or each electrical component 1104, 1106, 1108, and 1110 can be a corresponding module of at least one processor. Moreover, in an additional or alternative example, electrical components 1104, 1106, 1108, and 1110 can be a computer program product including a computer readable medium, where each electrical component 1104, 1106, 1108, and 1110 can be corresponding code.

Figure 12:
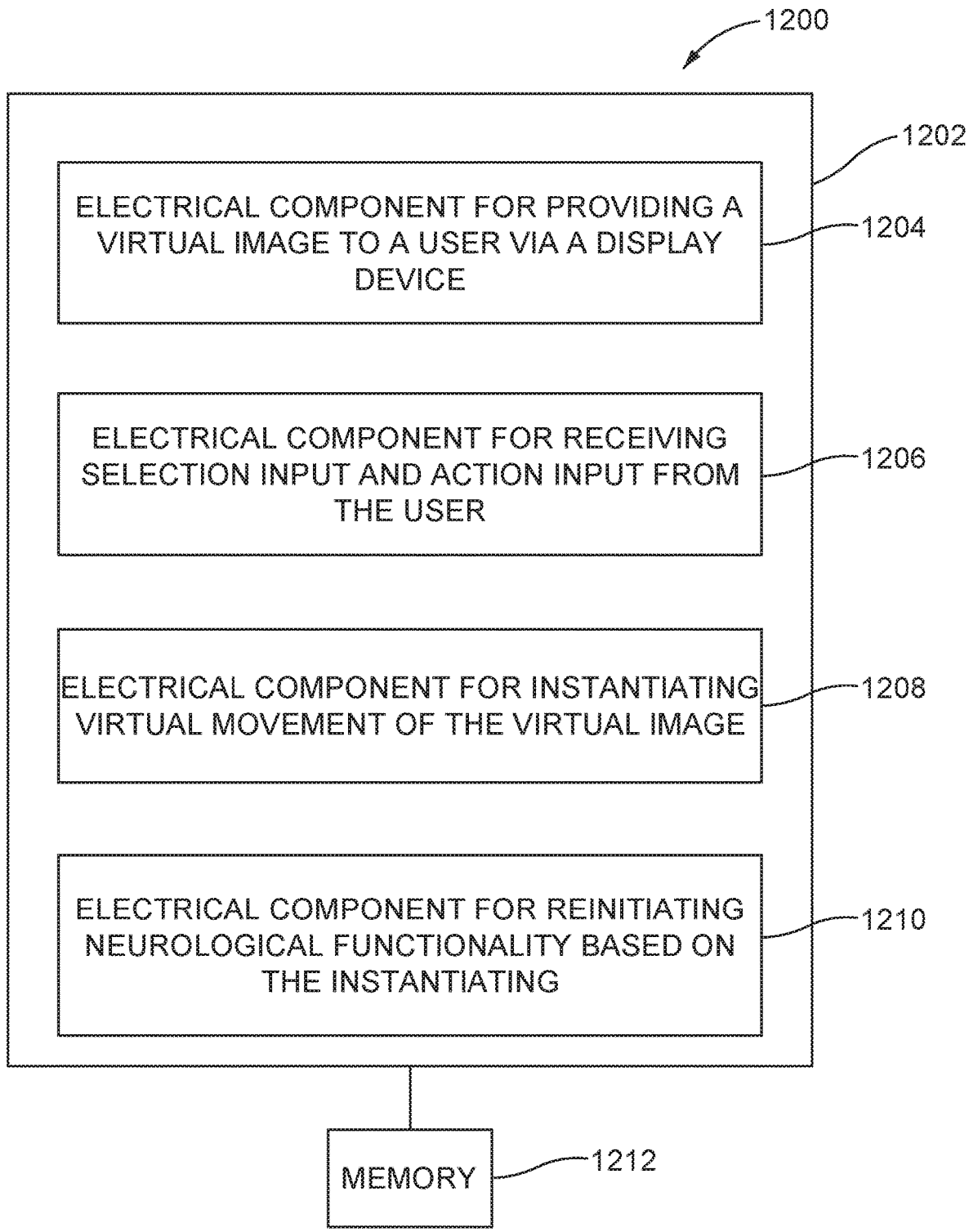
FIG. 12 is a component diagram illustrating an example grouping of electrical components for instantiating kinetic imagery, i.e. embodiments of cortical simulation and reinitiating neurological functionality according to the present disclosure.

Referring to FIG. 12, an example system 1200 is displayed for instantiating virtual movement of a virtual image and reinitiating neurological functionality. For example, system 1200 can reside at least partially within one or more computing or processing devices. It is to be appreciated that system 1200 is represented as including functional blocks, which can be functional blocks that represent processes implemented by a processor, software, or combination thereof (e.g., firmware). System 1200 includes a logical grouping 1202 of electrical components that can act in conjunction. For instance, logical grouping 1202 can include an electrical component 1204 for providing a virtual image to a user via a display device. In addition, logical grouping 1202 can include an electrical component 1206 for receiving a selection input and an action input from the user. In addition, logical grouping 1202 can include an electrical component 1208 for instantiating virtual movement of the virtual image. In addition, logical grouping 1202 can include an electrical component 1210 for reinitiating neurological functionality based on the instantiating. In an aspect, system 1200 may comprise computer device 102 (FIGS. 1 and 2).

Additionally, system 1200 can include a memory 1212 that retains instructions for executing processes associated with the electrical components 1204, 1206, 1208, and 1210, stores data used or obtained by the electrical components 1204, 1206, 1208, and 1210, etc. While shown as being external to memory 1212, it is to be understood that one or more of the electrical components 1204, 1206, 1208, and 1210 can exist within memory 1212. In one example, electrical components 1204, 1206, 1208, and 1210 can comprise at least one processor, or each electrical component 1204, 1206, 1208, and 1210 can be a corresponding module of at least one processor. Moreover, in an additional or alternative example, electrical components 1204, 1206, 1208, and 1210 can be a computer program product including a computer readable medium, where each electrical component 1204, 1206, 1208, and 1210 can be corresponding code.

Figure 13:
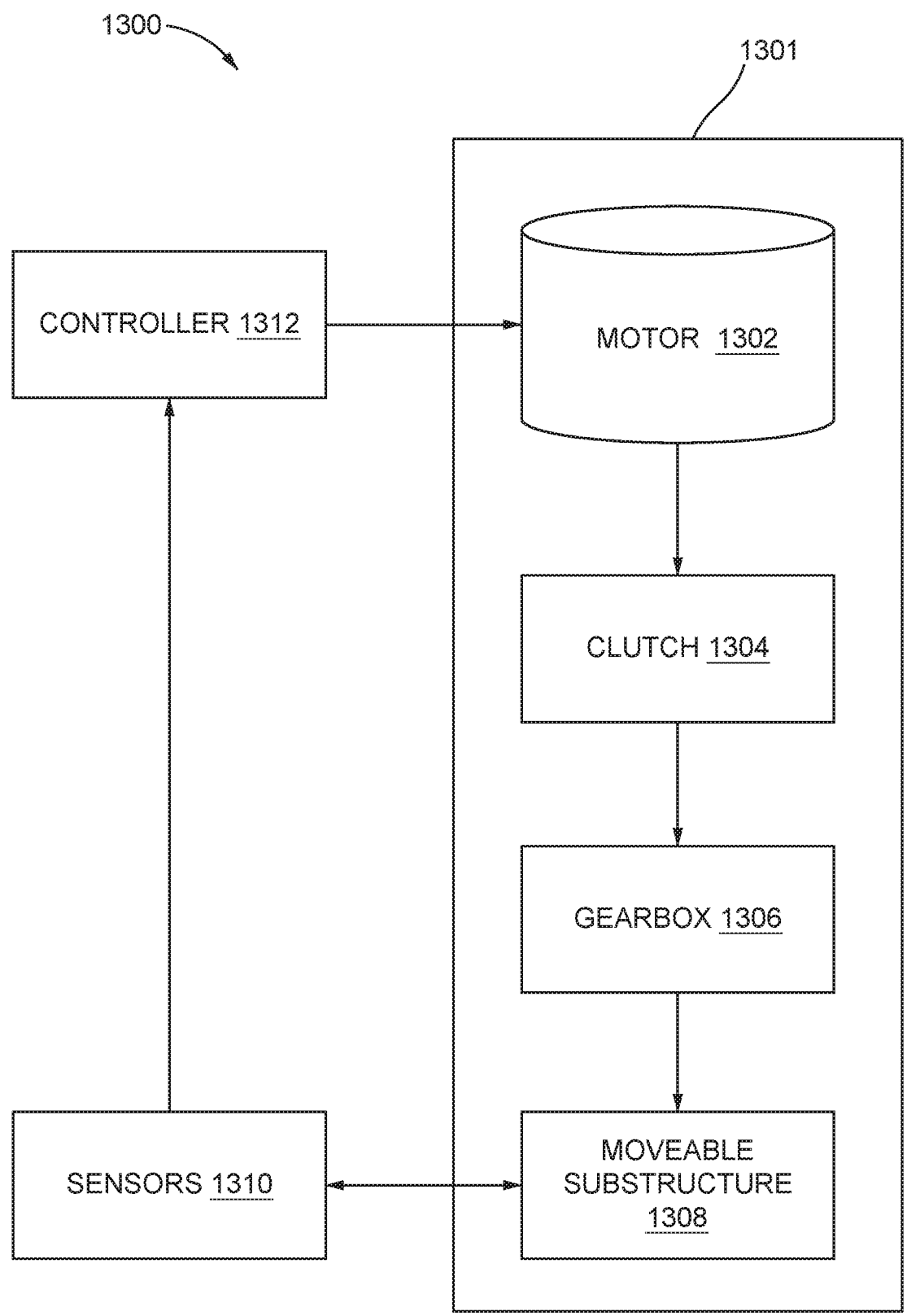
FIG. 13 is a representative drawing a non-virtual robot, powered orthotic device, prosthesis, or exoskeleton body part according to the present disclosure.

FIG. 13 is a representative drawing of a system 1300, which may include a non-virtual robot 1301, which may be configured to move in response to an input from a user. In an aspect, such input may be a non-corresponding movement input by an input device, such as a mouse, in a manner according to one or more methods provided herein. In an aspect, non-virtual robot 1301 may comprise a prosthesis, powered orthotic device, exoskeleton, or other motorized device that may physically move in response to one or more inputs or pre-programmed or pre-recoded controls Additionally, non-virtual robot 1301 may include a motor 1302, which may be a uni- or bi-directional motor for moving one or more moveable substructures 1308, which may comprise one or more parts of non-virtual robot 1301, such as, but not limited to a finger, limb, head, foot, hand, etc. Some actuator technologies or body part designs may utilize a plurality of motors 1302 (or other actuators) to move the one or more moveable substructures 1308. Further, to create such movement, non-virtual robot 1301 may include a clutch 1304 and/or a gearbox 1306 for controlling aspects of the movement of moveable substructure 1308, such as, but not limited to, speed, force, etc.

Furthermore, system 1300 may include a controller 1312, which may be configured to control motor 1302 and/or any other component of non-virtual robot 1301 based on one or more inputs. In an aspect, these one or more inputs may comprise non-corresponding input from a user and/or a feedback input output by one or more sensors 1310, which may be configured to sense and/or analyze movement of the one or more moveable substructure 1308.

Figure 14:
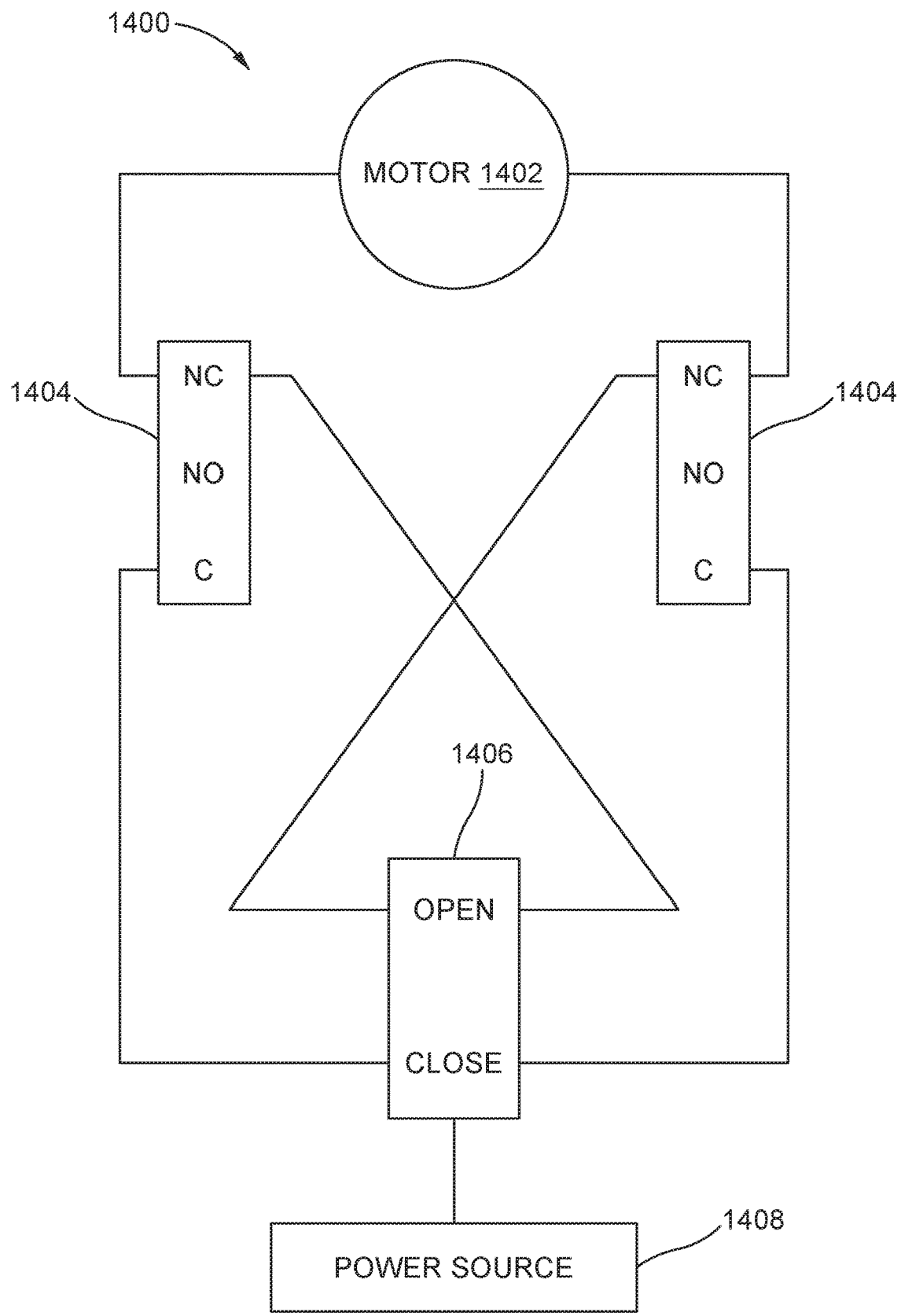
FIG. 14 is a representative wiring diagram of a non-virtual robot, powered orthotic device, prosthesis, or exoskeleton body part according to the present disclosure.

FIG. 14 is a representative wiring diagram of a device 1400, which may comprise a non-virtual robot, powered orthotic device, prosthesis, or exoskeleton body part, such as, but not limited to, non-virtual robot 1301 of FIG. 13. In an aspect, device 1400 may utilize a manual switch 1406 to engage either of the bi-directional circuits 1404 for controlling a motor 1402, which may be a bi-directional motor. In an aspect, manual switch 1406 may be a three-position Double Pole Double Throw (2P2T) switch for engaging either open or close operation, and which may be center-loaded for neither engagement. Furthermore, device 1400 may include a pair (or more than two) of limit switches 1404 corresponding to two (or more) interleaved circuits (extensor and flexor, i.e. open and close), which may limit motion associated with motor 1402.

Figure 15:
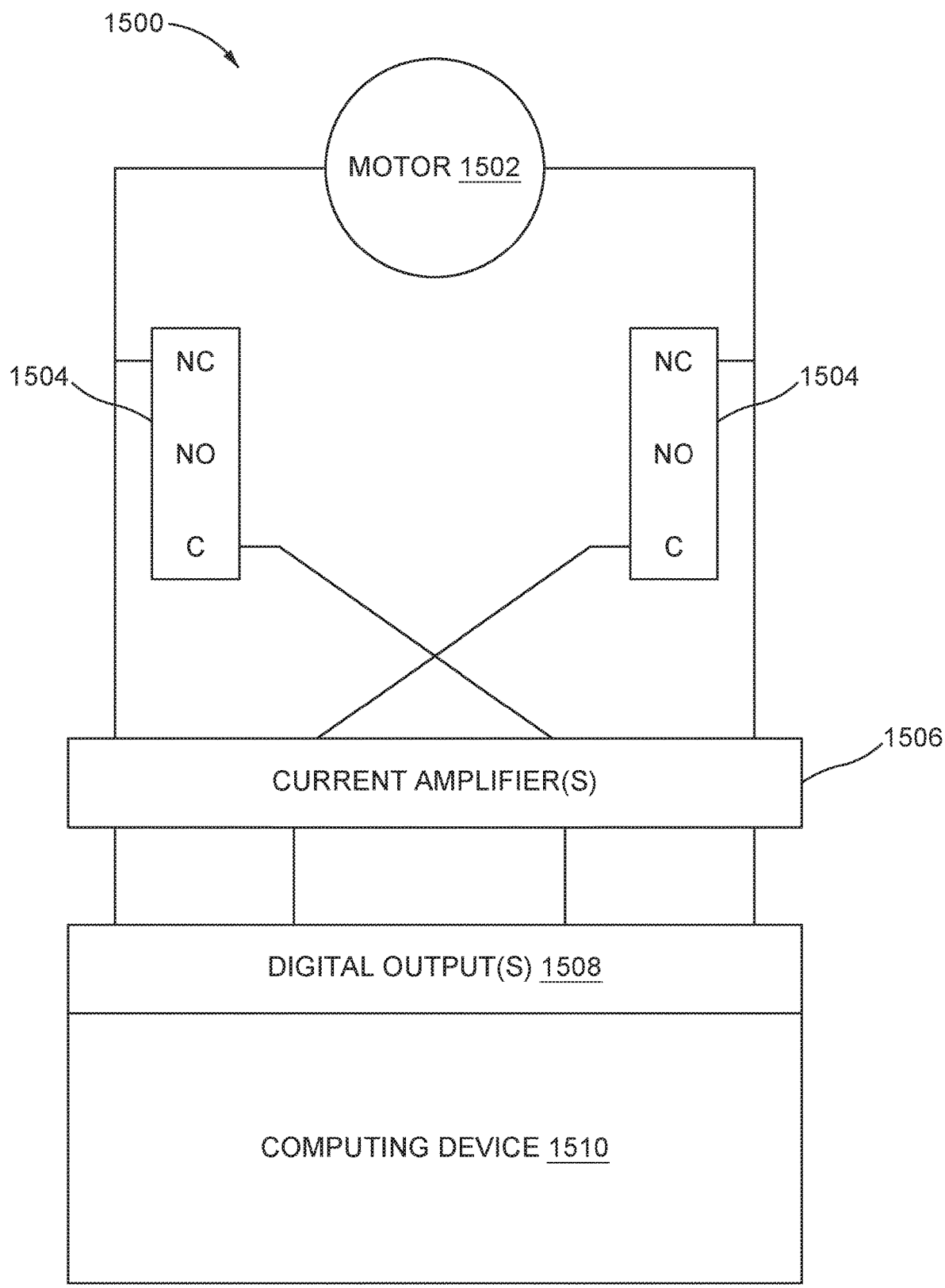
FIG. 15 is a representative wiring diagram of a non-virtual robot powered orthotic device prosthesis, or exoskeleton body part according to the present disclosure.

FIG. 15 is a representative wiring diagram of a device 1500, which may be a non-virtual robot, powered orthotic device, prosthesis, or exoskeleton body part (e.g., of FIGS. 13 and/or 14). In an aspect, device 1500 may operate in response to one or more digital outputs 1508 from a computing device 1510, which may control the movement of device 1500 and the associated motor 1502. For example, the digital outputs 1508 may engage bi-directional circuits, which may incorporate the 2P2T switch circuits present in FIG. 14 (not shown here). Furthermore, current amplifiers 1506 (or voltage amplifiers) may amplify the one or more digital outputs 1508 (or analog outputs) to cause movement via motor 1502. Also, though not shown in FIG. 15, device 1500 may include a plurality of sensors capable of being incorporated which each of one or more body part structures or sub-structures (e.g., moveable substructure 1308 of FIG. 13).

Figure 16A:
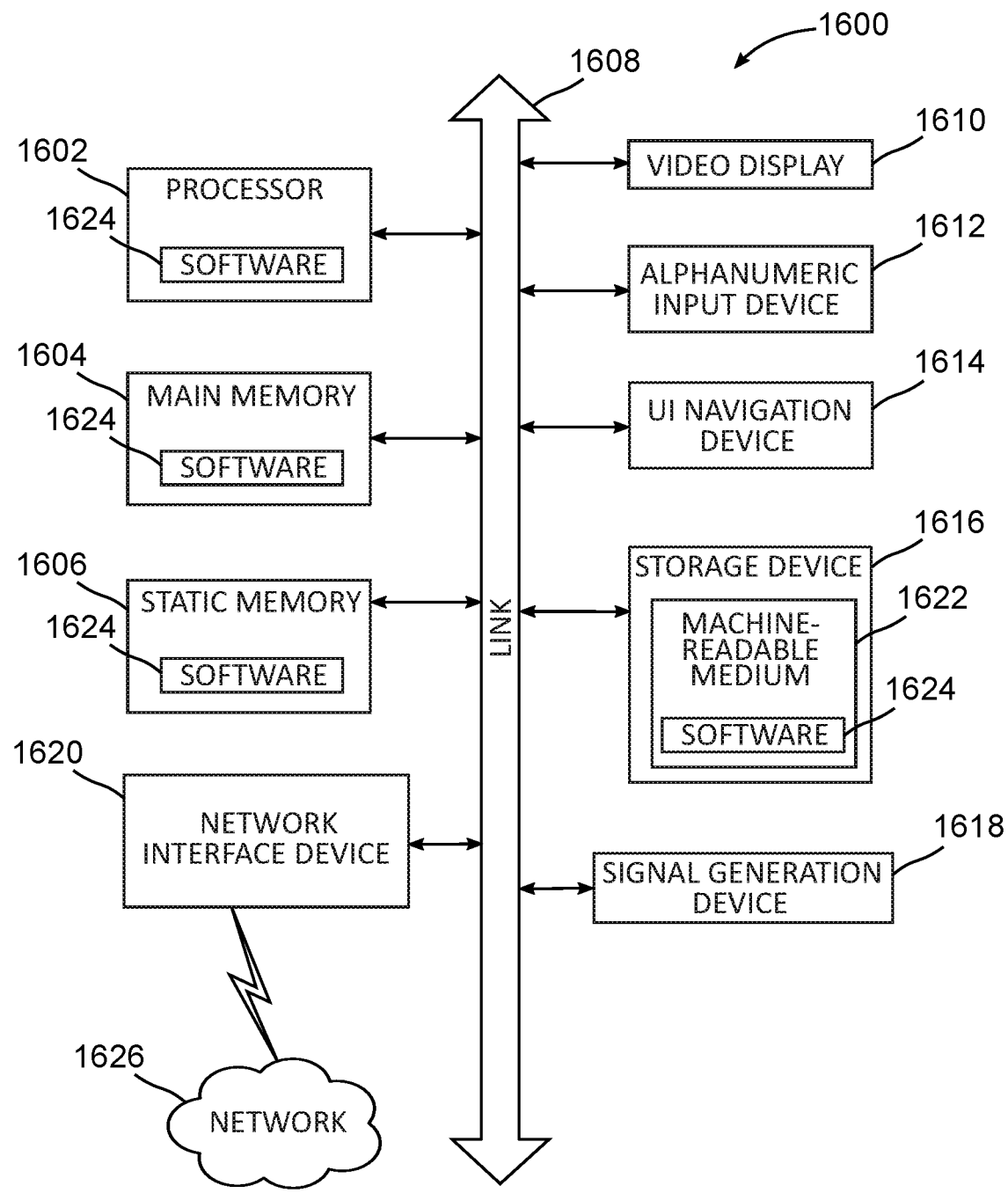
FIG. 16A is a block diagram illustrating a machine in the example form of a computer system according to an example aspect of the present disclosure.

FIG. 16A is a block diagram illustrating a machine in the example form of a computer system 1600 and may be an embodiment of computer device 102 of computer based system 100 of FIG. 1. Within computer system 1600, a set or sequence of instructions for causing the machine to perform any one of the methodologies discussed herein may be executed, according to an example embodiment. In some embodiments, the set or sequence of instructions may reside elsewhere and computer 1600 may access the set or sequence of instructions for execution. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a set-top box (STB), a Personal Digital Assistant (PDA), a mobile telephone, a web appliance, a network router, switch or bridge, a cloud-based computing device, or any machine capable of executing instructions (sequential or otherwise) that specify actions to be taken by that machine. Further, while only a single machine is illustrated, the term "machine" shall also be taken to include any centralized or distributed collection of machines that individually or jointly execute a set (or multiple sets) of instructions to perform any one or more of the methodologies discussed herein.

Example computer system 1600 includes at least one processor 1602 (e.g., a central processing unit (CPU), a graphics processing unit (GPU) or both, processor cores, compute nodes, etc.), a main memory 1604 and a static memory 1605, which communicate with each other via a link 1608 (e.g., bus). The computer system 1600 may further include a video display unit 1610 (e.g., may be a display device 106 in an embodiment of computer based system 100), an alphanumeric input device 1612 (e.g., a keyboard, and may be an input device 104 in an embodiment of computer based system 100), and a user interface (UI) navigation device 1614 (e.g., a mouse, and may be an input device 104 in an embodiment of computer based system 100). In one embodiment, the video display unit 1610, input device 1612 and UI navigation device 1614 are incorporated into a touch screen display. The computer system 1600 may additionally include a storage device 1615 (e.g., a drive unit), a signal generation device 1618 (e.g., a speaker), a network interface device 1620, and one or more sensors (not shown), such as a global positioning system (GPS) sensor, compass, accelerometer, or other sensor.

The storage device 1615 includes a machine-readable medium 1622 on which is stored one or more sets of data structures and instructions 1624 (e.g., software) embodying or utilized by any one or more of the methodologies or functions described herein. The instructions 1624 may also reside, completely or at least partially, within the main memory 1604, static memory 1605, and/or within the processor 1602 during execution thereof by the computer system 1600, with the main memory 1604, static memory 1605, and the processor 1602 also constituting machine-readable media.

While the machine-readable medium 1622 is illustrated in an example embodiment to be a single medium, the term "machine-readable medium" may include a single medium or multiple media (e.g., a centralized or distributed database, and/or associated caches and servers) that store the one or more instructions 1624. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1624 may further be transmitted or received over a communications network 1626 using a transmission medium via the network interface device 1620 utilizing any one of a number of well-known transfer protocols (e.g., HTTP, XML). Examples of communication networks include a local area network (LAN), a wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Figure 16B:
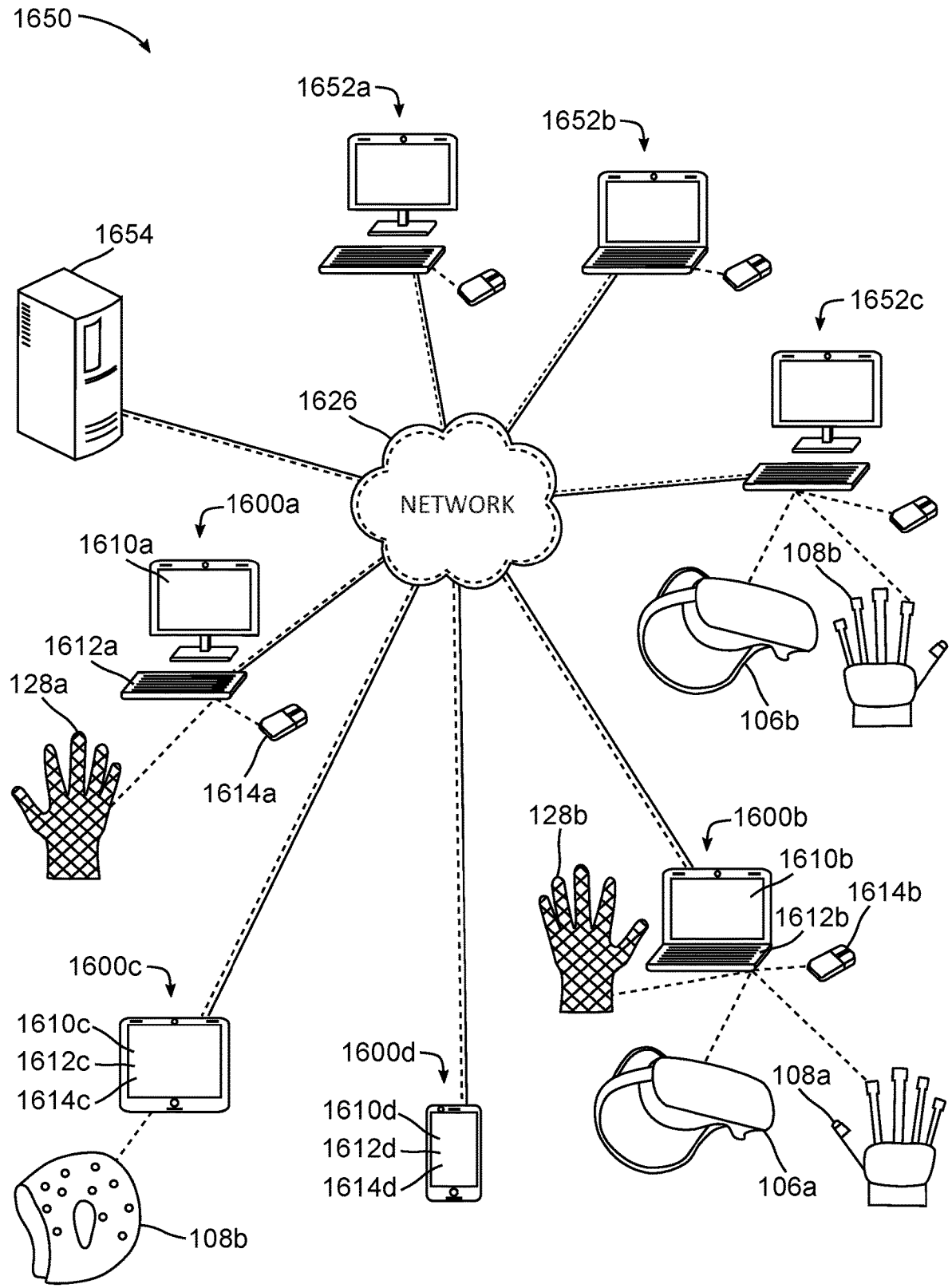
FIG. 16B is a system diagram illustrating an example tele-rehabilitation system.

FIG. 16B illustrates a system diagram of an example tele-rehabilitation (synonymously tele-rehab, telehealth) system 1650. Example tele-rehabilitation system 1650 may comprise a plurality of networked user machines 1600, which, for illustration, are shown in the example forms of a desktop computer 1600a, a laptop computer 1600b, a tablet computer 1600c and a smartphone 1600d, but may be any suitable networked computing device. User machines 1600a, 1600b, 1600c and 1600d may be embodiments of computer device 102 of computer based system 100 of FIG. 1, and may be used by users in conjunction with a rehabilitative therapy protocol which may be operated in part and in conjunction with one or more tele-rehabilitation services, telehealth services or other network delivered services. Example tele-rehabilitation system 1650 may comprise one or more networked therapist machines, which, for illustration, are shown in the example forms of desktop computers 1652a and 1652c, and a laptop computer 1652b, but may be any suitable networked computing device. Example tele-rehabilitation system 1650 may comprise a server based system 1654, wherein server based system 1654 may comprise one or more servers, software and data services comprising one or more databases, may be a cloud-based system and may be located in one or more physically separate locations. User machines 1600a, 1600b, 1600c and 1600d, therapist machines 1652a, 1652b and 1652c, and server based system 1654 may be located in a plurality of physically separate locations and may be connected to a network 1626 (as shown by a solid line adjacent a dashed line) such that communications may be established therebetween.

Users may use user machines 1600a, 1600b, 1600c and 1600d to receive tele-rehabilitation services, telehealth services or other network delivered services, and to play pre-action exercise games (PEGs) as described above, wherein users may use pre-movement and pre-action self-re-training/re-learning to self-re-learn or self-learn to perform a physical movement and action. In an example embodiment, user machine 1600a may be in the form of a desktop computer system, comprising a desktop video display unit 1610a (e.g., may be a display device 106 in an embodiment of computer based system 100), an alphanumeric input device 1612a (i.e., a desktop keyboard, and may be an input device 104 in an embodiment of computer based system 100) and a user interface (UI) navigation device 1614a (e.g., a mouse, and may be an input device 104 in an embodiment of computer based system 100). The example embodiment of user machine 1600a may be configured with a body part device 128a (e.g., may be a body part device 128 in an embodiment of computer based system 100), wherein a body part device may be, but is not limited to being, a robotic arm, shoulder, prosthetic limb, a powered orthotic device, glove, sleeve, sock, or the like as described herein, and in the example embodiment of user machine 1600a, body part device 128a may be as depicted, a glove device (as will be later discussed in more detail herein, inclusive of its use relating to embodiments and aspects disclosed herein). In the illustrated embodiment, body part device 128a configured with user machine 1600a is a right-hand glove body part device 128a (depicted from a back of hand perspective in FIG. 16B). However, it should be appreciated that any suitable body part device may be configured with user machine 1600a.

In an example embodiment, user machine 1600b may be in the form of a laptop computer system, comprising a laptop video display unit 1610b (e.g., may be a display device 106 in an embodiment of computer based system 100), an alphanumeric input device 1612b (e.g., a laptop keyboard, and may be an input device 104 in an embodiment of computer based system 100) and a user interface (UI) navigation device 1614b (e.g., a mouse, and may be an input device 104 in an embodiment of computer based system 100), which may be an external mouse as depicted or an integrated mouse, which is, for example, integrated into a surface of the laptop and adjacent to alphanumeric input device 1612b. The example embodiment of user machine 1600b may be configured with a body part device 128b (e.g., may be a body part device 128 in an embodiment of computer based system 100), wherein a body part device may be, but is not limited to being, a robotic arm, shoulder, prosthetic limb, a powered orthotic device, glove, sleeve, sock, or the like as described herein, and in the example embodiment of user machine 1600b, body part device 128b may be as depicted, a glove device (as will be later discussed in more detail herein, inclusive of its use relating to embodiments and aspects disclosed herein). In the illustrated embodiment, body part device 128b of user machine 1600b is a left-hand glove body part device 128b (depicted from a back of hand perspective in FIG. 16B). However, it should be appreciated that any suitable body part device may be configured with user machine 1600b. The example embodiment of user machine 1600b may be configured with a user measurement device 108a (e.g., may be a user measurement device 108 in an embodiment of computer based system 100), which may be a measurement glove device (as will be later discussed in more detail herein, inclusive of its use relating to embodiments and aspects disclosed herein). The example embodiment of user machine 1600b may be configured with a display device 106a (e.g., may be a display device 106 in an embodiment of computer based system 100), wherein a display device may be, but is not limited to being, a digital display device, a holographic display device, a virtual reality (VR) headset display device or other display device, and in the example embodiment of user machine 1600b, display device 106a may be a VR display device (as will be later discussed in more detail herein, inclusive of its use relating to embodiments and aspects disclosed herein).

In an example embodiment, user machine 1600c may be in the form of a tablet computer system, comprising a tablet video display unit 1610c (e.g., may be a display device 106 in an embodiment of computer based system 100), a user interface (UI) navigation device 1614c (e.g., a touchscreen, and may be an input device 104 in an embodiment of computer based system 100) and an alphanumeric input device 1612c (e.g., a generated touch keyboard, which may be generated using tablet video display unit 1610c and user interface (UI) navigation device 1614c, and may be an input device 104 in an embodiment of computer based system 100). The example embodiment of user machine 1600c may be configured with a user measurement device 108b (e.g., may be a user measurement device 108 in an embodiment of computer based system 100), which may be an electroencephalograph (EEG) cap device (as will be later discussed in more detail herein, inclusive of its use relating to embodiments and aspects disclosed herein).

In an example embodiment, user machine 1600d may be in the form of a smartphone (e.g., a form of a computer system), comprising a smartphone video display unit 1610d (e.g., may be a display device 106 in an embodiment of computer based system 100), a user interface (UI) navigation device 1614d (e.g., a touchscreen, and may be an input device 104 in an embodiment of computer based system 100) and an alphanumeric input device 1612d (e.g., a generated touch keyboard, which may be generated using smartphone video display unit 1610d and user interface (UI) navigation device 1614d, and may be an input device 104 in an embodiment of computer based system 100). In an embodiment not shown, user machine 1600d may be configured with: a right-hand glove body part device 128a, a left-hand glove body part device 128b and/or another body part device; a user measurement glove device 108a, a user measurement EEG cap device 108b and/or another user measurement device; and/or, a VR display device 106*a* and/or another display device.

As is apparent in the foregoing discussion, many combinations of devices and forms of computer systems (computer device 102 of FIG. 1) are possible to configure user machines 1600 and to provide various embodiments of user systems 100 of FIG. 1. Configurations of user machines 1600 and user systems 100 may be based at least in part on therapeutic requirements, therapeutic performance, therapeutic responses, availability and specifications of computer systems, availability and specifications of devices, and/or other considerations.

A therapist (or other healthcare professional or caregiver) may use a therapist machine, such as, 1652*a*, 1652*b* and 1652*c* to provide tele-rehabilitation services, telehealth services or other network delivered services via network 1626 to a user using a user machine, such as 1600*a*, 1600*b*, 1600*c* and 1600*d* to receive tele-rehabilitation services, telehealth services or other network delivered services. Data may be generated, captured, processed, stored, used and/or the like by one or more user machines 1600*a*, 1600*b*, 1600*c* and 1600*d*, one or more therapist machines 1652*a*, 1652*b* and 1652*c*, and/or server based system 1654, wherein data may be related to, but is not limited to, therapeutic performance, therapeutic responses, measured user characteristic data, user performance, user responses, other user measured data, where such measured user data may include without limitation, neurological, chemical, or any other data related to a user's body (e.g., without limitation neurological signaling data or maps, neuron activity data, etc.) generated and/or observed by a user measurement device before, during, and/or after a user engaging in tele-rehabilitation and/or other healthcare related services. In an embodiment, such data may be processed using machine learning (ML) and artificial intelligence (AI) technologies to model, optimize and/or prescribe user therapies, therapeutic services, tele-rehabilitation services, telehealth services or other network delivered services, and to develop and optimize new PEGs or to modify and optimize existing PEGs.

Figure 17A:
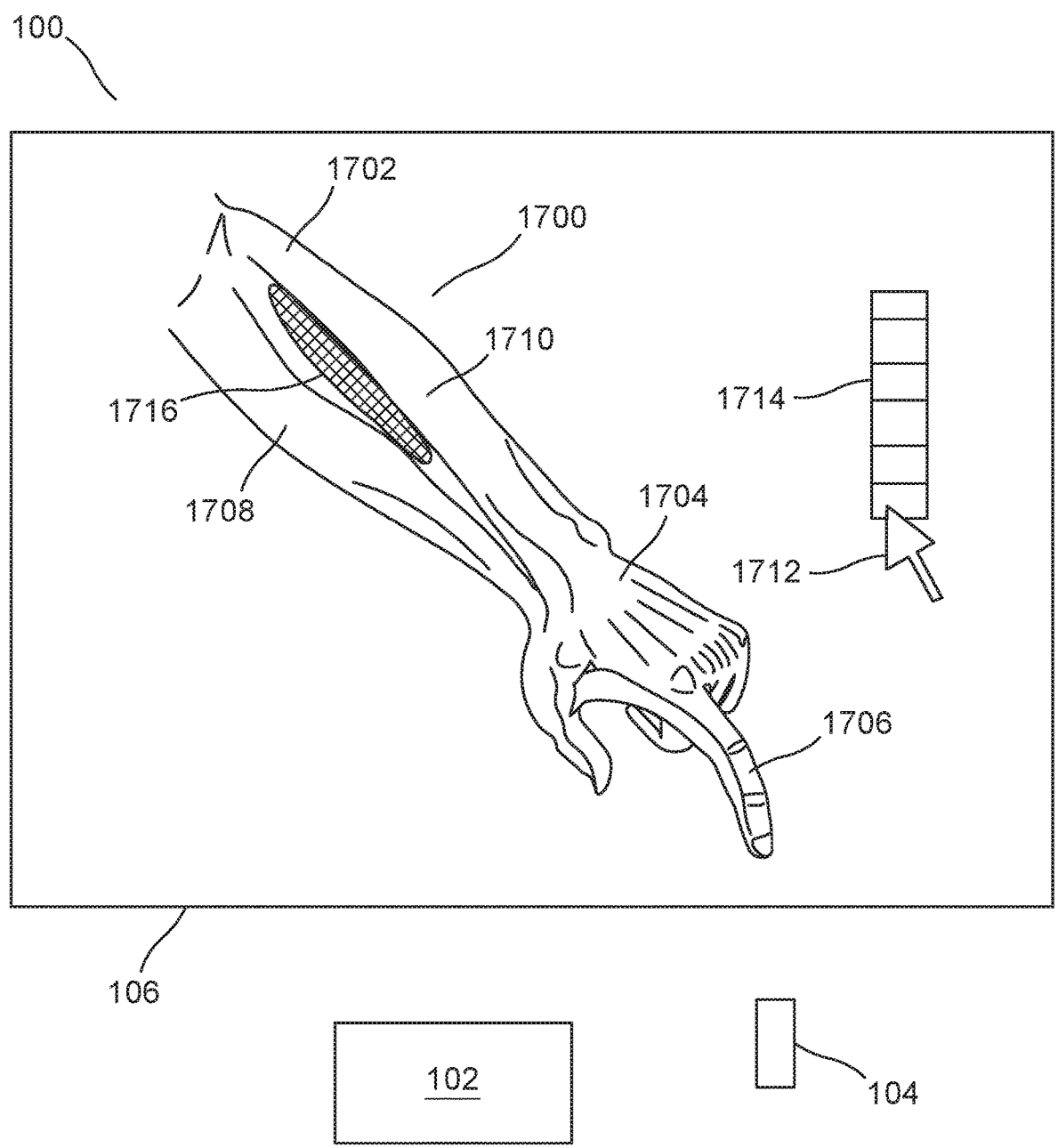
FIGS. 17A and 17B illustrate a virtual body part displayed by a display device and showing the virtual body part in a first configuration and in a second configuration.
Figure 17B:
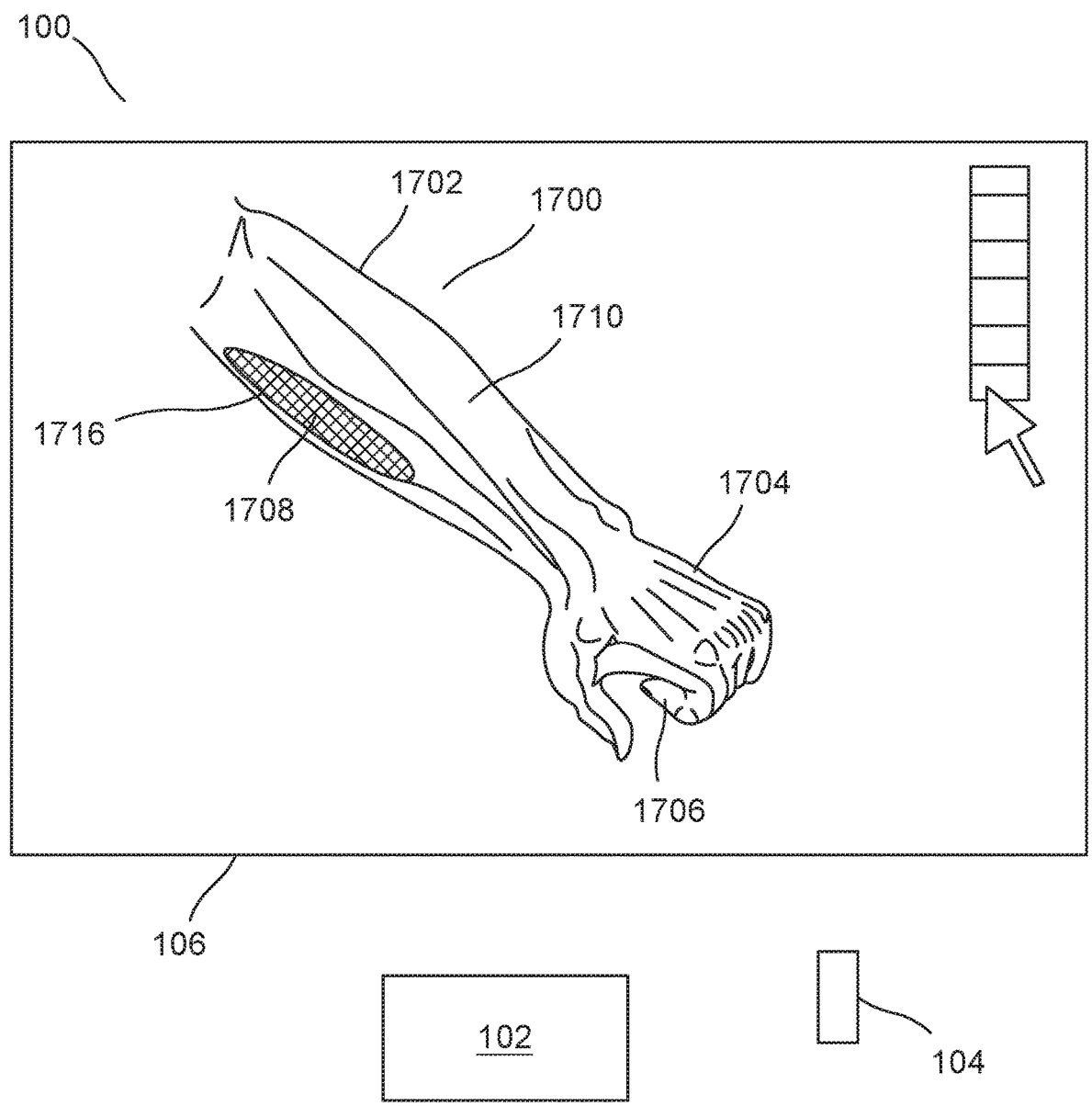

Referring to FIGS. 17A and 17B in combination with FIGS. 1-2, one aspect of virtual body part 1700 is shown to illustrate an example of system 100 in use with pre-movement and pre-action self-re-training/re-learning where the user seeks to self-re-learn or self-learn to perform a physical movement and action. System 100 includes computer device 102, input device 104, and display device 106. In this example, virtual body part 1700 is a left forearm 1702 including hand 1704 and index finger 1706. Selection input manager 206 of system 100 has mapped select locations associated with selection input to virtual body part 1700 and parts thereof corresponding to simulated movement and actions by virtual body part 1700. These select locations correspond to a user's body part that requires physical motor and related cognitive and nervous system improvements. Movement and action input manager 208 is configured to receive movement and action inputs from user 120 and system 100 generates one or more display control signals that cause virtual body part 1700 to perform a movement and action.

For example, in response to user input, the user views a demonstrative movement and action of index finger 1706 moving from a first configuration in which index finger 1706 is extended as shown in FIG. 17A to a second configuration in which index finger 1706 is flexed as shown in FIG. 17B. Index finger moves from the extended configuration to the flexed configuration by virtually stimulating a flexor muscle 1708 corresponding to index finger 1706. Index finger 1706 moves back to the extended configuration by releasing (or ceasing to stimulate) flexor muscle 1708 and stimulating an extensor muscle 1710 corresponding to index finger 1706. Optionally, system 100 communicates a signal to one, some, or all of a feedback device 130, body part device 128, or target body part 150 of user 120.

In one embodiment, for example, input device 104 is a computer mouse where the user's selection is input to system 100 using the computer mouse to move a cursor 1712 to a location and then clicking the mouse button to make a selection. For example, user 120 uses the computer mouse to move cursor 1712 to and click on forearm 1702. User 120 can click on forearm 1702 generally, click on a part of forearm 1702 (e.g., anterior portion), click on a particular region of forearm 1702 (e.g., a particular muscle), by moving to and clicking on a list, menu 1714 or indicia 1716 (e.g., shaded region). Selections available to the user can be configured based on a level of detail chosen for the task to be completed, where the level of detail can be adjusted based on the user's abilities. For example, PEG level is set so that user 120 must select the particular muscle that moves index finger 1706. Similarly, PEG level can be set so that user 120 must only generally select forearm 1702 or near forearm 1702 to have the system display the same movement and action of index finger 1706.

In one embodiment, system 100 indicates the muscle or muscle group used and/or a sequence of muscle movement and actions required to perform a movement and action selected by user 120 or perform a movement and action. For example, non-stimulated muscles of virtual body part 1700 (e.g., muscles at rest) are displayed in one color or intensity (e.g., brown/tan or low intensity) and muscles actively being stimulated are displayed in a second color or intensity (e.g., red or high intensity). Thus, in the virtual body part 1700 shown in FIG. 17B, a virtual hand 1704, forearm 1702, and extensor muscle 1710 are displayed in brown color on display device 106. As flexor muscle 1708 is stimulated, system 100 displays flexor muscle 1708 of the virtual forearm 1702 in red color or using other indicia 1716 in addition to displaying movement of index finger 1706 from the first configuration (e.g., finger extended) to the second configuration (e.g., finger flexed) and remaining in that configuration as long as the flexor muscle 1708 is stimulated. As shown in FIG. 17B, a stimulated flexor muscle 1708 is accentuated on display device 106 by using indicia 1716 while index finger 1706 is maintained in the flexed configuration.

Figure 18:
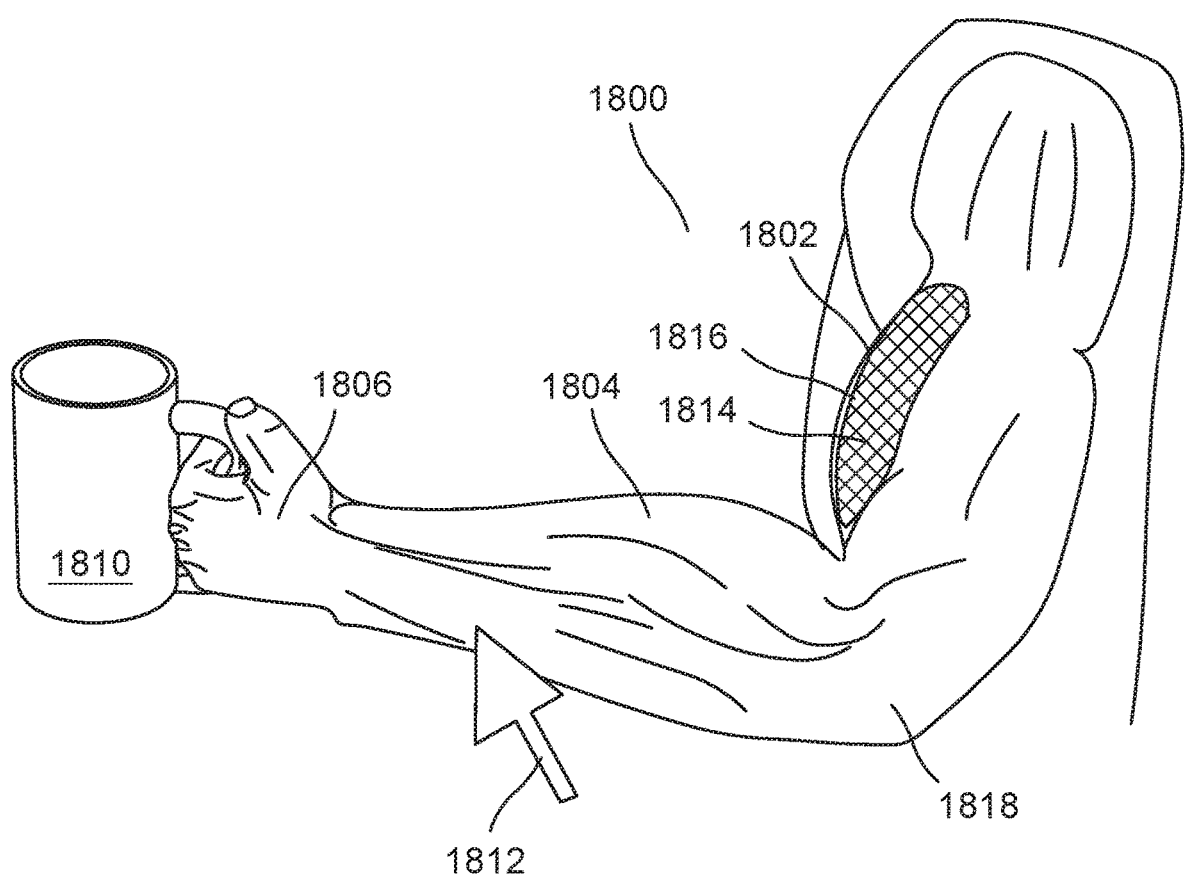
FIG. 18 illustrates an example of a virtual body part performing the task of grasping a coffee mug.

Referring to FIG. 18, a perspective view shows another aspect of virtual body part 1800 performing a task of grasping and moving a virtual coffee mug 1810. Virtual body part 1800 includes upper arm 1802, forearm 1804, and hand 1806. User 120 selects and moves virtual body part 1800 as indicated by cursor 1812. In this example, user 120 may raise or lower forearm 1804 by clicking on bicep muscle 1814, which is emphasized on display device 106 by indicia 1816 shown in FIG. 18 as cross-hatching. Using a computer mouse (not shown) as input device 104, for example, user 120 alternately may raise or lower forearm 1804 by clicking cursor 1812 on forearm 1804 and dragging the computer mouse linearly to cause forearm 1804 to pivot upwards or downwards about elbow 1818. Thus, the movement and action of user 120 is non-corresponding to the displayed movement and action of virtual body part 1800 since the actual linear movement of a computer mouse on a table or other surface does not correspond to the simulated pivoting movement and action of forearm 1804 and also does not correspond to the same amount of simulated movement as displayed. In this example, user 120 selects hand 1806 to open or close a grasp on coffee mug 1810. User 120 also may orient and align virtual body part 1800 in 3D virtual space by changing the displayed view of virtual body part 1800 and using input device 104 to cause movements needed to relocate, pick up/set down, grasp/release, rotate, or otherwise move coffee mug 1810.

Figure 19:
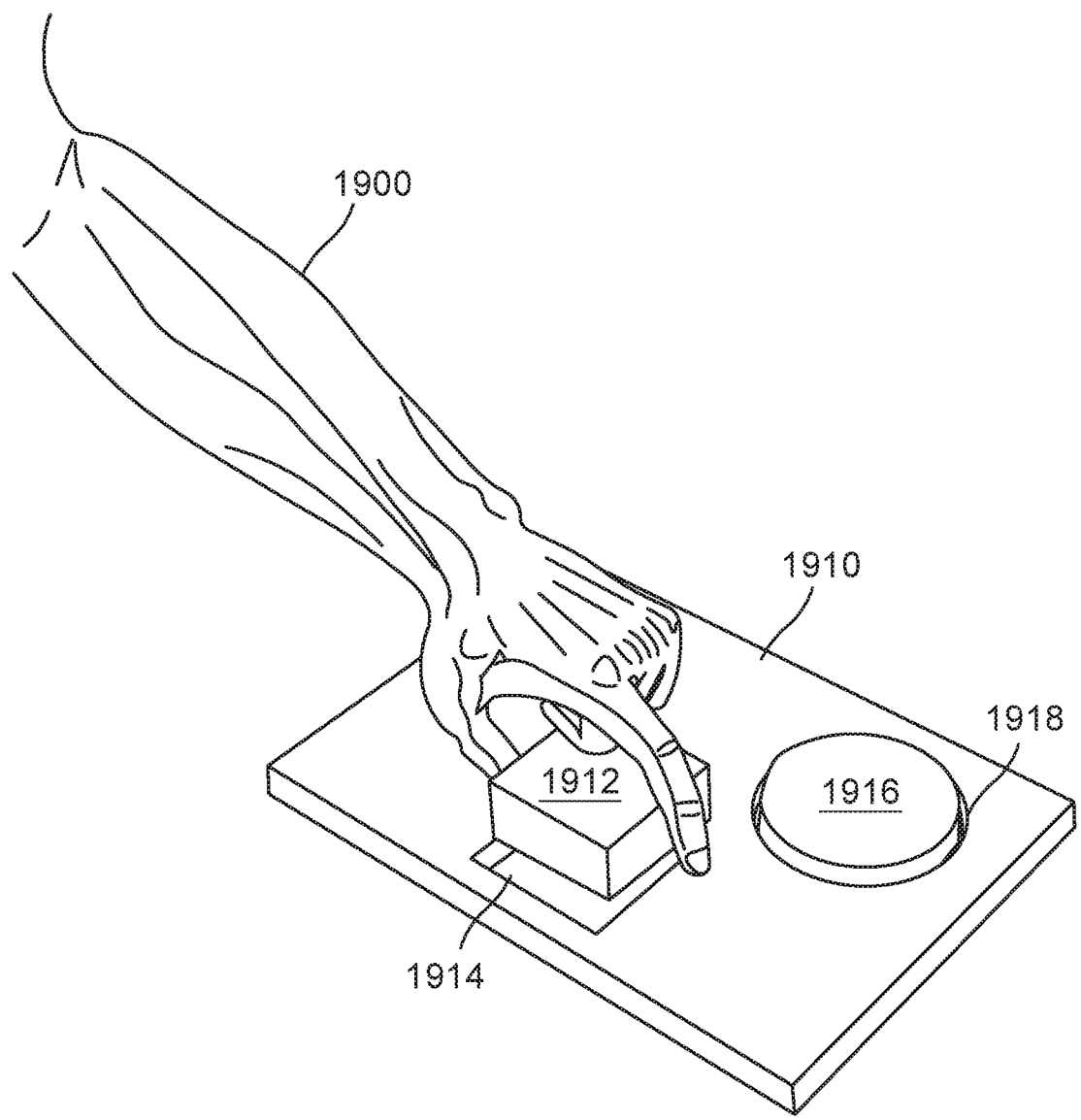
FIG. 19 illustrates an example of a pre-movement and action exercise game in which the user uses a virtual body part to select and move blocks.

Referring now to FIG. 19, an example of a pre-movement and pre-action exercise game (PEG) is illustrated as displayed to the user using display device 106 (not shown). The user is instructed to use virtual body part 1900 to select and move parts of a virtual block game 1910. The user controls virtual body part 1900 to select blocks 1912, 1916 and place them into corresponding recesses 1914, 1918, respectively. Virtual game 1900 is an example of the user being instructed to apply a rule (e.g., matching the block shape 1912 with a shape of recess 1914) and a condition to be met (e.g., placing block 1912 into recess 1914).

One or more default virtual body parts may be pre-programmed and stored in a memory structure such as memory 118, as discussed above, for use with the aforementioned methods and system. Each pre-programmed interactive and controllable virtual body part is a digital anatomical virtual extremity, synonymously limb, body part, or full body (DAVE). DAVEs may be stored on any digital device and, combined with the user's input controls of the DAVEs presented and displayed, for interactive user controlled/directed purposeful simulated physical movements. Rehabilitation and/or therapy for users with ABI as described herein may include use of DAVEs. DAVEs may be utilized with any digital device for providing user therapy. DAVE's may be one form of the UCIs utilized to play pre-action exercise games (PEGs) as described hereinabove.

The methods and system described herein provide a new therapy by providing: (a) survivor (synonymously user) controllable digital anatomical virtual extremities (DAVEs) on any digital device/screen; (b) combining the survivors' input controls of DAVEs presented/displayed and interactively survivor-controlled/directed to make purposeful simulated physical movements; with (c) concurrent communication from controlled DAVEs to body part devices, exoskeletons, gloves and other complex multi-point interfaces thereby enabling self-administered physical movement therapies to one or more impaired or affected body parts. In this manner, survivors not only exercise brain processes in controlling and directing DAVEs but, in addition self-administer physical movement therapies or prevention to one or more body parts.

In one embodiment, DAVE's may be personally, independently and interactively survivor-controlled and directed. By interacting with DAVE's, each survivor's brain processes are exercised through the process of selecting and making command inputs resulting in virtual movements of body parts also known as purposeful, simulated physical movements of DAVEs. The simulated physical movements represent a survivor's present tense (real-time), virtually interactive anatomical movement controls and directions. Selection of and interacting with DAVEs follows each survivor's initial kinetic imagery (visualization) of each desired movement. Therefore, kinetic imagery (visualization) is instantiated by controlling/directing DAVEs to make intended, purposeful, simulated physical, movements that each survivor would make absent injury/impairment. Feedback from DAVE actions is close to feedback from actual physical actions thereby fostering improved further interactions.

Alternatively, or additionally, DAVEs may be pre-coded to include a plurality of movements such as a predetermined series of movement. This series of virtual movements is activated or initiated by a particular movement or selection made by the user. For example, in further non-limiting embodiments, pre-coded DAVEs may include interactions with other digital representations such as interactions with icons, avatars and/or other images which represent virtual extremities, body parts and/or object images. Pre-coded DAVEs are user-activated so that displayed simulated physical movements reflect the users' movement goals, but the anatomical tactics for the way, i.e. the how to make the movements, may be decided (past tense), pre-coded and/or game designed.

In one aspect, users may be presented with opportunities to conjoin DAVEs and pre-coded DAVEs in order to simulate physical movements when at least two extremities (body parts) and/or objects are involved. Non-limiting examples of conjoined DAVEs include simulating when one extremity grasps and another extremity twists (opening a closed container), operates a tool (hammers a nail, turns a screw), or key punches (as in holding a mobile phone with one hand and tapping numbers of a phone number with another hand) or any other task where at least two extremities and/or objects are involved. Thus, the conjoined embodiments described herein makes it possible for therapy/rehabilitation to include one or more DAVEs interacting with virtual images, avatars, icons and the like. The conjoined embodiment process most closely tracks and mimics what the ABI survivor could do pre-brain injury or condition and most directly exercises the brain to re-train for re-gaining/restoring brain-motor control and command of impaired extremities.

The methods, system and systems described herein are directed to assisting survivors of acquired brain injury (ABI), traumatic brain injury (TBI), autism spectrum disorder, focal dystonia and other brain-affected individuals by providing, on any digital device which may present or display to users, a combination of DAVEs in any of many forms. By non-limiting example, DAVEs may represent:

a single, interactively controllable virtual extremity representing the users affected physical extremity;

multiple, interactively controllable virtual extremities representing the users affected physical extremities;

a single interactively controllable virtual extremity representing the user's unaffected physical extremity;

multiple, interactively controllable virtual extremities representing the users unaffected physical extremities;

single or multiple virtual extremities representing both the user's affected and unaffected physical extremities, being programmed to make simulated physical movements according to a design and purpose.

DAVEs may be personally, realtime, interactively and tactically controlled and/or directed by users to make custom-user-purposed simulated physical movements.

In a further non-limiting embodiment, the methods and system described herein may present or display conjoined forms of DAVEs to simulate physical movements by the user's present tense actions, controls, and/or directions, which instantiate each user's personal kinetic imagery. This kinetic imagery instantiation is triggered by controlling/directing virtual DAVEs. The use of pre-coded DAVEs is to cause a simulated movement goal to be reached. The particular manner a movement goal may be reached may be pre-coded so that the user's input action is simply to select the movement. That is to say, how the movement goal is reached follows computer coder's purpose and design (e.g., the software design), not the purpose of the user. The end use of any DAVE is to re-train/restore brain-to-extremities-communications to impaired physical extremities in order to achieve functional utility. Each user controls at least one virtual body part DAVE to simulate the kinds of physical movements/functions desired to be made by the user.

ABI survivors have a major, pervasive problem, i.e. how to re-learn to control disabled physical extremities before/without being able to move them. Since survivors cannot partially or totally physically move impaired extremities, DAVEs represent and provide, in effect, a neuroprosthetic platform for brain exercises and games which makes it possible to exercise the brain processes specific to motor (physical) movements. The brain, as the command and control organ of the human body, acquires communications links to the body exceedingly specifically: for example, learning to play any of Mozart's 27 piano concertos does nothing to execute one's tennis backhand or improve golf putting accuracy.

As a non-limiting example embodiment of the conjoining aspects of DAVEs, consider the task of opening a jar. To remove a virtual lid from a virtual jar, a user with a disabled left hand would use his unaffected right hand to direct inputs to control the DAVE of an unaffected right hand to grasping the virtual jar and inputs to control a DAVE of the virtual left hand (the user's affected physical hand), to twist/remove the virtual lid from the virtual jar. This simulated task could be accomplished with any combination of directly controlled DAVEs and pre-coded DAVES. The jar opening tasks is merely exemplary; embodiments of the methods and system described herein may include simulation of any extremity task or movement.

In a non-limiting embodiment, conjoining interactively controlled single or multiple DAVEs, and/or pre-coded movement, single or multiple DAVEs to simulate purposeful physical re-training movements is supported by at least the following:

learning/training to make purposeful physical movements requires personal, brain-to-extremities (including core body) processes;

no one can physically train for the impaired patient;

movement is idiosyncratic notwithstanding the goals of movements being universal (e.g., walking is universal, each person's walk is distinctive);

if one suffers ABI or is otherwise brain-to body-affected-impaired, physical movements are, figuratively, brain-to-disabled extremity(ies) which are "off-line", the damaged brain no longer communicates as it did to the extremities pre-injury;

users must re-train (by definition, idiosyncratically to move i.e. to control extremities);

no one can virtually, physically re-train for the impaired patient;

movement-impaired individuals can be assisted, receive therapy and engage in rehabilitation, i.e. to re-train to move extremities they cannot move; and PEGs/DAVEs are an effective re-training and movement-impaired individuals may be to move track/mimic an original training to move, i.e. particular brain-to-extremities processes.

ABI survivors (synonymously users) who cannot move extremities and choose to use PEGs/DAVE retraining will control virtual images as close as possible to physical and/or occupational brain-to-impaired-extremity rehabilitation processes. In an aspect, DAVEs may be constructed by storing user anatomical and physiological data in a database; and creating user-controllable/directed DAVE images based on a body model derived from the users' anatomical and physiological data or by using generic body models. In this manner, a DAVE may be customizable to a user. DAVEs may also be computer pre-programmed so that, by non-limiting example, any user's inputs result in simulated physical movement, or series or movements, by either or both virtual affected or unaffected hands.

DAVEs may be constructed as specialized computer digital multimedia packages capable of receiving and processing digital inputs and generating visual and/or audio outputs for display and/or presentation to a user via a digital device. In some embodiments, the user may customize a DAVE's multimedia output, such as audio (including musical) or visual preferences.

The described embodiments operate in a different combination of virtual and physical environments in that they enable communications from each survivor's control of DAVEs (in the play of PEGs) through a digital or other device to a body part device 128, which in a non-limiting example may be a physical exoskeleton, a powered orthotic device, a glove, and/or another complex multi-point interface (etc.), placed on (i.e. connected, affixed, attached and so forth to) a survivor's affected body part. In an aspect, the body part device exoskeleton is on the body part corresponding to the particular DAVE(s) being controlled by the survivor. As the DAVEs are survivor-controlled, the exoskeleton (etc.) device may be activated to physically manipulate each survivor's affected body part, thereby producing self-administered physical/occupational therapeutic manipulations to the survivor's affected body part. DAVEs may be used, for non-limiting example, with any prosthetic, orthotic and/or any motile instrument, device and the like and thereby, in lessening the onset of blood clots, contribute to rehabilitation and prevention.

Turning again to the drawings, FIGS. 20-23A illustrate one example embodiment of a retraining system that can utilize DAVEs as the virtual body image of PEGs. FIGS. 20-23A in combination with FIGS. 1 and 2, illustrate one embodiment of a system 100 employing DAVEs as the virtual body part displayed in PEGs. In one embodiment, a DAVE 2000 is illustrated in combination with output to a user worn output device, such as body part device 128 illustrated as a glove, which can provide physical stimulation to the user 120 (such as movement or vibration) simultaneously with the DAVE display of the user's affected extremity or target body part 150.

Figure 20:
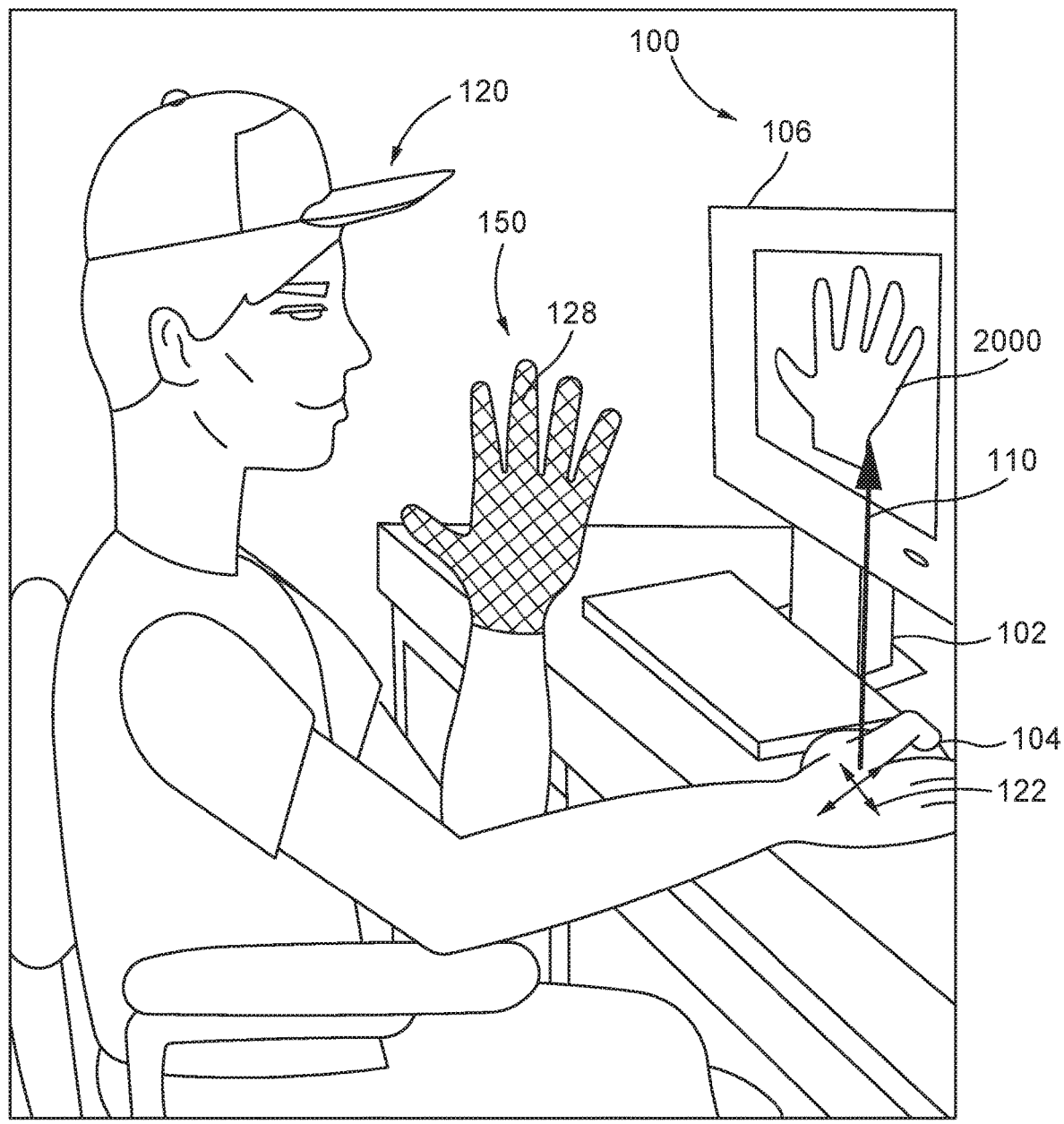
FIGS. 20, 21, 22, and 23A illustrate an example operation of the system and method of the disclosure.

FIGS. 20-23A each illustrates a user 120 interacting with training system 100. Training system 100 includes computer device 102, input device 104, and display device 106. Computer device 102 includes memory 118 (not shown) having instructions stored therein for the execution of one or more Pre-Action Exercise Games ("PEGs"). PEGs provide ABI/TBI survivors with brain stimulating substitutes for actual physical-action feedback. PEGs utilize, create and display one or more controllable digital anatomical virtual extremities (DAVEs). A DAVE is illustrated in FIG. 20 as left hand image 2000 displayed on display device 106. In FIG. 20, user 120 is providing therapy to an impaired extremity or target body part 150 illustrated as the user's left hand. User 120 uses an unimpaired limb to manipulate input device 104 illustrated as the user's right hand shown manipulating an input device 104. Input device 104 is illustrated as a computer mouse device, but may encompass at least any input device described hereinabove. In an aspect, the DAVEs may be constructed by storing, in memory 222 a user's anatomical and physiological data in a database; and creating user-controllable/directed DAVE images based on a body model derived from the users' anatomical and physiological data. Alternatively, DAVEs may be constructed using generic body part models stored in memory 224. Any DAVE constructed based upon stored generic body part modes may be further customized to a user based upon the users' anatomical and physiological data. In this manner, DAVEs may be customizable to a user 120 and realistically reflect target body part 150.

As illustrated in FIGS. 20-23A, both a survivor's (e.g., user 120) physical impaired left hand (e.g., target body part 150) and a left hand DAVE (e.g., virtual image 2000) controllable by the survivor to simulate the survivor's desired purposeful movements where DAVEs are generated by a specially programmed controller, processor, or computer (e.g., computer 102), and displayed to the survivor/user on a visual display device (e.g., display screen 106.) The computer device 102 also is arranged to receive input from a survivor/user via, for example, a mouse (e.g., input device 104, or keyboard input, or survivor brain-computer interface signals (not shown) and utilize these input signals to control or affect changes in the displayed DAVE characteristics.

As also illustrated in FIGS. 20-23A, user 120's physical impaired left hand (e.g., target body part 150) is illustrated, in an aspect, as attached to body part device 128. In an aspect, body part device 128 may be, but is not limited to being, output devices such as a robotic arm, shoulder, or other limb, a prosthetic limb, a user worn device such as an exoskeleton, a powered orthotic device, or a glove, sleeve, or sock, or the like. Regardless of form, body part device 128 may include motor means allowing articulatable mechanical motion which reflects or corresponds to DAVE motion. Body part device 128 may also include means allowing receipt and processing of signals 132 (FIG. 1) from computer device 102. Signals 132 may cause the external body part device 128 to move by controlling the motor means move the body part device substantially in unison with the movement action of the DAVE concurrently displayed on display device 106.

In some examples, the external body part device 128 may stand alone and be placed in a location viewable by the user 120. When body part device 128 is not attached to user 120, the body part device can serve as an additional output display. When utilized as an additional output display, the mechanical motion of the body part device directed by control signals allowing the user to visualize a three-dimensional physical motion of the DAVE displayed motion.

When body part device 128 is attached to a user's target body part 150, the body part device motion provides actual physical actions and movement to the user's impaired extremity or target body part 150, so that the user receives feedback via sensory-action return signals from the training system 100. In this manner, the methods and system described herein may provide a combination of cognitive pre-action training and impaired extremity movement training and prevention contemporaneously.

In an additional or alternative aspect, body part device 128 may be configured to receive one or more control signals from computer device 102, as described above in relation to FIG. 2, corresponding to the virtual movement of the virtual body part or DAVE being manipulated by user 120. Based on the one or more control signals, the body part device 128 may process the control signals and may stimulate one or more target body parts 150 of the user 120 (or of a non-user (not shown)) to prompt movement of one or more body parts, which may include target body part 150.

In the aspect illustrated in FIGS. 20-23A, body part device 128 is embodied as a glove device (not separately shown). A glove device, synonymously motorized orthotic device of any composition, for use with system 100 as body part device 128 includes one or more digital stepper motors that may receive signals generated by computer 102 that reflect user-directed DAVE motion and are translated into motor control signals. In an aspect, the motors may be attached to or embedded within the glove device. In an aspect, the motors may control wires attached to or embedded in the glove device to contract or extend in an articulatable manner that contracts or extends finger portions of the glove. In this manner, the glove device may contract or extend, selectively, one or more of the glove fingers enabling the glove device to move the user's impaired hand to a variety of positions. The glove device may be constructed from any soft flexible fabric or material, including additive manufacturing materials (e.g., 3-dimensional printed materials), or any combination of materials. In one aspect, the glove device may include reinforced materials, such as plastics or rubbers, in non-articulating areas such as the palm, finger lengths, or finger tips, combined with softer materials in areas of articulating joints. Glove device may also include one or more vibrating outputs to the body part device and sensing devices for sensing positioning and motion, and include a transmission means for communicating positioning signals to computer device 102. Alternatively, or in addition, glove device may include one or more electrode devices, such as transdermal electrodes or other neuro-stimulation electrodes, for additional electro-stimulation of a user's target body part 150. In this aspect, target body part stimulation signals may be communicated by computer 102 in addition to movement signals so that body part device may additionally or alternatively provide electro-stimulation therapy.

Operation of the aspect illustrated in FIGS. 20-23A will now be described. In FIG. 20, system 100 is initialized to select and load the appropriate PEGs and to display either a default or user customized DAVE to user 120. As illustrated, user 120 initiates therapy to an impaired left hand as the target body part 150. Body part device 128, a therapy glove as described above, is securely attached to the user's target body part 150. User 120 utilizes a non-impaired body part to manipulate an input device 104, illustrated as the user's right hand manipulating a computer mouse. DAVE 2000 visually simulates an aspect of the user/survivor's left hand physical movement and, as illustrated, DAVE 2000 exhibits an open left hand arrangement.

In FIG. 20, as the user manipulates input device 104 to control illustrated DAVE 2000 displayed on display 106, user 120 creates motion inputs or physical inputs 122 (FIG. 1) into input device 104. Physical inputs 122 are processed and forwarded to computer device 102 as input signals 110 (FIG. 1) and represented by the arrow 110 in FIG. 20.

Figure 21:
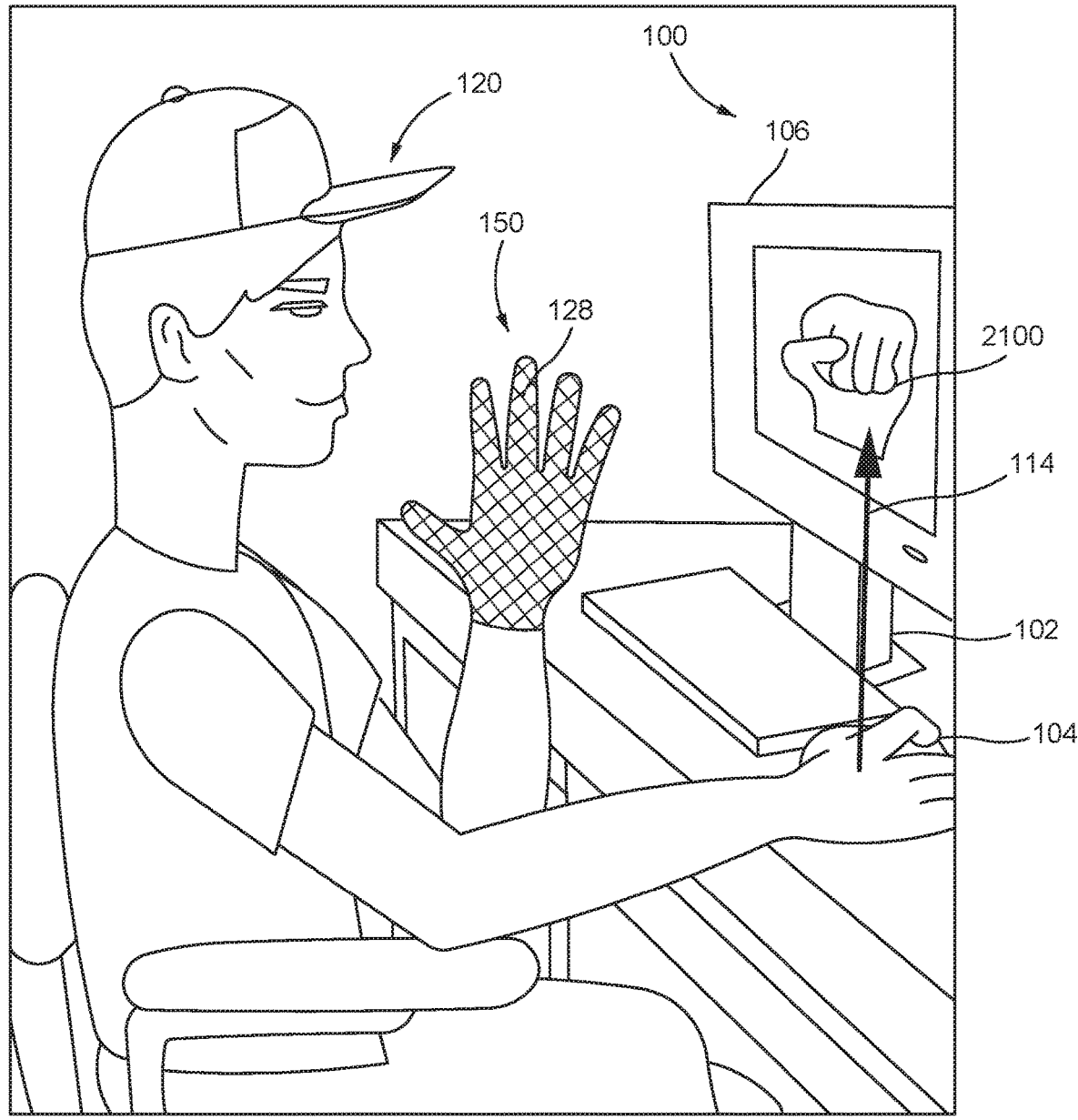

In FIG. 21, computer device 102 has received user input signals 110 and processed the user's input signals to reflect signal 114 (FIG. 1) output to the display device 106 and illustrated in FIG. 21 as arrow 114. In FIG. 21, display device 106 now shows DAVE 2100 in a different configuration. DAVE 2100 is used to exhibit a closed left hand or fist arrangement.

Figure 22:
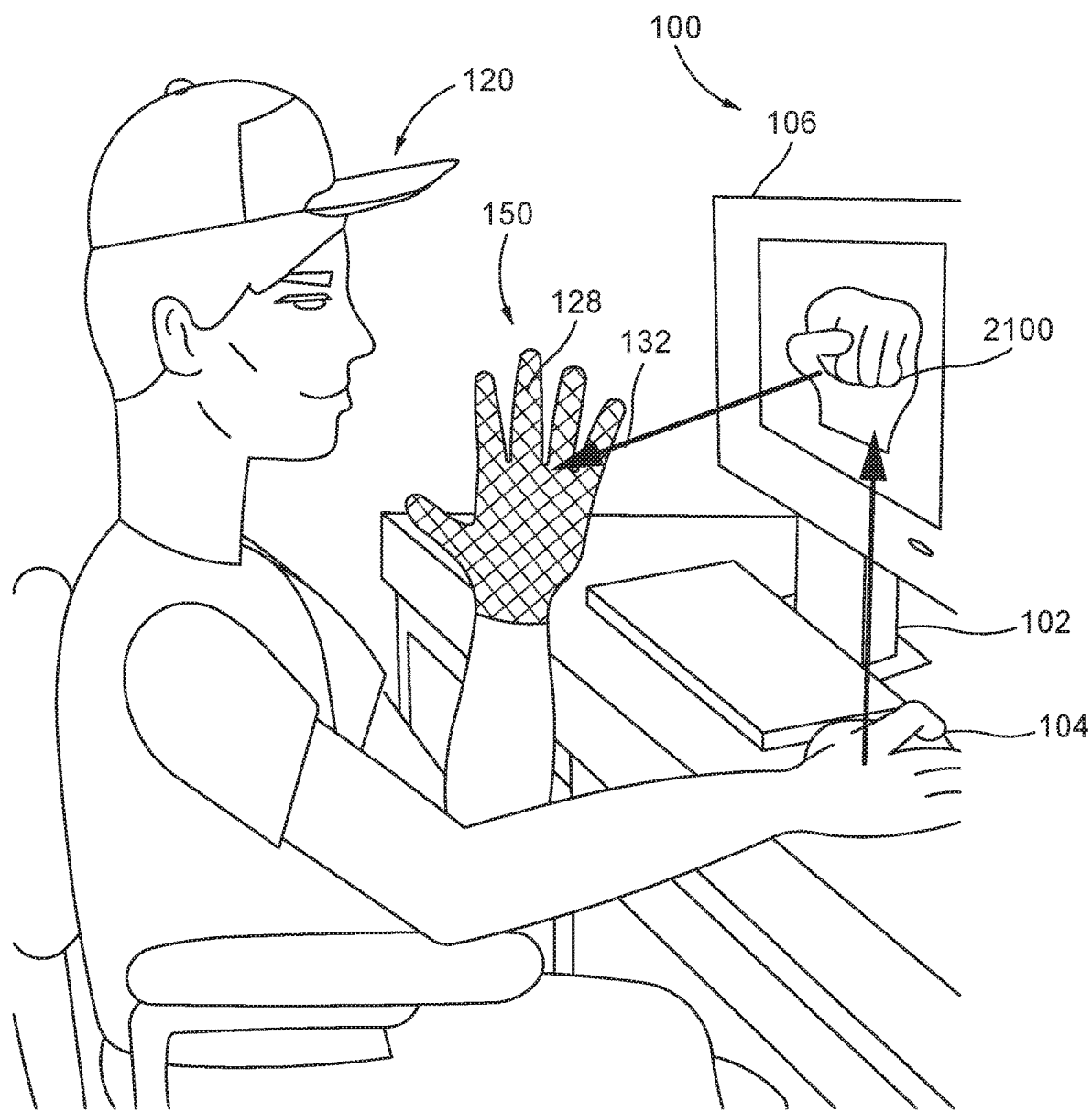

In FIG. 22, computer device 102 transmits signal 132 (FIG. 1), illustrated in FIG. 22 as arrow 132, to body part device 128 for controlling body part device 128. Signal 132 is transmitted concurrently or substantially simultaneously with the device 106 displaying DAVE 2100 simulated left hand physical movement, the computer device 102 also transmits signals, by electrical signal (wired or unwired), or sound communication, or other transmission technology, to body part device 128.

Figure 23A:
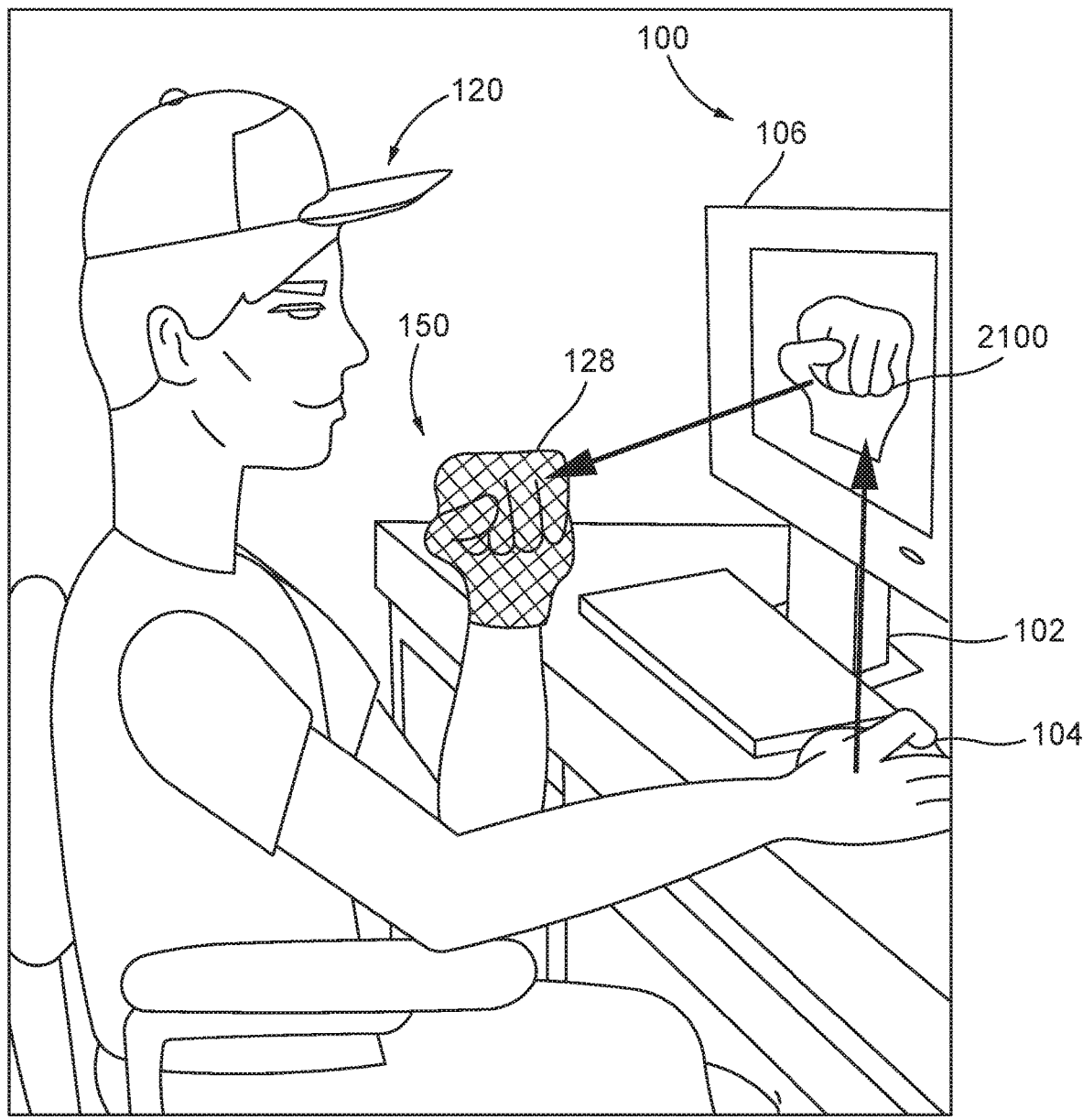

FIG. 23A illustrates body part device 128 receiving signal 132 from computer device 102 and performing a corresponding signal directed movement. FIG. 23A illustrates body part device 128, embodied in FIGS. 20-23A as a user worn glove, has moved from an open left hand arrangement illustrated in FIGS. 20-22 to physically move target body part 150 into a closed left hand or fist arrangement as shown in FIG. 23A.

In an aspect, display device 106 may be a digital, holographic or other display device that displays the DAVE's simulated or virtual left hand physical movement. Additionally, in an aspect left hand body part device 128 may be an exoskeleton, a powered orthotic, a glove and/or other complex multi-point interface (collectively a "hand device") that is physically attached or associated with the survivor/user's impaired hand. Signals 132 may direct the movement of the hand device such that the hand device mimics the movement or action being displayed by the DAVE. In this manner, as the survivor-controlled DAVE hand opens and closes, the hand device attached to or associated with the survivor's impaired hand also physically opens and closes the survivor's physical left hand (fingers, thumb and or wrist in any combination). As can be seen, as the survivor plans and executes changes to the DAVE on the display device, they are presented with the DAVE changing and substantially simultaneously presented with a physical self-directed motion the impaired hand.

In an aspect, the computer device 102 may include a graphic user interface which enables a user to control the on-screen DAVE.

In an aspect, the DAVE control signals 110 originate with the user operating a standard computer mouse (or any input device 104) to input signals to the computer device 102.

In an aspect, the DAVE control signals are processed by computer device 102 for display on display 106, and sent from the computer device 102 to a DATEQ™ device (not shown) or similar data acquisition circuitry capable of providing the appropriate signal conversion from the output of the computer device to the input of the HD. For example, if the computer device output is USB and the hand device utilizes a serial signal input, a DATEQ™ can be utilized for signal conversion. Appropriate power sources for circuitry are available.

In an aspect, DAVE control signals utilized to drive the display device and concurrently or simultaneously output from the computer device to the hand device can be sent to an ARDUINO™ (or other suitable circuit board) and used to control the hand device movement via one or more digital motors or other motion producing devices. In an aspect, one or more stepper motors such as micro stepper motors may be utilized to affect hand device motion. Any suitable communications and control software enabling system component communications and control between the system computer device and peripheral devices may be utilized as required. Further, appropriate power sources are connected to all circuitry and motors. In an aspect, batteries or other power source may be embedded in the hand device.

Thus, in one embodiment, the computer device 102 passes signals to the hand device (either through a DATEQ™ arrangement, an ARDUINO™ arrangement, (or other similar circuitry)) to open or close the user's impaired physical hand in a manner corresponding to the user's inputs to open or close a left hand DAVE displayed to the user. In this manner, a user of the methods and system described herein may self-administers physical movement therapies or preventions to one or more impaired or target body parts.

Referring back to FIG. 16B and tele-rehabilitation system 1650, a therapist may use a therapist machine 1652a, 16652b and 1652c and may remotely observe a user of a user machine 1600a, 1600b, 1600c and 1600d, and may remotely interact therewith and/or provide assistance, input, instructions, therapy, healthcare and/or other services thereto. In an aspect illustrated in FIG. 23B, for example, a therapist machine, such as therapist machine 1652c may be configured with a measurement device, such as a measurement left-hand glove device 108b (depicted from a back of hand perspective in FIG. 23B), wherein measurement glove device 108b may be worn by a remote therapist to interact with a user via therapist machine 1652c and network 1626, to physically assist the user and/or demonstrate to the user an interaction with a user machine, such as for example, user machine 1600b. A therapist may, for example, demonstrate via an audio/visual connection and/or via a glove device to glove device connection, a proper movement, or play of a game, such as play of a PEG or a proper movement in an interaction with a DAVE. FIG. 23B depicts a portion 1650a of system 1650 wherein therapist machine 1652c is configured with measurement glove device 108b and user machine 1600b is configured with a left-hand glove body part device 128b (depicted from a back of hand perspective in FIG. 23B), wherein a therapist wearing measurement glove device 108b may manipulate and move their left hand and such manipulation and movements may be measured by measurement glove device 108b and data associated with such manipulation and movements may be captured and transmitted by therapist machine 1652c to user machine 1600b which may, using received data, send signals to left-hand glove body part device 128b worn by a user causing left-hand glove body part 128b to mimic such manipulation and movements, thereby enabling the therapist to remotely interact with the user, physically assist the user and/or demonstrate to the user an interaction with user machine 1600b, such as for example, demonstrate a proper movement in an interaction with a DAVE (where a DAVE on user machine 1600b may also be displayed on therapist machine 1652c, and may mimic changes thereto in response such manipulation and movements), or play of a game, such as play of a PEG. It should be appreciated that it is not necessary for the therapist and the user to exercise using the same handedness. That is, a left handed therapist may demonstrate to a right handed user, with the intervening computer providing mirror image communication reversal. Left- and right-hand body part devices as well as left- and right-hand measurement glove devices may be freely intermixed, potentially direct- or cross-coupled and inter-communicated without either human having to adjust.

FIG. 23C depicts a portion 1650b of system 1650 wherein user machine 1600b is configured with a left-hand glove body part device 128b (depicted from a back of hand perspective in FIG. 23C) and with a right-hand measurement glove device 108a (depicted from a back of hand perspective in FIG. 23C), wherein a user of user machine 1600b may wear both left-hand glove body part device 128b right-hand measurement glove device 108a in order to have manipulation and movements made with an unimpaired right hand mimicked on an impaired left hand. In operation, manipulation and movements of the user's right hand may be measured by measurement glove device 108a and data associated with such manipulation and movements may be captured by user machine 1600b which may send signals to left-hand glove body part device 128b causing left-hand glove body part 128b to mimic such manipulation and movements, thereby a user to have manipulation and movements made with an unimpaired right hand mimicked on an impaired left hand. In an aspect, display 1610b may display a left-hand DAVE and a symmetrical right-hand DAVE and a user may be instructed to attempt symmetrical operations, manipulations and/or movements with their unimpaired right hand and impaired left hand.

In the example embodiment of system portion 1650b of tele-rehabilitation system 1650 a therapist may be remotely connected to user machine 1600b via network 1626 and provide assistance, guidance and the like. FIG. 23D depicts a standalone embodiment of a system 100a comprising a computer device 102a configured with a left-hand glove body part device 128b (depicted from a back of hand perspective in FIG. 23D) and with a right-hand measurement glove device 108a (depicted from a back of hand perspective in FIG. 23D). System 100a may be stand alone and not networked in a tele-rehabilitation system, a may, in an aspect, be configured to display a left-hand DAVE and a symmetrical right-hand DAVE and instruct a user to attempt symmetrical operations, manipulations and/or movements with their unimpaired right hand and impaired left hand. While such an embodiment may not provide a user with access to an interactive therapist, it may still provide a mimicking operation of an unimpaired body part and an impaired body part and provide a service that is less costly to deliver than that of a labor intensive personal service comprising an interactive therapist.

In an aspect, a networked environment of user machines 1600 as shown in tele-rehabilitation system 1650 of FIG. 16B, may be used to provide an online community of ABI/TBI affected users comprising impaired body parts. Such a networked environment may be configured to be usable by users to engage in competitive game-play, cooperative game-play and/or other interactions with other users which may provide therapeutic benefit to users of the system. In some embodiments, the users may interactively and competitively play games. Yet in other embodiments, the users may interactively and cooperatively play games. In an embodiment, game-play may be between two users. In an embodiment, game-play may be between more than two users. In an embodiment, game-play may be between two teams of two or more users each. In an embodiment, game-play may be between more than two teams of more two or more users each. In an embodiment, game-play may be enhanced and/or rewarded by transmitting music to networked user machines 1600 engaged in game-play.

FIG. 23E depicts a portion 1650d of system 1650 wherein therapist machine 1652c is configured with measurement glove device 108b and user machine 1600b is configured with a left-hand glove body part device 128b (depicted from a back of hand perspective in FIG. 23E), wherein a therapist wearing measurement glove device 108b may manipulate and move their left hand and such manipulation and movements may be measured by measurement glove device 108b and data associated with such manipulation and movements may be captured and transmitted by therapist machine 1652c to user machine 1600b which may, using received data, send signals to left-hand glove body part device 128b worn by a user causing left-hand glove body part device 128b to mimic such manipulation and movements, thereby enabling the therapist to remotely interact with the user, physically assist the user and/or demonstrate to the user an interaction with user machine 1600b, such as for example, demonstrate a proper movement in an interaction with a DAVE (where a DAVE on user machine 1600b may also be displayed on therapist machine 1652c, and may mimic changes thereto in response to such manipulation and movements), or play of a game, such as play of a PEG. User machine 1600b and therapist machine 1652c may both be configured with a virtual reality (VR) headset display 106a and 106b, respectively, and may provide a user immersive rehabilitation experience, wherein a DAVE, a PEG and or other aspects of a rehabilitation, healthcare or other operation may be displayed in a user immersive manner.

FIG. 23F depicts a portion 1650d of system 1650 wherein user machine 1600b is configured with a left-hand glove body part device 128b (depicted from a back of hand perspective in FIG. 23F) and with a right-hand measurement glove device 108a (depicted from a back of hand perspective in FIG. 23F), wherein a user of user machine 1600b may wear both left-hand glove body part device 128b and right-hand measurement glove device 108a in order to have manipulation and movements made with an unimpaired right hand mimicked on an impaired left hand. In operation, manipulation and movements of the user's right hand may be measured by measurement glove device 108a and data associated with such manipulation and movements may be captured by user machine 1600b which may send signals to left-hand glove body part device 128b causing left-hand glove body part 128b to mimic such manipulation and movements, thereby allowing a user to have manipulation and movements made with an unimpaired right hand mimicked on an impaired left hand. In an aspect, display 1610b may display a left-hand DAVE and a symmetrical right-hand DAVE and a user may be instructed to attempt symmetrical operations, manipulations and/or movements with their unimpaired right hand and impaired left hand. User machine 1600b may be configured with a virtual reality (VR) headset display 106a and may provide a user immersive rehabilitation experience, wherein a DAVE (and/or a left-hand DAVE and a symmetrical right-hand DAVE), a PEG and or other aspects of a rehabilitation, healthcare, tele rehab or other operation may be displayed in a user immersive manner. In the example embodiment of system portion 1650d of tele-rehabilitation system 1650 illustrated in FIG. 23F, a therapist may be remotely connected to user machine 1600b via network 1626 and provide assistance, guidance, instruction and the like.

FIG. 23G depicts a standalone embodiment of a system 100b comprising a computer device 102a configured with a left-hand glove body part device 128b (depicted from a back of hand perspective in FIG. 23G) and with a right-hand measurement glove device 108a (depicted from a back of hand perspective in FIG. 23G). System 100b may be stand alone and not networked in a tele-rehabilitation system, and may, in an aspect, be configured to display a left-hand DAVE and a symmetrical right-hand DAVE and instruct a user to attempt symmetrical operations, manipulations and/or movements with their unimpaired right hand and impaired left hand. System 100b may be configured with a virtual reality (VR) headset display 106a and may provide a user immersive rehabilitation experience, wherein a DAVE (and/or a left-hand DAVE and a symmetrical right-hand DAVE), a PEG and or other aspects of a rehabilitation, healthcare or other operation may be displayed in a user immersive manner. While such an embodiment of system 100b may not provide a user with access to an interactive therapist, it may still provide an immersive mimicking operation of an unimpaired body part and an impaired body part and provide a service that is less costly to deliver than that of a service comprising a labor intensive interactive therapist.

Figure 24:
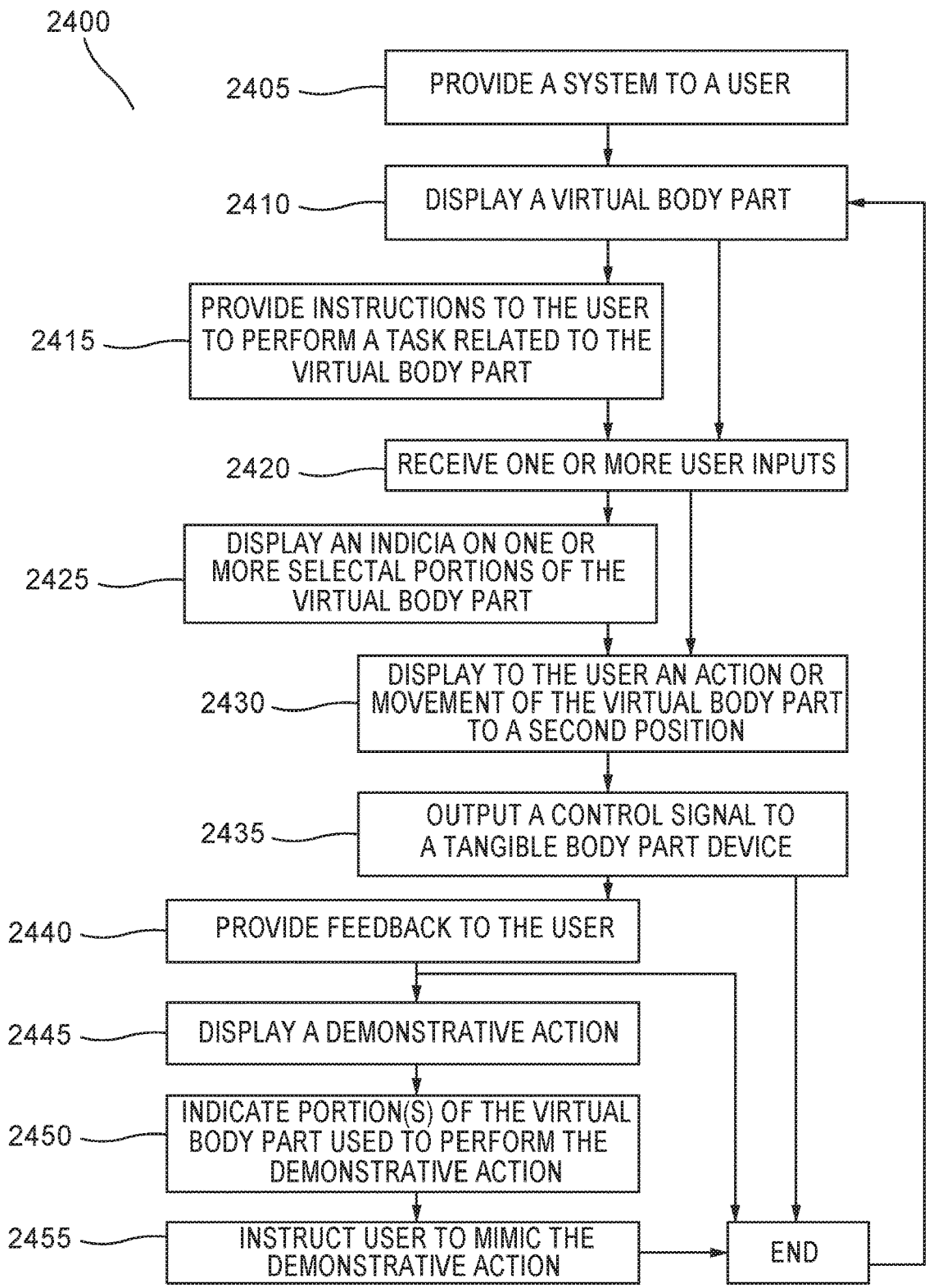
FIG. 24 illustrates a flow chart of one embodiment of a method of the disclosure.

Referring now to FIG. 24, a flowchart illustrates blocks in one embodiment of a method 2400 of pre-movement and action self-training/self-learning. Method 2400 is discussed with additional reference to FIGS. 1-24 above. In block 2405, system 100 is provided to a user. In one embodiment, system 100 includes a computer device 102, a display device 106 disposed in communication with computer device 102, and input device 104 disposed in communication with computer device 102 as discussed above. In another embodiment, system 100 also includes feedback device 130 and/or body part device 128 disposed in communication with the computer device 102. In another embodiment, system 100 optionally includes feedback device 130.

In block 2010, system 100 displays to a user a virtual body part. In one embodiment, the virtual body part is selectable or includes at least one selectable body part portion shown on display device 106 in a first position or configuration.

In block 2415, system 100 optionally provides an instruction to the user to perform a task related to the virtual body part. In some embodiments, the instruction is self-evident, is provided in an instruction manual, is provided verbally by a therapist or other person, or is provided in some other form. In one embodiment, the task includes moving the virtual body part in virtual 3D space, changing the position of the virtual body part or the at least one selectable body part portion to a second position in virtual 3D space, changing the configuration of the virtual body part, moving an object in virtual 3D space, grasping a virtual object, touching a virtual object, aligning the virtual body part with a virtual object or displayed reference point, positioning the virtual body part relative to a virtual reference point such as a displayed target, using the virtual body part to select a virtual object, releasing an object, rotating at least a portion of the virtual body part in virtual 3D space, or selecting one object among a plurality of displayed objects. In one embodiment, the task includes the user identifying a condition to be met and/or application of a rule, where the user input includes or demonstrates application of the rule or identifying the condition to be met.

In block 2420, system 100 receives one or more user inputs from the user. The user input can include a selection input in response to the instruction. In one embodiment, the instruction input is associated with the virtual body part or with one or more portions of the virtual body part. Alternately or additionally, the user input is a movement and action input associated with one or more portions of the virtual body part or with the entire virtual body part. In one embodiment, block 2420 includes detecting a biomarker of the user. In one embodiment, block 2420 is performed by input device 104, which may be user movement and action recognizing component 124, described hereinabove with reference to FIG. 1.

In one embodiment, user measurement device 108 obtains a user measurement or signal, such as a neurological signal of the user, measurement of a biological substance of the user, or detection of a biomarker. System 100 optionally compares the user measurement or signal to a control value.

In optional block 2425, system 100 displays to the user, in response to the user input, some indicia 1716 associated with one or more selectable portions of the virtual body part. As discussed above, for example, with reference to FIGS. 17A and 17B, indicia 1716 includes color, shading, intensity, a marking, a symbol, or any device that communicates to the user that a selectable portion can be selected or that a selectable portion has been selected.

In block 2430, system 100 displays to the user a movement and action or movement of the virtual body part (or one or more portion thereof) to a second configuration based on the user input(s). In one embodiment, the user input(s) is (are) at least a part of pre-movement and pre-action self re-training/re-learning by the user to make physical movements.

In one embodiment, method 2400 includes block 2435 of system 100 outputting a control signal to a tangible body part device 128. Here, block 2405 includes providing a system having the body part device 128 disposed in communication with computer device 102. As discussed above, examples of body part device 128 include an output device such as a prosthetic limb or body part, a robotic device, powered orthotic device, or other tangible and operable device. In one embodiment, the body part device 128 is operationally connected to the user. In another embodiment, the body part device 128 is not connected to the user, such as a prosthetic or robotic device positioned adjacent to the system 100 or to the user.

When system 100 includes feedback device 130, method 2400 optionally includes block 2440 of providing feedback to the user. In one embodiment, the feedback is an electrical signal configured to stimulate a muscle or nerve of the user (e.g., a neurological signal), tactile feedback (e.g., via a haptic device), visual feedback, demonstrative feedback (e.g., demonstrated movement and action using a virtual body part or a tangible body part device), audio feedback, or an electrical signal configured to control a tangible body part device disposed in communication with system 100. When the feedback is an electrical signal configured to control a tangible body part device, the body part device preferably is connected to the user. In one embodiment, the electrical signal contemporaneously causes the tangible body part device to substantially perform the movement and action performed by the user-controlled virtual body part.

In one embodiment, method 2400 optionally includes blocks 2445-2455. In block 2445, system 100 displays a demonstrative movement and action of the virtual body part. For example, system 100 shows a virtual body part moving a hand from an open position to a closed position.

In block 2450, system 100 indicates to the user one or more portion of the virtual body part that is used to perform the demonstrative movement and action. For example, system 100 displays in a different color the muscle(s) or muscle group(s) used by the virtual body part to open and close the hand or by dynamic color coding indicating those muscles(s) or muscle group(s) which should be active contrasted with those muscle(s) or muscle groups(s) that should be relaxed. In block 2450, system instructing the user to mimic the demonstrative movement and action. The instruction may be presented to the user by an on-screen message, audible command, or other means of communication.

Figure 25:
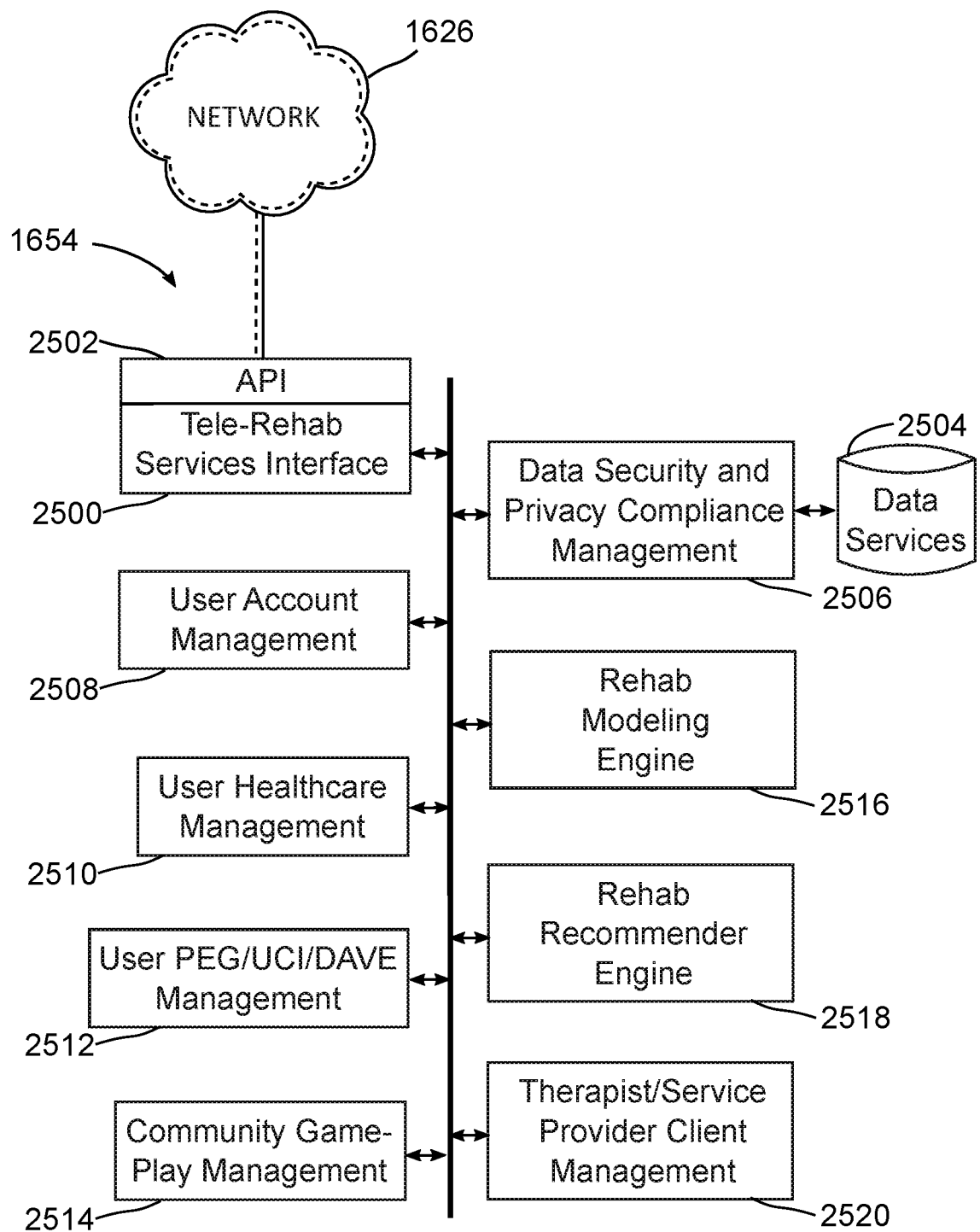
FIG. 25 illustrates an example block diagram of a server based system of the tele-rehabilitation system of FIG. 16B.

In block 2455, in response to instructing the user to mimic the demonstrative movement and action, system 100 receives a user input corresponding to the portion(s) of the virtual body part used to perform the demonstrative movement and action. For example, the user selects the muscle group used to close the hand. In response to the user input, system 100 displays the demonstrative movement and action. FIG. 25 depicts an example block diagram of server based system 1654 of tele-rehabilitation system 1650 of FIG. 16B. Server based system 1654 may comprise one or more servers, software and data services comprising one or more databases, may be a cloud-based system and may be located in one or more physically separate locations. Server based system 1654 comprises a tele-rehabilitation services interface module 2500 which may be accessed via network 1626, and may comprise an application services interface (API) 2502 which may provide backend services for downloadable tele-rehabilitation applications (tele-rehab apps) and front-end services for web applications. Downloadable apps may offer data security advantages and where network connectivity of a user device is poor, slow and/or unreliable, downloadable apps may offer usability, responsiveness and/or performance advantages. API 2502 may also be used by third party healthcare provider systems to integrate tele-rehabilitation services into their online applications and services. Server based system 1654 may comprise data services 2504, wherein data services may comprise one or more databases and access thereto may be managed by a data security and privacy compliance module 2506. Data security and privacy compliance module 2506 may comprise various levels of logical security, including Advanced Encryption Standard (AES) published by the National Institute of Standards and Technology (NIST) for protecting data between endpoints and may be used for storage based encryption of stored data, a HIPAA compliance rules engine, a data anonymizer to strip or make inoperable data that may potentially make a user identifiable, system security and malware detection scans, validation of external intrusion vulnerability scans, and the like. In an aspect, data may be securely held via blockchain technology. Server based system 1654 may comprise a user account management module 2508, wherein a user may create (or have created) a user account within tele-rehabilitation system 1650. Data associated with user accounts may be stored within data services 2504 and a granting of access to user accounts may require successful negotiation of a multi factor authentication process and may be managed at least in part by data security and privacy compliance module 2506. Server based system 1654 may comprise a user healthcare management module which may maintain healthcare services histories, statuses, user measurement data, ongoing treatments and plans, recommended treatment plans, and the like, which may be related to tele-rehabilitation services. In the example embodiment of FIG. 25, server based system 1654 may comprise a user PEG/UCI/DAVE management module 2512 which may manage user data, parameters and/or other information and data related to a user's PEGs, UCIs and/or DAVEs. In an embodiment, user PEG/UCI/DAVE management module 2512 may be combined into user healthcare management module 2510. In an embodiment, server based system 1654 may comprise a user community game-play management module 2514 which may manage multiplayer games which may be therapeutic, entertaining and may be well suited for pre-action exercise and relearning and redevelopment of cognitive motor capabilities, including self-relearning and assisted relearning of cognitive motor capabilities. In an embodiment, server based system 1654 may comprise a rehab modeling engine 2516. Rehab modeling engine may use machine learning to determine effective predictive relationships between user data, user therapeutic treatments and user treatment outcomes and thereby establish and maintain rehab models which model the relationship between inputs of user related data and therapeutic treatments and outputs of outcomes. In an embodiment, server based system 1654 may comprise a rehab recommender engine 2518, which may evaluate outcome predictions for a user and the user's associated user data over a various potential treatment regimens and select and/or recommend optimal treatment strategies based at least in part on predicted outcomes. Selections and/or recommendations may also be made based at least in part on cost and other constraints, such as a user's available time for treatment and access to treatment equipment. In an embodiment, server based system 1654 may comprise a therapist/service provider client management module 2520. Therapist/service provider client management module 2520 may provide functionality including patient/client reviews, treatment history and analysis, patient report generation, performance and results analysis, community game-play history and analysis, diagnostic analysis, prognosis analysis, rehab recommender engine results, patient/client scheduling and planning, patient client communications, and the like.

Examples, as described herein, may include, or may operate on, logic or a number of modules or mechanisms. Modules are tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside (1) on a non-transitory machine-readable medium or (2) in a transmission signal. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, one instantiation of a module may not exist simultaneously with another instantiation of the same or different module. For example, where the modules comprise a general-purpose hardware processor configured using software, the general-purpose hardware processor may be configured as respective different modules at different times. Accordingly, software may configure a hardware processor, for example, to constitute a particular module at one instance of time and to constitute a different module at a different instance of time.

Examples, as described herein, may include, or may operate on, logic or a number of modules, modules, or mechanisms. Modules are tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside (1) on a non-transitory machine-readable medium or (2) in a transmission signal. In an example, the software, when executed by the underlying hardware of the module, causes the hardware to perform the specified operations.

Accordingly, the terms "module" and "modules" are understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, one instantiation of a module may not exist simultaneously with another instantiation of the same or different module. For example, where the modules comprise a general-purpose hardware processor configured using software, the general-purpose hardware processor may be configured as respective different modules at different times. Accordingly, software may configure a hardware processor, for example, to constitute a particular module at one instance of time and to constitute a different module at a different instance of time.

Additional examples of the presently described method, system, and device embodiments include the following, non-limiting configurations. Each of the following non-limiting examples may stand on its own or may be combined in any permutation or combination with any one or more of the other examples provided below or throughout the present disclosure. The preceding description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

As used in this disclosure, the terms "component," "module," "system" and the like are intended to include a computer-related entity, such as but not limited to hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this disclosure and the appended claims should generally be construed to mean "one or more" unless specified otherwise or clear from the context to be directed to a singular form.

Various aspects or features will be presented in terms of systems that may include a number of devices, components, modules, and the like. It is to be understood and appreciated that the various systems may include additional devices, components, modules, etc. and/or may not include all of the devices, components, modules etc. discussed in connection with the figures. A combination of these approaches may also be used.

The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the processes described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Additionally, at least one processor may comprise one or more modules operable to perform one or more of the steps and/or actions described above.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or actions of a method or algorithm may reside as one or any combination or set of codes and/or instructions on a machine readable medium and/or computer readable medium, which may be incorporated into a computer program product.

A number of embodiments of the methods, and system herein have been described. Various modifications may be made without departing from the spirit and scope of the disclosure. For example, various forms of the flows shown above may be used, with steps re-ordered, added, or removed. Accordingly, other embodiments are within the scope of the following claims.

We claim:

1. A method for remotely improving performance of physical actions of a user with an affected brain comprising:
   providing an apparatus to the user having one or more self-teaching virtual training games stored therein that, upon execution, simulate at least one physical action using one or more controllable digital anatomical virtual extremities;
   creating the one or more controllable digital anatomical virtual extremities; each said controllable digital anatomical virtual extremity being configured to the user by storing measured user anatomical data and measured user physiological data in a database and creating an extremity model based on a model data derived from said anatomical and physiological data;
   constructing one or more pre-coded digital anatomical virtual extremities having a series of pre-determined movement actions;
   displaying on a display device the one or more controllable digital anatomical virtual extremities;
   displaying on the display device the one or more pre-coded digital anatomical virtual extremities;

receiving, from an input device controlled by the user, inputs that control a simulated physical action of the one or more controllable digital anatomical virtual extremities constructed by the apparatus conjoined with one or more of the pre-coded digital anatomical virtual extremities constructed by the apparatus;

wherein the received user inputs controlling the controllable digital anatomical virtual extremities instantiate a kinetic imagery of the simulated physical action of the user;

attaching a feedback device to a user's affected physical extremity, wherein upon a motion of the controllable digital anatomical virtual extremity representing the user's affected physical extremity on the display device, a first signal is transferred to the feedback device resulting in physical stimulation of the user's affected physical extremity, receiving, from an input device controlled by a remote therapist, a second signal that alters the motion of the controllable digital anatomical virtual extremity representing the user's affected physical extremity on the display device, wherein the second signal is transferred to the feedback device resulting in physical stimulation of the user's affected physical extremity by the therapist, and wherein the instantiation of kinetic imagery of the simulated physical action and the physical stimulation of the user's affected physical extremity are associated with improving performance of the physical actions of the user.

2. A method for remotely improving performance of physical actions of a user with an affected brain comprising:

providing an apparatus to the user having one or more self-teaching virtual training games stored therein that, upon execution, simulate at least one physical action using one or more controllable digital anatomical virtual extremities;

creating the one or more controllable digital anatomical virtual extremities; each said controllable digital anatomical virtual extremity being configured to the user by storing measured user anatomical data and measured user physiological data in a database and creating an extremity model based on a model data derived from said stored measured user anatomical and physiological data;

displaying on a display device the one or more controllable digital anatomical virtual extremities;

receiving, from an input device controlled by the user, inputs that control a simulated physical action of the one or more controllable digital anatomical virtual extremities created by the apparatus;

wherein the received user inputs controlling the controllable digital anatomical virtual extremities instantiate a kinetic imagery of the simulated physical action of the user;

attaching a feedback device to a user's affected physical extremity, wherein upon a motion of the controllable digital anatomical virtual extremity representing the user's affected physical extremity on the display device, a first signal is transferred to the feedback device resulting in physical stimulation of the user's affected physical extremity, receiving, from an input device controlled by a remote therapist, a second signal that alters the motion of the controllable digital anatomical virtual extremity representing the user's affected physical extremity on the display device, wherein the second signal is transferred to the feedback device resulting in physical stimulation of the user's affected physical extremity by the therapist, and wherein the instantiation of kinetic imagery of the simulated physical action and the physical stimulation of the user's affected physical extremity are associated with improving performance of the physical actions of the user.

3. A method for remotely improving performance of physical actions of a user with an affected brain comprising:

providing an apparatus to the user having one or more self-teaching virtual training games stored therein that, upon execution, simulate at least one physical action using one or more controllable digital anatomical virtual extremities;

creating the one or more controllable digital anatomical virtual extremities; each said controllable digital anatomical virtual extremity being configured to the user by storing measured user anatomical data and measured user physiological data in a database and creating an extremity model based on a model data derived from said anatomical and physiological data;

constructing one or more pre-coded digital anatomical virtual extremities simulating one or more physical anatomical actions;

displaying on a display device the one or more controllable digital anatomical virtual extremities;

displaying on the display device the one or more pre-coded digital anatomical virtual extremities;

receiving, from an input device controlled by the user, inputs that control a simulated physical action of the one or more controllable digital anatomical virtual extremities constructed by the apparatus conjoined with one or more of the pre-coded digital anatomical virtual extremities constructed by the apparatus;

wherein the received user inputs controlling the controllable digital anatomical virtual extremities instantiate a kinetic imagery of the simulated physical action of the user;

attaching a feedback device to a user's affected physical extremity, wherein upon a motion of the controllable digital anatomical virtual extremity representing the user's affected physical extremity on the display device, a first signal is transferred to the feedback device resulting in physical stimulation of the user's affected physical extremity, receiving, from an input device controlled by a remote therapist, a second signal that alters the motion of the controllable digital anatomical virtual extremity representing the user's affected physical extremity on the display device, wherein the second signal is transferred to the feedback device resulting in physical stimulation of the user's affected physical extremity by the therapist, and wherein the instantiation of kinetic imagery of the simulated physical action and the physical stimulation of the user's affected physical extremity are associated with improving performance of the physical actions of the user.

* * * * *